United States Patent
Pirali et al.

(10) Patent No.: US 10,519,138 B2
(45) Date of Patent: Dec. 31, 2019

(54) MODULATORS OF SOCE, COMPOSITIONS, AND USES THEREOF

(71) Applicant: Università degli Studi del Piemonte Orientale "Amedeo Avogadro", Vercelli (IT)

(72) Inventors: Tracey Pirali, Novara (IT); Armando A. Genazzani, Novara (IT); Beatrice Riva, Cerrione (IT)

(73) Assignee: UNIVERSITA DEGLI STUDI DEL PIEMONTE ORIENTALE, Vercelli (IT)

( * ) Notice: Subject to any disclaimer, the term of this patent is extended or adjusted under 35 U.S.C. 154(b) by 0 days.

(21) Appl. No.: 16/308,187

(22) PCT Filed: Jun. 7, 2017

(86) PCT No.: PCT/IB2017/053355
§ 371 (c)(1),
(2) Date: Dec. 7, 2018

(87) PCT Pub. No.: WO2017/212414
PCT Pub. Date: Dec. 14, 2017

(65) Prior Publication Data
US 2019/0300509 A1    Oct. 3, 2019

(30) Foreign Application Priority Data
Jun. 8, 2016   (IT) .................. 102016000058684

(51) Int. Cl.
*C07D 401/14*   (2006.01)
*C07D 403/10*   (2006.01)
*C07D 413/14*   (2006.01)

(52) U.S. Cl.
CPC ......... *C07D 403/10* (2013.01); *C07D 401/14* (2013.01); *C07D 413/14* (2013.01)

(58) Field of Classification Search
CPC .................. C07D 401/14; C07D 403/10
See application file for complete search history.

(56) References Cited

U.S. PATENT DOCUMENTS

2009/0111799 A1    4/2009   Chen et al.

FOREIGN PATENT DOCUMENTS

| WO | 2003/031435 A1 | 4/2003 | |
| WO | 2010/122088 A1 | 10/2010 | |
| WO | 2011/042797 A1 | 4/2011 | |
| WO | WO-2014152738 A1 * | 9/2014 | ............. C07D 13/14 |

OTHER PUBLICATIONS

PCT Search Report and Written Opinion for PCT/IB2017/053355, dated Jul. 27, 2017.

* cited by examiner

*Primary Examiner* — Laura L Stockton
(74) *Attorney, Agent, or Firm* — Vivicar Law, PLLC

(57) ABSTRACT

Compounds of Formula (I) able to modulate Store Operated Calcium Entry (SOCE). The disclosure also relates to the use of compounds of formula (I) for treatment of pathological conditions in which SOCE modulation might be beneficial, such as neglecting disorders linked to loss- or gain-of-function STIM1/Orai1 mutations, allergic disorders, pain, inflammatory diseases, autoimmune diseases or disorders, cancer and other proliferative diseases, neurodegenerative disorders, myelodysplastic syndromes, haematological diseases, cardiovascular diseases, degenerative diseases of the musculoskeletal system, liver diseases and disorders, kidney diseases, type I diabetes, graft rejection, graft-versus-host disease, allogeneic or xenogeneic transplantation, thyroiditis and viral infections.

11 Claims, 6 Drawing Sheets

2A)

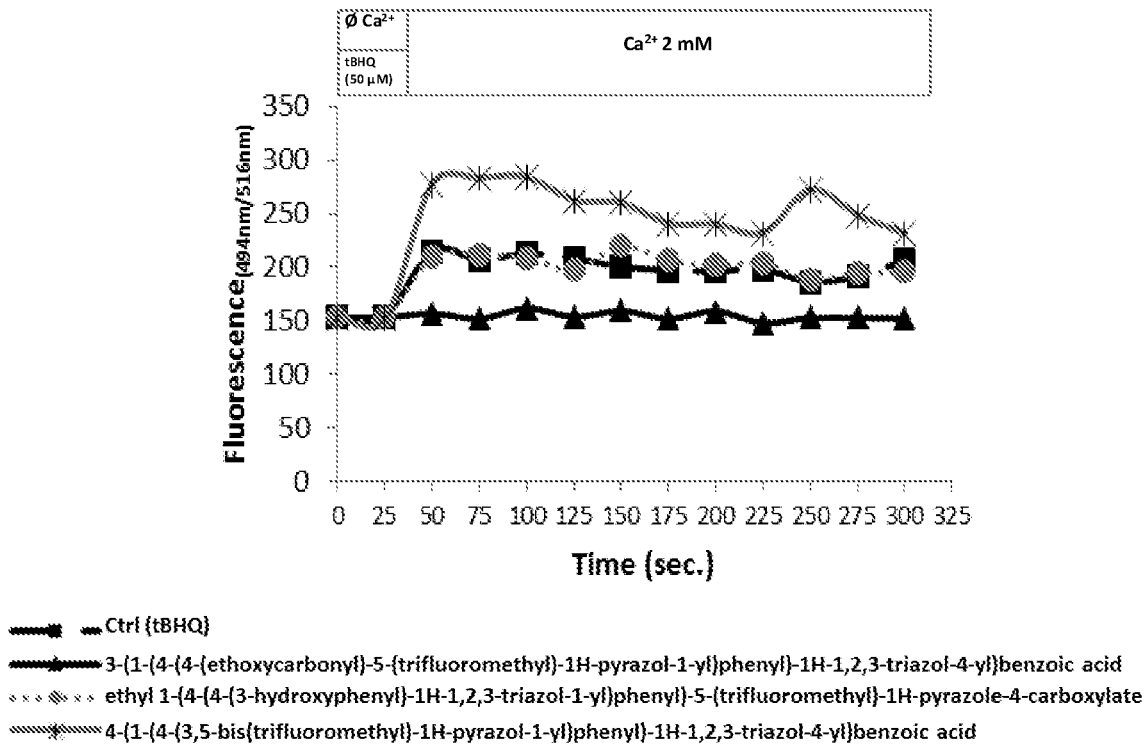

— Ctrl (tBHQ)
— 3-(1-{4-(4-(ethoxycarbonyl)-5-(trifluoromethyl)-1H-pyrazol-1-yl)phenyl)-1H-1,2,3-triazol-4-yl)benzoic acid
⋯ ethyl 1-{4-(4-(3-hydroxyphenyl)-1H-1,2,3-triazol-1-yl)phenyl)-5-(trifluoromethyl)-1H-pyrazole-4-carboxylate
— 4-(1-{4-(3,5-bis(trifluoromethyl)-1H-pyrazol-1-yl)phenyl)-1H-1,2,3-triazol-4-yl)benzoic acid

2B)

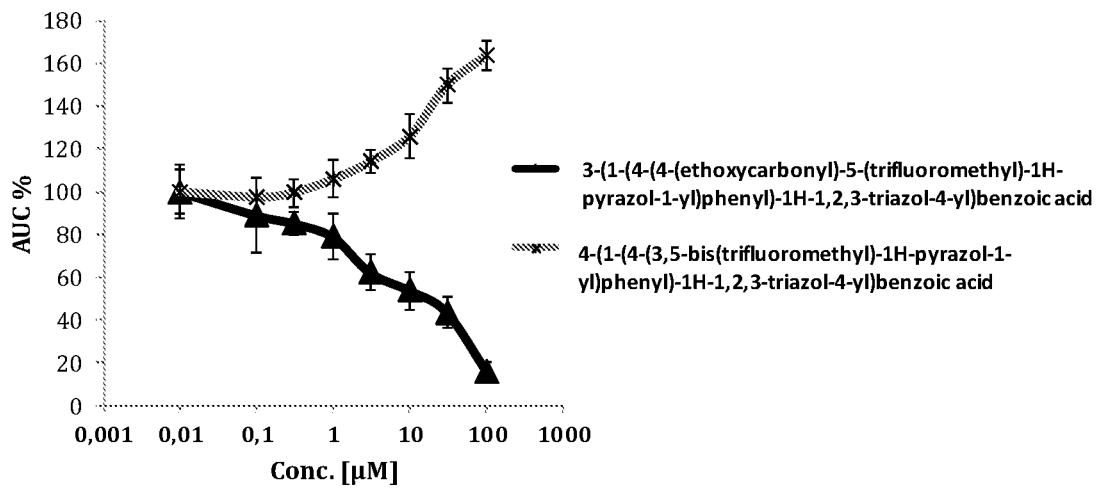

— 3-(1-(4-(4-(ethoxycarbonyl)-5-(trifluoromethyl)-1H-pyrazol-1-yl)phenyl)-1H-1,2,3-triazol-4-yl)benzoic acid
⋯ 4-(1-(4-(3,5-bis(trifluoromethyl)-1H-pyrazol-1-yl)phenyl)-1H-1,2,3-triazol-4-yl)benzoic acid

Figure 2

5A)
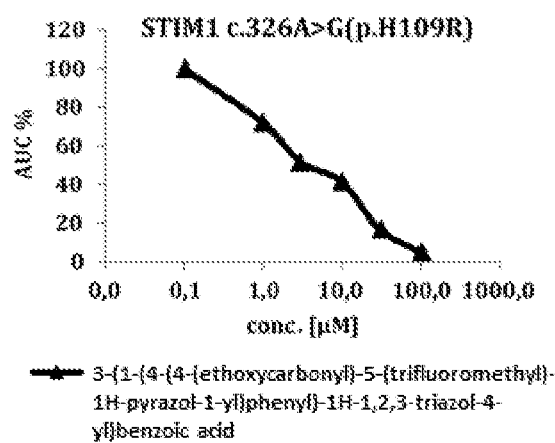
5B)
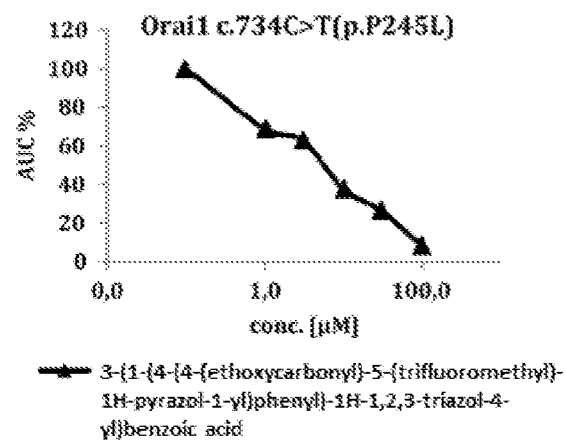
Figure 5

MODULATORS OF SOCE, COMPOSITIONS, AND USES THEREOF

CROSS-REFERENCE TO RELATED APPLICATIONS

This application is the national stage application of corresponding international application number PCT/IB2017/053355, filed Jun. 7, 2017, which claims priority to and the benefit of Italian application no. 102016000058684, filed Jun. 8, 2016.

FIELD OF THE INVENTION

The disclosure concerns new compounds able to modulate the calcium entry operated by endoplasmic reticulum, also known as Store Operated Calcium Entry (SOCE), compositions, and uses thereof.

BACKGROUND OF THE INVENTION

Calcium ($Ca^{2+}$) is a multifunctional signalling ion that regulates a wide range of cellular functions ranging from short-term responses, such as contraction and secretion, to longer-term control of transcription, cell division and cell death (Jeremy T. Smyth, et al.; 2010. J. Cell. Mol. Med. Vol 14, No 10, pp. 2337-2349; Lewis Richard S. 2011 Cold Spring Harb Perspect Biol; 3:a003970). The very low concentration of $Ca^{2+}$ in the cytosol together with the massive gradient across membranes ($Ca^{2+}$ is $10^5$ times more abundant in organelles and in the extracellular medium) became thereafter a great opportunity to use this ion as a specific second messenger. A $Ca^{2+}$-signal encodes a message through its amplitude, the duration of its rise, the frequency of its rises and the exact spatial localization in the cell. It has grown to such specialization that hundreds of proteins govern this process and each cell type has a unique set of proteins that are chosen for particular tasks, the "$Ca^{2+}$ toolkit", as defined by one of the fathers of modern $Ca^{2+}$ signalling (Berridge M J, Bootman M D, Roderick H L. 2003. Nature Reviews. Molecular Cell Biology 4:517-529). As mentioned above, high concentrations of $Ca^{2+}$ are present in intracellular organelles (with particular reference to the endoplasmic reticulum/sarcoplasmic reticulum (ER/SR)) and in the extracellular space and $Ca^{2+}$-fluxes occur through channels located on the plasma membrane or on the membrane of intracellular organelles. Given that $Ca^{2+}$-pumps and exchangers are located on both membranes to extrude $Ca^{2+}$ from the cytosol, it would be expected that the intracellular organelle pool would be soon depleted. Among these pathways, store-operated-$Ca^{2+}$ entry (SOCE), so named for its regulation by the free $Ca^{2+}$ concentration ($[Ca^{2+}]$) of the ER $Ca^{2+}$ stores, is a widespread $Ca^{2+}$ entry mechanism in animal cells that delivers $Ca^{2+}$ to refill ER stores and evoke cellular $Ca^{2+}$ signals (Putney J W. 2011. Frontiers in Bioscience (Scholar Edition) 3:980-984).

Store-operated $Ca^{2+}$ entry is associated with the electrophysiological current $I_{CRAC}$, first described by Hoth and Penner (Hoth M, Penner R. 1992. Nature 355:353-356). The exact molecular mechanisms behind this phenomenon have been elusive for a number of years, but it is now thought that the principal components of the machinery are the $Ca^{2+}$-release-activated-$Ca^{2+}$ (CRAC) channels. CRAC channels are assembled from two fundamental protein complexes: Orai proteins, that form the ion channel pore, and the stromal interaction molecule (STIM) proteins, which function as ER calcium sensor and activators of the CRAC channels (Berna-Erro A, et al. Redondo P C, Rosado J A. 2012. Medicine and Biology 740:349-382; Soboloff J, Rothberg B S, Madesh M, Gill D L. 2012. Nature Reviews. Molecular Cell Biology 13:549-565.; Lacruz R S, Feske S. 2015. Annals of the New York Academy of Sciences 1356:45-79.). Moreover, it is important to stress that other crucial proteins participate in the SOCE process, including TRPC channels (Ong H L, Ambudkar I S. 2015. Cell Calcium 58:376-386).

STIM proteins are single-span membrane proteins, highly conserved across species. Two members of the family have been described, STIM1 and STIM2, of which the former appears more expressed. Roos et al. (2005; J Cell Biol.; 169(3):435-45.) using a limited RNAi screen of *Drosophila* S2 cells identified *Drosophila* STIM as having a fundamental role in SOCE activation, and a similar conclusion was reached almost concurrently for human STIM1 and STIM2 in a HeLa cell screen (Jeremy T. Smyth, et al.; 2010. J. Cell. Mol. Med. Vol 14, No 10, pp. 2337-2349, Lewis Richard S. 2011 Cold Spring Harb Perspect Biol; 3:a003970). STIM1 was identified as a $Ca^{2+}$ sensor for SOCE since it is specialized for responding to significant changes in ER $Ca^{2+}$ signals. STIM1 localization is crucial to its role SOCE: when $Ca^{2+}$ stores are full STIM1 is localized in tubular structures throughout the ER membrane, but when stores are depleted it moves to punctate structures at site where the ER is directly apposed to the plasma membrane. This re-localization of STIM1 within the ER towards the plasma membrane allows the direct or indirect interaction and activation of Orai channels. Orai channels reside on the plasma membrane and three members of the family (Orai1, Orai2, and Orai3) have been described, with Orai1 being the most abundant and closely connected to the $I_{CRAC}$ (Jeremy T. Smyth, et al.; 2010. J. Cell. Mol. Med. Vol 14, No 10, pp. 2337-2349; Lewis Richard S. 2011 Cold Spring Harb Perspect Biol; 3:a003970; Feske S, et al; 2005 J Exp Med.; 202(5):651-62; Nature; 11; 441(7090):179-85.).

CRAC currents were initially identified in lymphocyte and mast cells, and simultaneously characterized in different cell lines such as DT40 B cells, hepatocytes, dendritic, megakaryotic and Madin-Darby canine kidney cells. In lymphocyte and mast cells, the activation through antigen or Fc receptor initiates the release of $Ca^{2+}$ ion from intracellular stores caused by the second messenger inositol (1,4,5)-triphosphate ($IP_3$), that leads to $Ca^{2+}$ ion influx through CRAC channels in the plasma membrane.

CRAC channels also mediate crucial function from secretion to gene expression and cell growth and form a process essential for the activation of adaptive immune response. It has been demonstrated that $Ca^{2+}$ oscillations triggered through stimulation of the T-cell antigen receptor (TCR) involved only the influx pathway of the store operated CRAC channel. Therefore, $Ca^{2+}$ ion influx mediated by the store operated CRAC channel is fundamental in lymphocyte activation (Anant B. Parekh and James W. Putney Jr.; 2005; Physiol Rev 85: 757-810.; Hogan G. p., et al; 2010; Annu. Rev. Immunol. 28:491-533; Patrick G Hogan and Anjana Rao; 2015; Biochem Biophys Res Commun. 24; 460(1): 40-49.; Feske S, Okamura H, Hogan P G, Rao A. 2003; Biochem Biophys Res Commun.; 311(4):1117-32.). Conversely, the store-operated $Ca^{2+}$ currents identified in endothelial cells, smooth muscle, epidermal cells and prostate cancer cells lines show altered biophysical characteristic suggesting a different molecular origin. These evidences demonstrate that intracellular $Ca^{2+}$ plays an important role in different cellular functions, and its concentration by $Ca^{2+}$ influx through $Ca^{2+}$ channels on the plasma membrane and ER.

Furthermore, the importance of CRAC channels for human health is underlined by an increasing list of genetic studies that have identified that patients who bear loss- or gain-of-function STIM1/Orai1 mutations suffer from severe health issues, including muscle defects, immunodeficiency, autoimmunity and bleeding disorders (Feske S. 2010; European Journal of Physiology 460:417-435). Regarding loss-of-function mutations, at least three unrelated families have been described that, due to different mutations, including frame-shifts, do not express Orai1 on the plasma membrane of T-lymphocytes, lack store-operated $Ca^{2+}$-entry and are thereby unable to activate T-lymphocytes (Feske S, Muiller J M, Graf D, Kroczek R A, Drager R, Niemeyer C, Baeuerle P A, Peter H H, Schlesier M. 1996. European Journal of Immunology 26:2119-2126.; McCarl C A, et al.; 2009. J Allergy Clin Immunol.; 124(6):1311-1318.e7.) Notably, families with STIM1 mutations that lead to no expression of the protein have been reported and are characterized by a T-cell immunodeficiency (Picard C, et al.; 2009, N Engl J Med. 7; 360(19):1971-80.; Byun M, et al.; 2010. The Journal of Experimental Medicine. 207:2307-2312.; Fuchs S, et al.; 2012. Journal of Immunology (Baltimore, Md.: 1950) 188: 1523-1533). Last, while immunodeficiency is the hallmark of the disease, these patients also display lymphoproliferative diseases, autoimmunity, congenital myopathy, anhydrosis, dental enamel, and an impairment in thrombus formation due to a defect in platelet activation. While some mutations give rise to a decreased activity that might be potentiated pharmacologically, most mutations yield a significant decrease in protein expression and therefore pharmacological approaches might be indicated also for these disorders. Currently, the loss-of-function mutations of STIM1 and Orai1 reported in the literature are the following: p.P165Q, p.R429C, p.R426C, p.E128RfsX9 for STIM1, and p.R91W, p.A103E, p.L194P, p.A88SfsX25 and p.H165PfsX1 for Orai1.

Gain-of-function mutations of STIM1 or Orai1 affect primarily skeletal muscles and platelets. Patients with STIM1 or Orai1 gain-of-function mutations exhibit a wide and likely continuous spectrum of symptoms that affect multiple organs and are different in intensity, progression and in age of onset. Yet, skeletal muscle and platelets appear the main systems affected. Three separate disorders (tubular aggregate myopathy, Stormorken syndrome and York platelet syndrome) are described in the literature and can be reconducted to mutations in one of these two proteins (Lacruz R S, Feske S. 2015. Annals of the New York Academy of Sciences 1356:45-79). Tubular aggregate myopathy (TAM) can be re-conducted to gain-of-function mutations in either STIM1 and Orai1, and is clinically characterized by variable combinations of myalgias, cramps and muscle stiffness, with or without weakness with a predominantly proximal distribution (Bihm J, et al. 2013. American Journal of Human Genetics 92:271-278; Nesin V, et al. 2014. Proceedings of the National Academy of Sciences of the United States of America 111:4197-4202; Endo Y, et al. 2015. Human Molecular Genetics 24:637-648.) and by the presence of tubular aggregates, which are regular arrays of tubules derived from the sarcoplasmic reticulum, on muscle pathology (Schiaffino S. 2012. Neuromuscul Disord 22:199-207.). Stormorken syndrome (Stormorken H, et al. 1995. Thromb Haemost 74:1244-1251) associates to the myopathic signs, but may also include mild bleeding tendency due to platelet dysfunction, thrombocytopenia, anemia, asplenia, congenital miosis, ichthyosis, and may also include headache or recurrent stroke-like episodes (Misceo D, et al 2014. Human Mutation 35:556-564.). Also in this case, both STIM1 and Orai1 (Nesin V, et al. 2014. Proceedings of the National Academy of Sciences of the United States of America 111:4197-4202) mutations have been associated with the syndrome. Last, the York platelet syndrome, recently described in the United States, sees blood dyscrasias as the main phenotype (Markello T et al. Molecular Genetics and Metabolism 114:474-482.) and has, so far, only been associated to STIM1 mutations. Currently, the gain-of-function mutations of STIM1 and Orai1 reported in the literature are the following: p.F108I, p.I115F, p.H109R, p.H72Q, p.N80T, p.G81D, p.D84G, p.L96V, p.F108L, p.H109N, p.R304W, p.R304G for STIM1; and p.S97C, p.G98S, p.L138F, p.P245L for Orai1.

Briefly, mutations of STIM1 mostly reside in the EF-hand $Ca^{2+}$-binding motifs, most likely modifying the affinity for $Ca^{2+}$ ions of the protein, with the single exception of a mutation located in the cytosolic side of the protein on a coil-coiled domain that is likely to affect dimerization/oligomerization of STIM1, a likely trigger of Orai1 channel opening. The mutations of Orai1 are located in the transmembrane domains in positions that might lead to the assumption that they participate in the channel lining.

All these data suggest that SOCE modulators would be useful for the treatment of diseases caused by an abnormal SOCE. A key limitation in the study of SOCE and its physio- and pathophysiological role is the lack of potent and selective modulators. Some agents are available (Sweeney Z K, Minatti A, Button D C, Patrick S. 2009. ChemMedChem 4:706-718), but they share common drawbacks in terms of lacking potency and/or specificity over CRAC channels. Lanthanides ($Ln^{3+}$) are nonselective cation channel blockers, while 2-aminoethoxydiphenylborate (2-APB), a repurposed inositol triphosphate receptor inhibitor, is a nonspecific blocker, which potentiates $I_{CRAC}$ at low micromolar concentrations, while inhibiting $I_{CRAC}$ at higher concentrations (Diver J M, et al. 2001. Cell Calcium 30:323-329). Carboxyamido-triazole (CAI) is a synthetic small molecule inhibitor of non-voltage-gated $Ca^{2+}$ channels that has entered Phase I, II and III clinical trials, both as single cytostatic agent and in combination with cytotoxic therapies. CAI is, however, a nonspecific agent that may target cellular pathways other than non-voltage-gated $Ca^{2+}$ channels (Lodola F, et al. 2012. PloS One 7:e42541.Lodola et al., 2012). While small molecules used in the past (2-APB, CAI) were found to be unselective, second generation modulators should block CRAC channels with a certain degree of selectivity. Synta66, a compound developed by GSK, inhibits $IC_{RAC}$ with an $IC_{50}$ of 0.3 µM (Di Sabatino A. 2009. Journal of Immunology (Baltimore, Md.: 1950) 183:3454-3462), while Hoffmann-La Roche has recently reported the discovery of RO2959, a potent CRAC channel inhibitor with $IC_{50}$ values of about 200 nM (Chen G, et al. 2013. Molecular Immunology 54:355-367). To achieve these $IC_{50}$ values, however, this molecule has to be pre-incubated with cells for 30 to 60 minutes suggesting that it may act on Orai1 indirectly. Very recently, Dolmetsch et al. have screened a small-molecule microarray through an innovative approach that makes use of minimal functional domains and discovered AnCoA4, an isoflavone able to bind to and inhibit Orai1 at submicromolar concentrations (Sadaghiani A M, et al. 2014. Chemistry & Biology 21:1278-1292), but no data about its specificity are available.

Much interest has been directed at a series of 3,5-bistrifluoromethyl pyrazole derivatives, referred to as BTPs and disclosed by Abbott in 2000 (Djuric S W, et al. 2000. Journal of Medicinal Chemistry 43:2975-2981.; US 20010044445; US 20010044445). Specifically, BTP2 (Pyr2, YM-58483) is a potent inhibitor, but has pleiotropic effects on both Orai and TRPC channels (Takezawa R, et al. 2006. Molecular Pharmacology 69:1413-1420). Subsequently, other pyrazoles, identified as Pyr, have been reported. Pyr3, a previously suggested selective inhibitor of TRPC3 (Kiyonaka S, et al. 2009. Proceedings of the National Academy of Sciences of the United States of America 106:5400-5405; Glasnov T. N. et al., ChemMedChem, 2009, 4:1816-1818), was shown to inhibit both TRPC3- and Orai1 mediated $Ca^{2+}$ entry (Schleifer H, et al. 2012. British Journal of Pharmacology 167:1712-1722). By contrast, two compounds, Pyr6 and Pyr10, are able to distinguish to a certain degree between Orai and TRPC-mediated $Ca^{2+}$ entry (Schleifer H, et al. 2012. British Journal of Pharmacology 167:1712-1722). Most of these reported compounds display a pyrazole ring with at 1-position an arylamide moiety. Similar compounds are described in WO2006115140 by Astellas Pharma (Yonetoku Y. et al. Bioorg. Med. Chem. 2006, 14, 4750-4760; 2008, 16, 9457-9466; 2006, 14, 5370-5383), where pyrazolic CRAC inhibitors are reported to be useful in bowel diseases. Other patent publications relating to similar CRAC channel modulators include the applications by Icozen Therapeutics and Rhizen Pharmaceuticals, WO 2011042797 and WO2011042798, where the reported inhibitors are pyrazole derivatives in which a substituted pyrazole is bound to a phenyl or pyridine group carrying an inverse amide in para-position. Bioisosteric replacement of the arylamide moiety with a fused heterocycle scaffold led to a series of pyrazolic modulators described by Hoffmann-La Roche in the applications WO2013050270, WO2013050341, US20130158066, US20130158049 and US20130158040. GlaxoSmithKline published two separate patent applications in 2010: the first (WO2010122088) comprises both pyrazole and triazole carboxamides, while the second (WO2010122089) focuses exclusively on N-pyrazolyl carboxamides. The amide bond is reversed in WO2010122088 as compared with WO2010122089. Calcimedica reported pyrazole compounds as CRAC channels inhibitors in WO2011139765, US2011263612, WO2010048559 and WO2009076454.

Despite all the reported applications, there remains an unmet and dire need for small molecule modulators having specificity towards Stim1 and/or Orai1 in order to regulate activity of CRAC channels, particularly for the treatment of diseases and disorders associated with SOCE.

SUMMARY OF THE INVENTION

The object of this disclosure is to provide new compounds able to modulate SOCE.

According to the invention, the above object is achieved thanks to the subject matter recalled specifically in the ensuing claims, which are understood as forming an integral part of this disclosure.

The present invention provides a class of compounds as novel SOCE modulators and their use in therapy. More particularly, the invention provides a family of 5-(trifluoromethyl)-1H-pyrazoles with at 1-position a phenyl ring carrying a triazole in para-position.

The present disclosure provides compounds of formula (I):

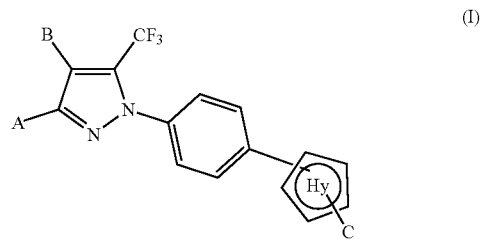

wherein:
A is selected from H or $CF_3$;
B is selected from H, COOH or $COOR_1$;
ring Hy is selected from:

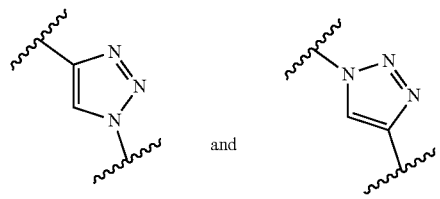 [SMILES: *c1cn(*)nn1 ; *c1cn(*)nn1]

and

C is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_m$—$C_{1-8}$ alkyl, $(CH_2)_m$—$C_{2-8}$ alkenyl, $(CH_2)_m$—$C_{2-8}$ alkynyl group, $(CH_2)_m$-cycloalkyl, $(CH_2)_m$-aryl and $(CH_2)_m$-heterocyclic group, wherein m is an integer 1 to 4;

$R_1$ is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_n$—$C_{1-8}$ alkyl, $(CH_2)_n$—$C_{2-8}$ alkenyl, $(CH_2)_n$—$C_{2-8}$ alkynyl group, $(CH_2)_n$-cycloalkyl, $(CH_2)_n$-aryl and $(CH_2)_m$-heteroaryl, wherein n is an integer 1 to 4;

pharmaceutically acceptable hydrates and/or solvates and/or salts and/or esters and/or pro-drugs thereof.

The disclosure relates to 5-(trifluoromethyl)-1H-pyrazoles of formula (I) with a specific activity on SOCE.

The disclosure also relates to the use of the compounds of formula (I) for in vivo treatment of pathological conditions in which SOCE modulation might be beneficial, such as allergic disorders, inflammatory diseases, pain, autoimmune diseases or disorders, cancer and other proliferative diseases, neurodegenerative disorders, myelodysplastic syndromes, haematological diseases, cardiovascular diseases, degenerative diseases of the musculoskeletal system, liver diseases and disorders, kidney diseases, type I diabetes, graft rejection, graft-versus-host disease, allogeneic or xenogeneic transplantation, thyroiditis, viral infections and neglecting disorders linked to loss- or gain-of-function STIM1/Orai1 mutations (tubular aggregate myopathy (TAM), Stormorken syndrome and York platelet syndrome).

The disclosure also provides pharmaceutical compositions comprising at least one compound of formula (I) and a pharmaceutically acceptable carrier. The pharmaceutical composition may further comprise one or more additional therapeutic agents.

BRIEF DESCRIPTION OF THE DRAWINGS

The invention will now be described in detail, purely by way of illustrative and non-limiting example, with reference to the attached figures, wherein:

FIG. 2: Calcium response to SOCE-modulators.
(A) BV-2 cells were plated in poly-d-lysine coated 24-well plate and incubated overnight. After 24 hours, cells were loaded with 2 μM Fluo-4 and placed in an extracellular solution containing 0 mM $Ca^{2+}$. Stores were depleted with 50 μM tBHQ and calcium influx was stimulated by the addition of 2 mM $Ca^{2+}$ alone (Ctrl), or in conbination with: compound with no activity (NM-3A), and compounds that positively (4-(1-(4-(3,5-bis(trifluoromethyl)-1H-pyrazol-1-yl)phenyl)-1H-1,2,3-triazol-4-yl)benzoic acid) and negatively (3-(1-(4-(4-(ethoxycarbonyl)-5-(trifluoromethyl)-1H-pyrazol-1-yl)phenyl)-1H-1,2,3-triazol-4-yl)benzoic acid) regulate SOCE. Calcium responses are expressed as changes in fluorescence intensity before and after the addition of selected modulators.
(B) BV-2 cells were assayed for a calcium response to different concentrations of 3-(1-(4-(4-(ethoxycarbonyl)-5-(trifluoromethyl)-1H-pyrazol-1-yl)phenyl)-1H-1,2,3-triazol-4-yl)benzoic acid and 4-(1-(4-(3,5-bis(trifluoromethyl)-1H-pyrazol-1-yl)phenyl)-1H-1,2,3-triazol-4-yl) benzoic acid (0.1-0.3-1-3-10-30-100 μM) using Fluo-4 fluorimetric assay. Concentration-response curves represent the AUC % of both compounds as compared to positive control.

FIG. 5: Dose-dependent inhibition of SOCE by 3-(1-(4-(4-(ethoxycarbonyl)-5-(trifluoromethyl)-1H-pyrazol-1-yl)phenyl)-1H-1,2,3-triazol-4-yl)benzoic acid.
HEK STIM1 c.326A>G p.H109R (A) and HEK Orai1 c.734C>T p.P245L (B) cells were assayed for a calcium response to different concentrations of 3-(1-(4-(4-(ethoxycarbonyl)-5-(trifluoromethyl)-1H-pyrazol-1-yl)phenyl)-1H-1,2,3-triazol-4-yl)benzoic acid (1-3-10-30-100 μM) using Fura2-AM single cell analysis. Concentration-response curves represent the AUC % of 3-(1-(4-(4-(ethoxycarbonyl)-5-(trifluoromethyl)-1H-pyrazol-1-yl)phenyl)-1H-1,2,3-triazol-4-yl)benzoic acid.

DETAILED DESCRIPTION OF THE INVENTION

Figure 1:
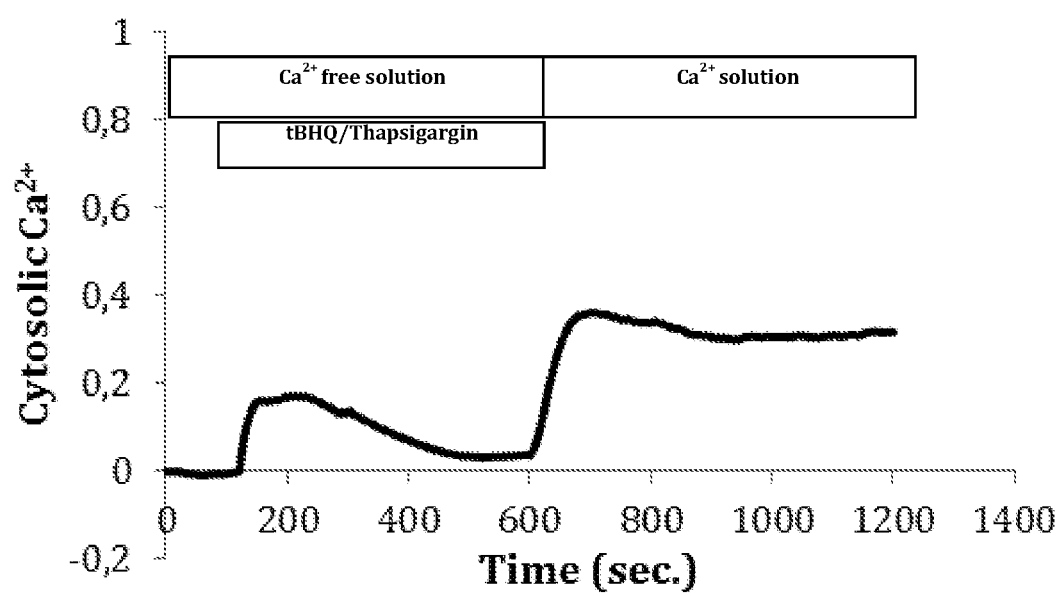
FIG. 1: Representative trace of Store Operated Calcium Entry (SOCE).
Experiments were carried out prior to and during exposure of the cells to the $Ca^{2+}$-free solution. In the absence of $Ca^{2+}$, the intracellular $Ca^{2+}$ stores were depleted by 2,5-t-butyl-hydroquinone (tBHQ, 50 μM; Sigma-Aldrich, Italy), a SERCA poison, and then calcium 2 mM was re-added to the extracellular solution.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

An embodiment of the present disclosure provides compounds of formula (I):

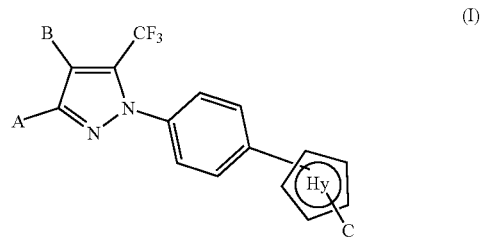

wherein:
A is selected from H or $CF_3$;
B is selected from H, COOH or $COOR_1$;
ring Hy is selected from:

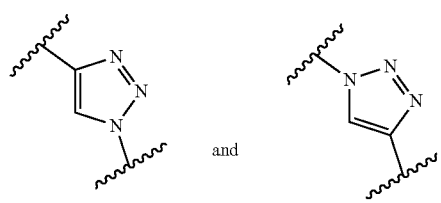 [SMILES: *c1cn(*)nn1 ; *c1cn(*)nn1]

and

C is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_m$—$C_{1-8}$ alkyl, $(CH_2)_m$—$C_{2-8}$ alkenyl, $(CH_2)_m$—$C_{2-8}$ alkynyl group, $(CH_2)_m$-cycloalkyl, $(CH_2)_m$-aryl and $(CH_2)_m$-heterocyclic group, wherein m is an integer 1 to 4;
$R_1$ is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_n$—$C_{1-8}$ alkyl, $(CH_2)_n$—$C_{2-8}$ alkenyl, $(CH_2)_n$—$C_{2-8}$ alkynyl group, $(CH_2)_n$-cycloalkyl, $(CH_2)_n$-aryl and $(CH_2)_n$-heteroaryl, wherein n is an integer 1 to 4;
pharmaceutically acceptable hydrates and/or solvates and/or salts and/or esters and/or prodrugs thereof.

A further embodiment concerns compounds of formula (II):

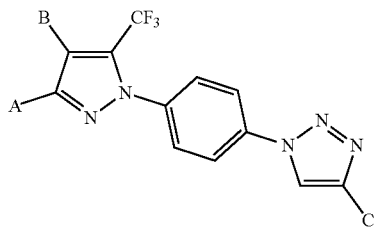

wherein A, B and C have the meaning as defined above, pharmaceutically acceptable hydrates and/or solvates and/or salts and/or esters and/or prodrugs thereof.

A further embodiment concerns compounds of formula (III):

(III)

wherein A, B and C have the meaning as defined above, pharmaceutically acceptable hydrates and/or solvates and/or salts and/or esters and/or prodrugs thereof.

In an embodiment, when $R_1$ and C, if present, are independently selected from substituted $C_{1-8}$ alkyl group, substituted $C_{3-6}$ cycloalkyl, substituted aryl, substituted heterocyclic group, substituted $C_{2-8}$ alkenyl group, substituted $C_{2-8}$ alkynyl group, the one or more substituents are independently selected from halogen, —$CH_3$, —$CH_2F$, —$CHF_2$, —$CF_3$, —$OR_2$, —CN, —$COOR_2$, —$CONR_2R_3$, —$NR_2R_3$, —$NHCOR_2$, —$NHSO_2R_2$, —$S(O)R_2$, —$S(O)_2R_2$, and —$SO_2NHR_2$;

wherein $R_2$ and $R_3$ are the same or different and independently selected from H, $C_1$-$C_8$ alkyl group unsubstituted or substituted with one or more halogen atoms and $C_3$-$C_6$ cycloalkyl group unsubstituted or substituted with one or more halogen atoms.

In a preferred embodiment, $R_1$ is selected from unsubstituted methyl, ethyl, tert-butyl, iso-propyl, pentan-2-yl, pyridine-4-yl methyl, benzyl, 2-morpholinoethyl, and 1,1,1,3,3,3-hexafluoro-2-methylpropan-2-yl.

In an embodiment, A is selected from H, and $CF_3$.
In a further embodiment, B is selected from H, and COOH.
In a further embodiment, C is selected from:

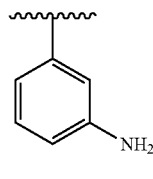 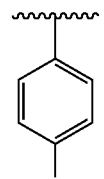 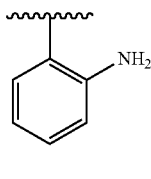

-continued

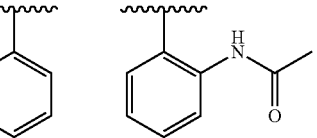 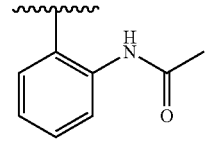

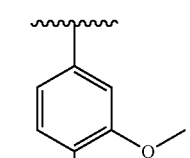 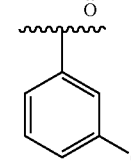 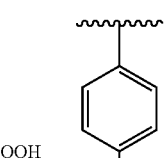

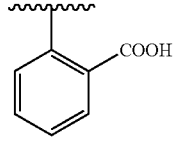 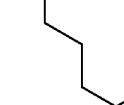 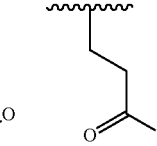

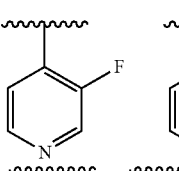 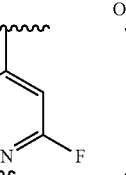 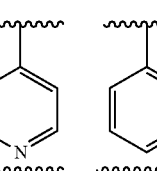

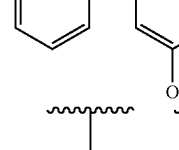 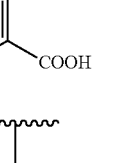 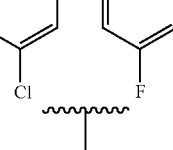

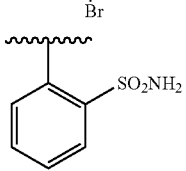 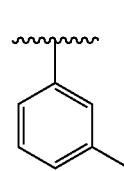 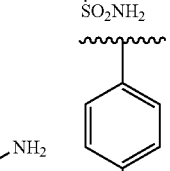

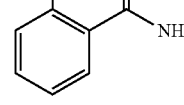 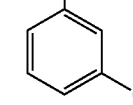 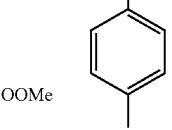

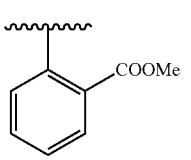 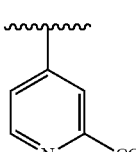 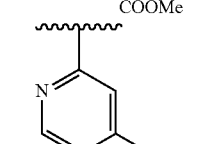

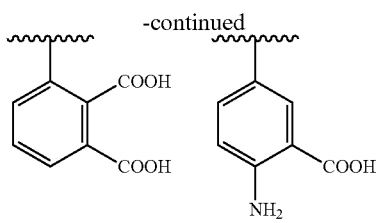

The term "alkyl" refers to a monovalent straight or branched chain group derived from an unsaturated hydrocarbon of one to eight carbons. The alkyl groups of this invention can be optionally substituted.

The term "alkenyl" refers to a monovalent straight or branched chain group derived from a hydrocarbon of two to eight carbons having at least one carbon-carbon double bond. The alkenyl groups of this invention can be optionally substituted.

The term "alkynyl" refers to a monovalent straight or branched chain group derived from a hydrocarbon of two to eight carbons having at least one carbon-carbon triple bond. The alkynyl groups of this invention can be optionally substituted.

The term "aryl" refers to a mono- or bicyclic carbocyclic ring system having at least one aromatic ring that can be optionally substituted. The aryl group can be fused to a cyclohexane, cyclohexene, cyclopentane or cyclopentene ring in which case the aryl group can be attached through the ring to which it is attached or through the aromatic ring itself. The aryl groups of this invention can be optionally substituted.

The term "cycloalkyl" refers to a monovalent saturated cyclic or bicyclic hydrocarbon of three to six carbons. The cycloaclkyl groups of this invention can be optionally substituted.

The term "halogen" refers to F, Cl, Br, or I.

The term "heterocyclic" refers to a 4-, 5-, 6- or 7-membered ring containing one, two or three heteroatoms independently selected from the group consisting of nitrogen, oxygen and sulfur. The 4- and 5-membered rings have 0, 1, or 2 double bonds and the 6- and 7-membrered rings have 0, 1, 2, or 3 double bonds. The nitrogen and sulfur atoms can be optionally oxidized, and the nitrogen atom can be optionally quaternized. The term "heterocyclic" also includes bicylic, tricyclic, and tetracyclic groups in which a heterocyclic ring is fused to one or two rings selected from an aryl ring, a cyclohexane ring, a cyclohexene ring, a cyclopentane ring, a cyclopentene ring or another monocyclic heterocyclic ring. Heterocycles of this type can be attached through the ring to which they are fused or through the heterocyclic ring itself. Heterocycles include, but are not limited to, acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorholinyl, triazolyl, and the like. The heterocycle groups of this invention can be optionally substituted.

The term "pharmaceutically acceptable prodrugs" refers to those prodrugs of the compounds of the present invention which are, within the scope of sound medical judgement, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the invention.

The term "prodrug" refers to compounds which are rapidly transformed in vivo into the parent compound of the above formula, by a reaction under physiological conditions with an enzyme, a gastric acid or in the living body through oxidation, reduction, hydrolysis or enzymatic reaction. Examples of prodrugs are compounds wherein the carboxyl group is esterified. These prodrugs can be produced from compounds of formula (I) according to well-known methods and as exemplified in the General Synthesis of compounds of formula (I).

The term "pharmaceutically acceptable salt" refers to those salts which are, within the scope of sound medical judgement, suitable for use in contact with the tissues of humans and lower animals without undue toxicity, irritation, allergic response and the like and are commensurate with a reasonable benefit/risk ratio.

Metabolites of compounds of formula (I) are also within the scope of the present disclosure. The term "metabolites" refers to all molecules derived from any of the compounds in a mammal cell or organism. Metabolite products typically are identified by preparing a radiolabeled ($^{14}C$ or $^{3}H$) isotope of a compound of the disclosure, administering it parenterally in a detectable dose, more than 0.5 mg/kg of body weight, to an animal such as rat, mouse, guinea pig, monkey, or to human, allowing a sufficient time for metabolism (max 30 hours) and isolating its conversion products from blood, urine or other biological samples. The metabolite structures are determined by MS, LC/MS or NMR analysis.

Compounds of formula (I) herein described are useful for the treatment of disease condition depending on increased/decreased activity of SOCE. Such diseases have been identified with allergic disorders, pain, inflammatory diseases, autoimmune diseases or disorders, cancer and other proliferative diseases, neurodegenerative disorders, myelodysplastic syndromes, haematological diseases, cardiovascular diseases, degenerative diseases of the musculoskeletal system, liver diseases and disorders, kidney diseases, type I diabetes, graft rejection, graft-versus-host disease, allogeneic or xenogeneic transplantation, thyroiditis, viral infections and neglecting disorders linked to loss- or gain-of-function STIM1/Orai1 mutations.

Accordingly, the compounds of formula (I) are useful for the prevention or treatment of:

Diseases linked to loss- or gain-of-function STIM1/Orai1 mutations, including but not limited to, immunodeficiencies (T-cell immunodeficiency, lymphoproliferative diseases, autoimmunity, congenital myopathy, anhydrosis, dental enamel, and an impairment in thrombus formation due to a defect in platelet activation), tubular aggregate myopathy (TAM), Stormorken syndrome and York platelet syndrome.

Allergic disorders, including allergic rhinitis, sinusitis, rhinosinusitis, drug reactions, atopic dermatitis, food allergies, latex allergy, anaphylaxis and anaphylactoid reactions, conjunctivitis, chronic or recurrent otitis and urticarial;

Pain, including, without limitation, inflammatory pain, visceral pain, premenstrual pain, surgical pain, dental pain, central pain nerve injury, neuritis, neuralgias, migraine or cluster pains, poisoning, ischemic injury, post-traumatic injury, interstitial cystitis, viral, bacterial or parasitic infection pain associated with irritable bowel syndrome and cancer pain;

Inflammatory diseases, including lung disorders (such as asthma, acute respiratory distress syndrome, acute lung injury, chronic obstructive pulmonary disease, pulmonary fibrosis bronchiectasis and cystic fibrosis), chronic inflammatory disorders of joints (such as arthritis, rheumatoid arthritis, osteoarthritis and bone diseases associated with increased bone resorption), Sjogren's syndrome, inflammatory bowel disease (such as Barrett's oesophagus, ileitis, ulcerative colitis and Crohn's disease), neuro-inflammatory diseases (such as chronic demyelinating diseases of the nervous system, multiple sclerosis, AIDS-related neurodegeneration and Alzheimer disease, infectious meningitis, encephalomyelitis, Parkinson's disease, Huntington's disease, amyotrophic lateral sclerosis and viral or autoimmune encephalitis), brain and spinal cord trauma, inflammatory disorders of the eye (such as corneal dystrophy, trachoma, uveitis, sympathetic ophthalmitis and endophthalmitis, allergic conjunctivitis), inflammatory diseases of the kidney (such as glomerulonephritis, nephrosis, nephritic syndrome and IgA nephropathy), hepatic diseases or disorders, primary biliary cirrhosis, chronic liver failure, chronic relapsing hepatitis, vasculitis, dermatitis, inflammatory disorders of the skin (such as psoriasis, dermatomyositis and eczema), inflammatory muscle disease, inflammatory diseases of the heart (such as myocarditis and cardiomyopathy, ischemic heart disease, myocardial infarction and atherosclerosis), osteoarthritis, vaginitis, interstitial cystitis, mastocytosis, endometriosis, allergic rhinitis, scleroderma, osteoporosis, allogeneic or xenogeneic transplantation, graft rejection, graft-versus-host disease, tuberculosis, leprosy, pre-eclampsia, lupus erythematosus, type I diabetes, thyroiditis, myasthenia gravis, endotoxic shock, septic shock, haemorrhagic or anaphylactic shock or shock induced by cancer chemotherapy and autoimmune haemolytic anemia;

Autoimmune diseases, including, but not limited to, autoimmune diseases of the eye (such as autoimmune uveitis); autoimmune diseases of the blood (such as autoimmune haemolytic anemia, pernicious anemia, and autoimmune thrombocytopenia i.e. Idiopathic Thrombocytopaenic Purpura), autoimmune diseases of the central and peripheral nervous system (such as multiple sclerosis, myasthenia gravis, Eaton-Lambert Myasthenic syndrome), autoimmune neurophathies (such as Guillain-Barre), autoimmune diseases of the vasculature (such as anti-phospholipid syndrome, vasculitides i.e. Wegener's granulomatosis, temporal arteritis, and Behcet's disease); autoimmune diseases of the skin (such as dermatitis herpetiformis, pemphigus vulgaris, bullous pemphigoid alopecia areata, psoriasis, and vitiligo); autoimmune disease of the gastrointestinal tract (such as Crohn's disease, ulcerative colitis, coeliac disease, primary biliary cirrhosis and autoimmune hepatitis); autoimmune disorder of the adrenal gland (such as Addisons disease), and multi system autoimmune diseases including musculoskeletal system disease and connective tissue (such as systemic lupus erythematosus, scleroderma, rheumatoid arthritis, polymyositis, dermatomyositis), spondyloarthropathies (such as ankylosing spondylitis and psoriatic arthritis), autoimmune disorders of the endocrine glands (such as Typei diabetes mellitus, autoimmune thyroiditis, Grave's disease, Hashimoto's thyroiditis, autoimmune oophoritis and orchitis), autoimmune mediated glomerulonephritis, inflammatory bowel disease and autoimmune type I diabetes;

Neurodegenerative disorders, including, but not limited to, Alzheimer's disease, AIDS-related dementia, Parkinson's disease, amyotrophic lateral sclerosis, retinitis pigmentosa, spinal muscular atrophy and cerebellar degeneration);

Myelodysplastic syndromes, including, but not limited to, cytopenias, dysplasia, refractory anemia (RA), refractory anemia with ring sideroblasts (RARS), refractory anemia with excess blasts (RAEB), refractory anemia with excess blasts in transformation (RAEB-T), and chronic myelomonocytic leukemia (CMML);

Hematological diseases (chronic anemia and aplastic anemia);

Cardiovascular diseases, such as: ischemic injury associated with myocardial infarctions, stroke and reperiusion injury, arrhythmia and atherosclerosis and vascular thrombosis (venous, arterial and intra-cardiac);

Degenerative diseases of the musculoskeletal system (including, osteoporosis and arthritis);

Liver diseases and disorders that include but are not limited to: liver injury due to transplantation, hepatitis cirrhosis and other alcohol related liver diseases;

Kidney diseases like those caused by different mechanism of injury (for example immunological injury), including IgA nephropathy (Berger's disease), glomerural diseases, membranoproliferative glomerulonephritis and lupus nephritis;

Variety of cancer, including:

tumors of mesenchymal origin including rhabdomyosarcoma;

hematopoietic tumors of lymphoid lineage, including leukemia, acute lymphocytic leukemia, acute lymphoblastic leukemia, Hodgkin's lymphoma, non-Hodgkins lymphoma, B-cell lymphoma, T-cell lymphoma, hairy cell lymphoma and Burkett's lymphoma;

hematopoietic tumors of myeloid lineage, including acute and chronic myelogenous leukemias, myelodysplastic syndrome and promyelocytic leukemia;

breast, colon, kidney, liver and lung carcinoma, oesophagus, gall bladder, ovary, pancreas, stomach, cervix, thyroid, prostate, and skin cancer, including squamous cell carcinoma and small cell lung cancer;

tumors of the central and peripheral nervous system, including astrocytoma, neuroblastoma, glioma and schwannomas;

other tumors, including melanoma, thyroid follicular cancer, Kaposi's sarcoma, osteosarcoma, xenoderoma pigmentosum, seminoma, teratocarcinoma and keratoctanthoma, Viral infections including, but not limited to, herpesvirus, poxvirus, Epstein-Bar virus, Sindbis virus and adenovirus;

Prevention of AIDS development in HIV-infected individuals.

Compounds of formula (I) can be administered in various routes appropriate to the condition to be treated. Suitable routes include oral, parenteral (including subcutaneous, intramuscular, intravenous, intra-arterial, intradermal, intrathecal and epidural), transdermal, rectal, nasal, topical (including buccal and sublingual), vaginal, intraperitoneal, intrapulmonary and intranasal.

Compounds of formula (I) can be formulated as a pharmaceutical composition in the form of tablet, capsule, aqueous solution, granule, powder, suspension, cream, syrup, gel, emulsion, and the like.

The dosage depends on a variety of factors including the age, weight and condition of the patient and the route of administration. Although daily dosage can vary from one individual to another, the compound/s will be administered to an adult human in a range of 0.0001-50 mg/kg of body weight as daily single dose or 0.01 to 1 mg/kg as daily repeated doses.

Tablets contain the compound/s of formula (I) in a mixture with non-toxic pharmaceutically excipients suitable for the manufacture of tablets. Exemplary excipients could be: inert diluents, such as sodium carbonate, lactose, dextrose, cellulose etc.; granulating and disintegrating agents as maize starch, glycolate, alginic acid; binding agents as gelatin or acacia; lubricating agents, for example silica magnesium or calcium stearate, stearic acid or talc. For preparing suppositories, a mixture of for example fatty acid glycerides or cocoa butter is first melted and the compound/s of formula (I) is/are dissolved homogenously by stirring. The homogenous mixture is then cooled into convenient sized molds. Liquid preparations, which include solutions, suspensions and emulsions, contain the formula (I) compound/s in a mixture of excipients suitable for the manufacture of aqueous suspension such as sodium carboxymethylcellulose, methylcellulose, resin, sodium alginate and natural or synthetic gums. Eventually the liquid preparation may contain suitable colorants, flavors, stabilizers, preservatives and thickening agents as desired.

Compounds of the present invention may also be co-administered with one or more additional therapeutic agents.

Compounds of formula (I) include, but are not limited to, the compounds shown in Table 1.

TABLE 1

| Name | Structure |
|---|---|
| ethyl 1-(4-(4-phenyl-1H-1,2,3-triazol-1-yl)phenyl)-5-(trifluoromethyl)-1H-pyrazole-4-carboxylate | 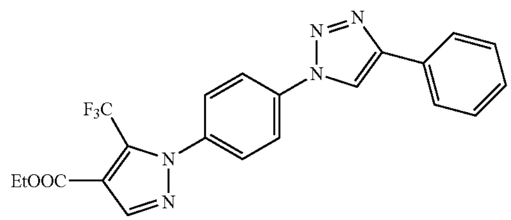 [SMILES: CCOC(=O)c1cnn(-c2ccc(-n3cc(-c4ccccc4)nn3)cc2)c1C(F)(F)F] |
| ethyl 1-(4-(4-(4-methoxyphenyl)-1H-1,2,3-triazol-1-yl)phenyl)-5-(trifluoromethyl)-1H-pyrazole-4-carboxylate | 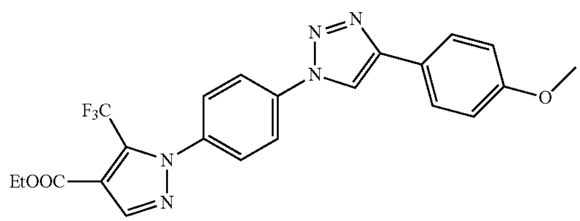 [SMILES: CCOC(=O)c1cnn(-c2ccc(-n3cc(-c4ccc(OC)cc4)nn3)cc2)c1C(F)(F)F] |
| ethyl 1-(4-(4-(3,5-dimethoxyphenyl)-1H-1,2,3-triazol-1-yl)phenyl)-5-(trifluoromethyl)-1H-pyrazole-4-carboxylate | 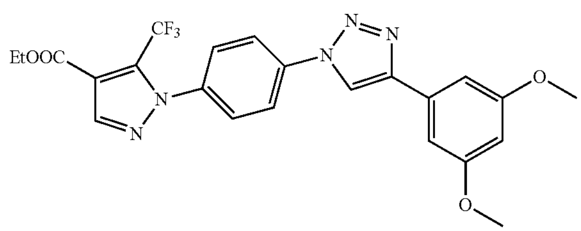 [SMILES: CCOC(=O)c1cnn(-c2ccc(-n3cc(-c4cc(OC)cc(OC)c4)nn3)cc2)c1C(F)(F)F] |
| 4-(1-(4-(4-(ethoxycarbonyl)-5-(trifluoromethyl)-1H-pyrazol-1-yl)phenyl)-1H-1,2,3-triazol-4-yl)butanoic acid | 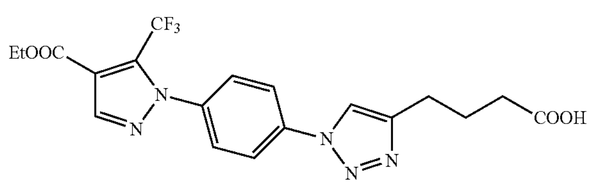 [SMILES: CCOC(=O)c1cnn(-c2ccc(-n3cc(CCCC(=O)O)nn3)cc2)c1C(F)(F)F] |
| ethyl 1-(4-(4-(4-aminophenyl)-1H-1,2,3-triazol-1-yl)phenyl)-5-(trifluoromethyl)-1H-pyrazole-4-carboxylate | 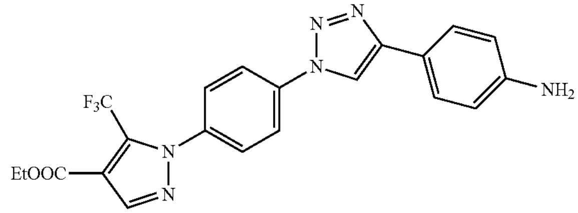 [SMILES: CCOC(=O)c1cnn(-c2ccc(-n3cc(-c4ccc(N)cc4)nn3)cc2)c1C(F)(F)F] |

TABLE 1-continued

| Name | Structure |
|---|---|
| ethyl 1-(4-(4-(3-hydroxyphenyl)-1H-1,2,3-triazol-1-yl)phenyl)-5-(trifluoromethyl)-1H-pyrazole-4-carboxylate | 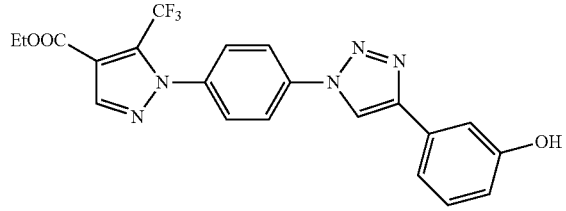 [SMILES: CCOC(=O)c1cnn(-c2ccc(-n3cc(-c4cccc(O)c4)nn3)cc2)c1C(F)(F)F] |
| ethyl 1-(4-(4-(4-chlorophenyl)-1H-1,2,3-triazol-1-yl)phenyl)-5-(trifluoromethyl)-1H-pyrazole-4-carboxylate | 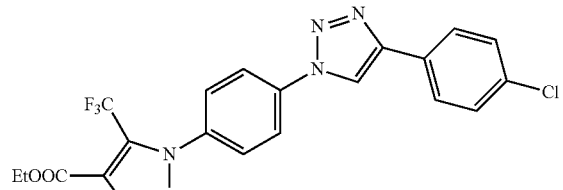 |
| ethyl 1-(4-(4-(3-aminophenyl)-1H-1,2,3-triazol-1-yl)phenyl)-5-(trifluoromethyl)-1H-pyrazole-4-carboxylate | 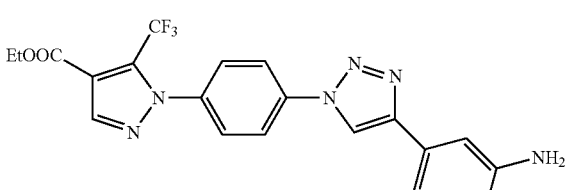 |
| ethyl 1-(4-(4-(pyridin-3-yl)-1H-1,2,3-triazol-1-yl)phenyl)-5-(trifluoromethyl)-1H-pyrazole-4-carboxylate | 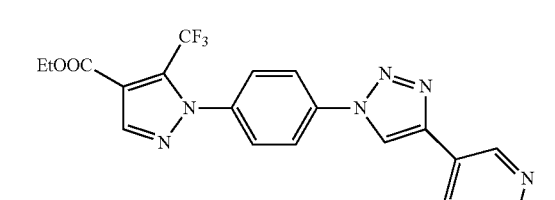 |
| ethyl 1-(4-(4-(3-aminophenyl)-1H-1,2,3-triazol-1-yl)phenyl)-5-(trifluoromethyl)-1H-pyrazole-4-carboxylate | 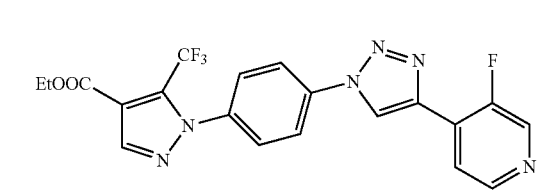 [SMILES: CCOC(=O)c1cnn(-c2ccc(-n3cc(-c4ccncc4F)nn3)cc2)c1C(F)(F)F] |
| ethyl 1-(4-(4-(pyridin-2-yl)-1H-1,2,3-triazol-1-yl)phenyl)-5-(trifluoromethyl)-1H-pyrazole-4-carboxylate | 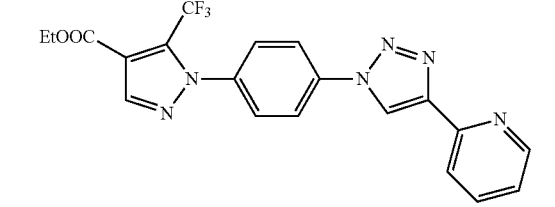 [SMILES: CCOC(=O)c1cnn(-c2ccc(-n3cc(-c4ccccn4)nn3)cc2)c1C(F)(F)F] |
| ethyl 1-(4-(4-(pyridin-4-yl)-1H-1,2,3-triazol-1-yl)phenyl)-5-(trifluoromethyl)-1H-pyrazole-4-carboxylate | 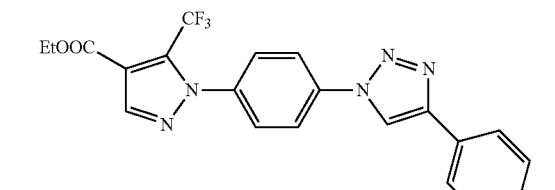 |

TABLE 1-continued

| Name | Structure |
|---|---|
| ethyl 1-(4-(4-(3,4-dimethoxyphenyl)-1H-1,2,3-triazol-1-yl)phenyl)-5-(trifluoromethyl)-1H-pyrazole-4-carboxylate | 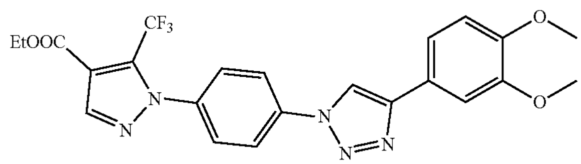 [SMILES: CCOC(=O)c1cnn(-c2ccc(-n3cc(-c4ccc(OC)c(OC)c4)nn3)cc2)c1C(F)(F)F] |
| ethyl 1-(4-(4-(4-hydroxy-3-methoxyphenyl)-1H-1,2,3-triazol-1-yl)phenyl)-5-(trifluoromethyl)-1H-pyrazole-4-carboxylate | 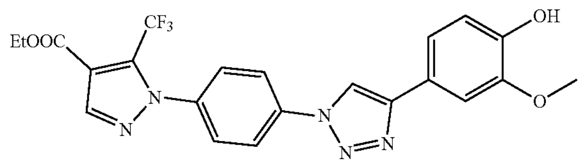 [SMILES: CCOC(=O)c1cnn(-c2ccc(-n3cc(-c4ccc(O)c(OC)c4)nn3)cc2)c1C(F)(F)F] |
| ethyl 1-(4-(4-(3-methoxyphenyl)-1H-1,2,3-triazol-1-yl)phenyl)-5-(trifluoromethyl)-1H-pyrazole-4-carboxylate | 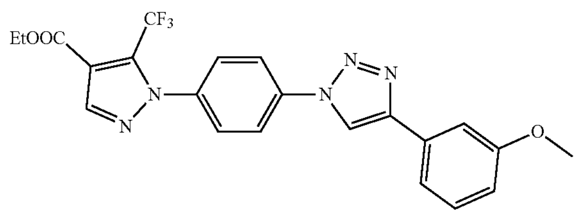 [SMILES: CCOC(=O)c1cnn(-c2ccc(-n3cc(-c4cccc(OC)c4)nn3)cc2)c1C(F)(F)F] |
| ethyl 1-(4-(4-(2-acetamidophenyl)-1H-1,2,3-triazol-1-yl)phenyl)-5-(trifluoromethyl)-1H-pyrazole-4-carboxylate | |
| ethyl 1-(4-(4-(3-acetamidophenyl)-1H-1,2,3-triazol-1-yl)phenyl)-5-(trifluoromethyl)-1H-pyrazole-4-carboxylate | 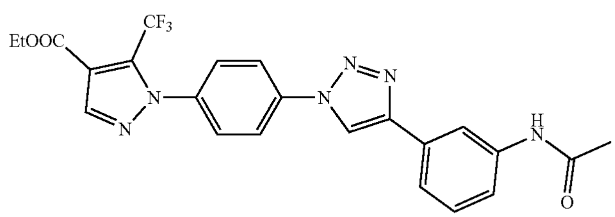 [SMILES: CCOC(=O)c1cnn(-c2ccc(-n3cc(-c4cccc(NC(C)=O)c4)nn3)cc2)c1C(F)(F)F] |
| ethyl 1-(4-(4-(2-acetamidophenyl)-1H-1,2,3-triazol-1-yl)phenyl)-5-(trifluoromethyl)-1H-pyrazole-4-carboxylate | |
| 3-(1-(4-(4-(ethoxycarbonyl)-5-(trifluoromethyl)-1H-pyrazol-1-yl)phenyl)-1H-1,2,3-triazol-4-yl)benzoic acid | 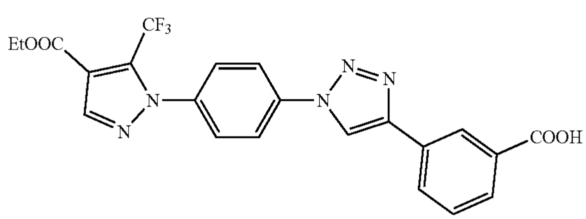 [SMILES: CCOC(=O)c1cnn(-c2ccc(-n3cc(-c4cccc(C(=O)O)c4)nn3)cc2)c1C(F)(F)F] |

TABLE 1-continued

| Name | Structure |
|---|---|
| 4-(1-(4-(4-(ethoxycarbonyl)-5-(trifluoromethyl)-1H-pyrazol-1-yl)phenyl)-1H-1,2,3-triazol-4-yl)benzoic acid | 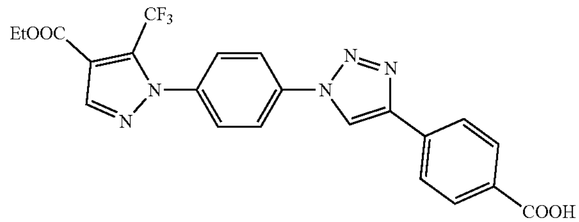 [SMILES: CCOC(=O)c1cnn(-c2ccc(-n3cc(-c4ccc(C(=O)O)cc4)nn3)cc2)c1C(F)(F)F] |
| ethyl 1-(4-(4-(4-phenoxyphenyl)-1H-1,2,3-triazol-1-yl)phenyl)-5-(trifluoromethyl)-1H-pyrazole-4-carboxylate | 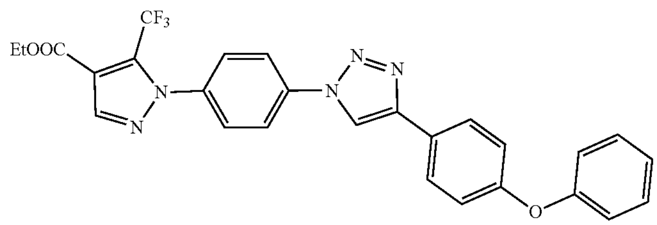 [SMILES: CCOC(=O)c1cnn(-c2ccc(-n3cc(-c4ccc(Oc5ccccc5)cc4)nn3)cc2)c1C(F)(F)F] |
| 1-(4-(3,5-bis(trifluoromethyl)-1H-pyrazol-1-yl)phenyl)-4-phenyl-1H-1,2,3-triazole | 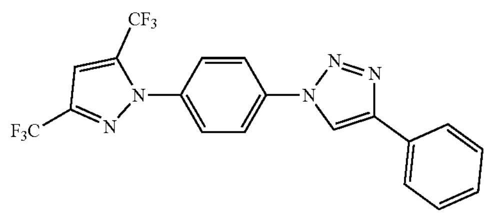 [SMILES: FC(F)(F)c1cc(C(F)(F)F)n(-c2ccc(-n3cc(-c4ccccc4)nn3)cc2)n1] |
| 1-(4-(3,5-bis(trifluoromethyl)-1H-pyrazol-1-yl)phenyl)-4-(4-methoxyphenyl)-1H-1,2,3-triazole | 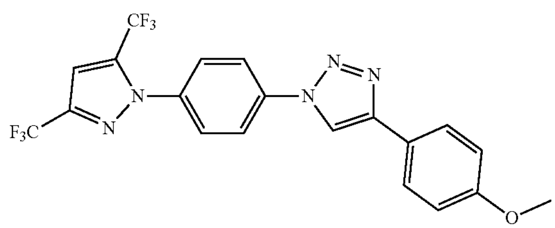 [SMILES: COc1ccc(-c2cn(-c3ccc(-n4nc(C(F)(F)F)cc4C(F)(F)F)cc3)nn2)cc1] |
| 1-(4-(3,5-bis(trifluoromethyl)-1H-pyrazol-1-yl)phenyl)-4-(3,5-dimethoxyphenyl)-1H-1,2,3-triazole | 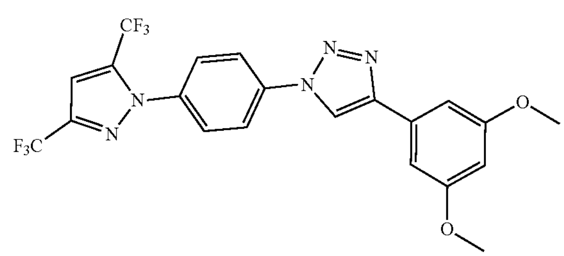 [SMILES: COc1cc(OC)cc(-c2cn(-c3ccc(-n4nc(C(F)(F)F)cc4C(F)(F)F)cc3)nn2)c1] |
| 4-(1-(4-(3,5-bis(trifluoromethyl)-1H-pyrazol-1-yl)phenyl)-1H-1,2,3-triazol-4-yl)butanoic acid | 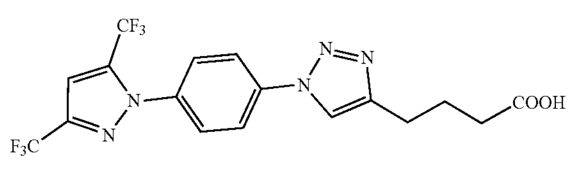 [SMILES: O=C(O)CCCc1cn(-c2ccc(-n3nc(C(F)(F)F)cc3C(F)(F)F)cc2)nn1] |
| 4-(1-(4-(3,5-bis(tiifluoromethyl)-1H-pyrazol-1-yl)phenyl)-1H-1,2,3-triazol-4-yl)aniline | 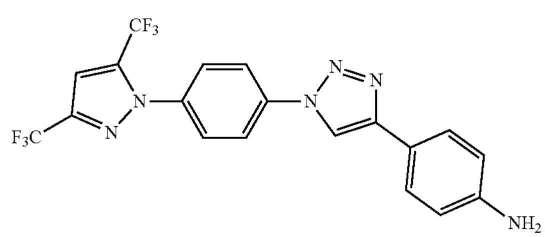 [SMILES: Nc1ccc(-c2cn(-c3ccc(-n4nc(C(F)(F)F)cc4C(F)(F)F)cc3)nn2)cc1] |

TABLE 1-continued

| Name | Structure |
|---|---|
| 3-(1-(4-(3,5-bis(trifluoromethyl)-1H-pyrazol-1-yl)phenyl)-1H-1,2,3-triazol-4-yl)phenol | 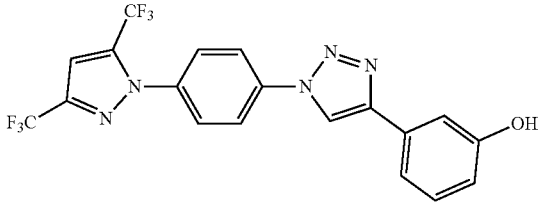 [SMILES: Oc1cccc(-c2cn(-c3ccc(-n4nc(C(F)(F)F)cc4C(F)(F)F)cc3)nn2)c1] |
| 1-(4-(3,5-bis(trifluoromethyl)-1H-pyrazol-1-yl)phenyl)-4-(4-chlorophenyl)-1H-1,2,3-triazole | 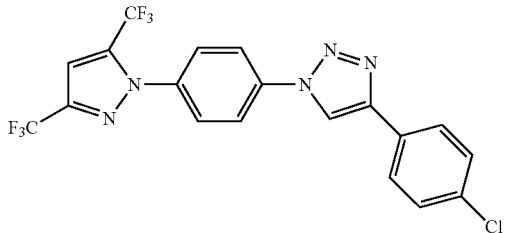 [SMILES: FC(F)(F)c1cc(C(F)(F)F)n(-c2ccc(-n3cc(-c4ccc(Cl)cc4)nn3)cc2)n1] |
| 3-(1-(4-(3,5-bis(difluoromethyl)-1H-pyrazol-1-yl)phenyl)-1H-1,2,3-triazol-4-yl)aniline | 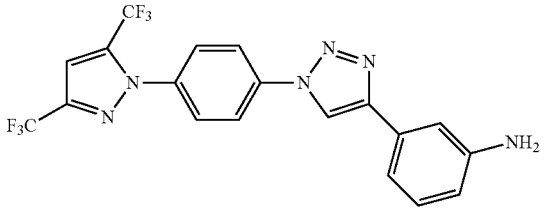 [SMILES: Nc1cccc(-c2cn(-c3ccc(-n4nc(C(F)(F)F)cc4C(F)(F)F)cc3)nn2)c1] |
| 3-(1-(4-(3,5-bis(trifluoromethyl)-1H-pyrazol-1-yl)phenyl)-1H-1,2,3-triazol-4-yl)pyridine | 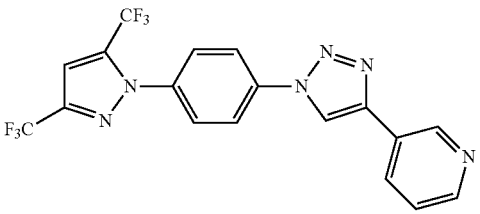 [SMILES: FC(F)(F)c1cc(C(F)(F)F)n(-c2ccc(-n3cc(-c4cccnc4)nn3)cc2)n1] |
| 4-(1-(4-(3,5-bis(trifluoromethyl)-1H-pyrazol-1-yl)phenyl)-1H-1,2,3-triazol-4-yl)-3-fluoropyridine | 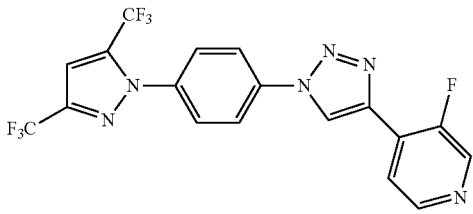 [SMILES: Fc1cnccc1-c1cn(-c2ccc(-n3nc(C(F)(F)F)cc3C(F)(F)F)cc2)nn1] |
| 2-(1-(4-(3,5-bis(trifluoromethyl)-1H-pyrazol-1-yl)phenyl)-1H-1,2,3-triazol-4-yl)pyridine | 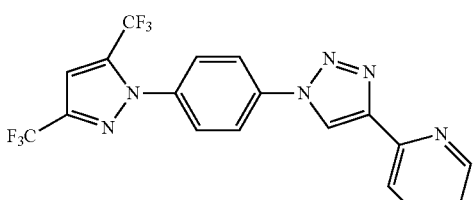 |
| 4-(1-(4-(3,5-bis(trifluoromethyl)-1H-pyrazol-1-yl)phenyl)-1H-1,2,3-triazol-4-yl)pyridine | 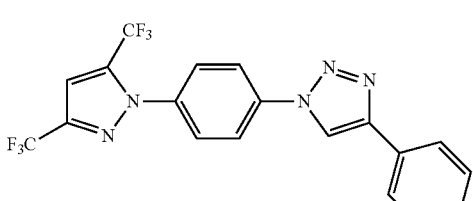 |

TABLE 1-continued

| Name | Structure |
|---|---|
| 1-(4-(3,5-bis(trifluoromethyl)-1H-pyrazol-1-yl)phenyl)-4-(3,4-dimethoxyphenyl)-1H-1,2,3-triazole | 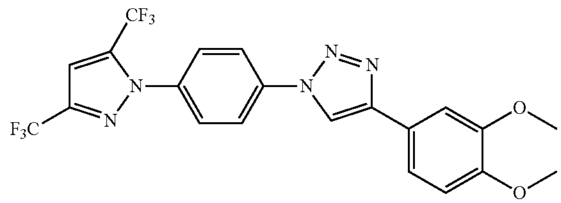 [SMILES: COc1ccc(-c2cn(-c3ccc(-n4nc(C(F)(F)F)cc4C(F)(F)F)cc3)nn2)cc1OC] |
| 4-(1-(4-(3,5-bis(trifluoromethyl)-1H-pyrazol-1-yl)phenyl)-1H-1,2,3-triazol-4-yl)-2-methoxyphenol | 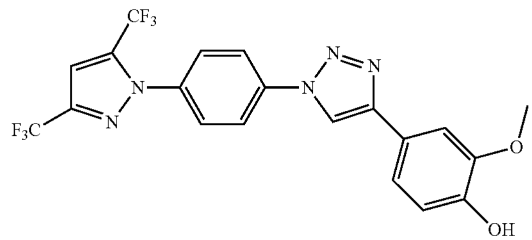 [SMILES: COc1cc(-c2cn(-c3ccc(-n4nc(C(F)(F)F)cc4C(F)(F)F)cc3)nn2)ccc1O] |
| 1-(4-(3,5-bis(trifluoromethyl)-1H-pyrazol-1-yl)phenyl)-4-(3-methoxyphenyl)-1H-1,2,3-triazole | 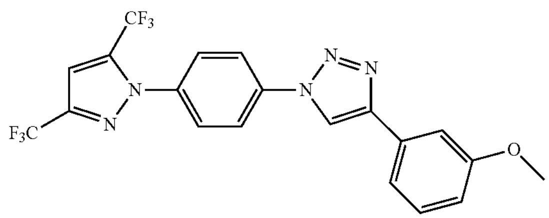 [SMILES: COc1cccc(-c2cn(-c3ccc(-n4nc(C(F)(F)F)cc4C(F)(F)F)cc3)nn2)c1] |
| N-(4-(1-(4-(3,5-bis(trifluoromethyl)-1H-pyrazol-1-yl)phenyl)-1H-1,2,3-triazol-4-yl)phenyl)acetamide | 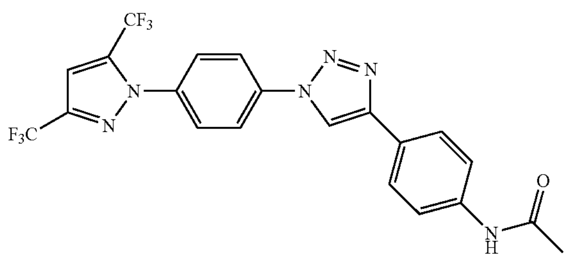 [SMILES: CC(=O)Nc1ccc(-c2cn(-c3ccc(-n4nc(C(F)(F)F)cc4C(F)(F)F)cc3)nn2)cc1] |
| N-(3-(1-(4-(3,5-bis(trifluoromethyl)-1H-pyrazol-1-yl)phenyl)-1H-1,2,3-triazol-4-yl)phenyl)acetamide | 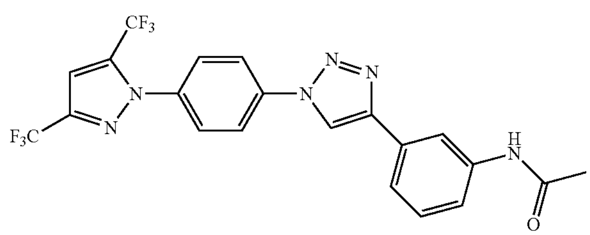 [SMILES: CC(=O)Nc1cccc(-c2cn(-c3ccc(-n4nc(C(F)(F)F)cc4C(F)(F)F)cc3)nn2)c1] |
| N-(2-(1-(4-(3,5-bis(trifluoromethyl)-1H-pyrazol-1-yl)phenyl)-1H-1,2,3-triazol-4-yl)phenyl)acetamide | |
| N-(2-(1-(4-(3,5-bis(trifluoromethyl)-1H-pyrazol-1-yl)phenyl)-1H-1,2,3-triazol-4-yl)phenyl)acetamide | |

TABLE 1-continued

| Name | Structure |
|---|---|
| 4-(1-(4-(3,5-bis(trifluoromethyl)-1H-pyrazol-1-yl)phenyl)-1H-1,2,3-triazol-4-yl)benzoic acid | 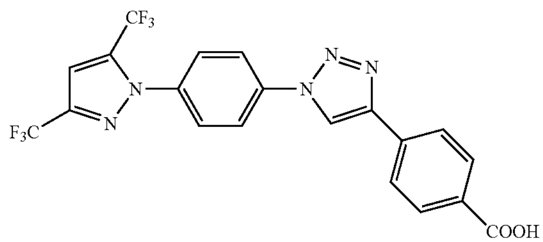 [SMILES: O=C(O)c1ccc(-c2cn(-c3ccc(-n4nc(C(F)(F)F)cc4C(F)(F)F)cc3)nn2)cc1] |
| 1-(4-(3,5-bis(trifluoromethyl)-1H-pyrazol-1-yl)phenyl)-4-(4-phenoxyphenyl)-1H-1,2,3-triazole | 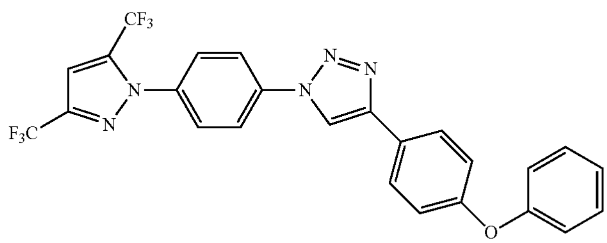 [SMILES: FC(F)(F)c1cc(C(F)(F)F)n(-c2ccc(-n3cc(-c4ccc(Oc5ccccc5)cc4)nn3)cc2)n1] |
| ethyl 1-(4-(1-phenyl-1H-1,2,3-triazol-4-yl)phenyl)-5-(trifluoromethyl)-1H-pyrazole-4-carboxylate | 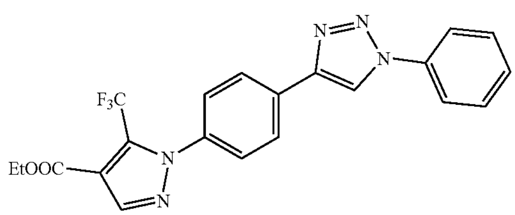 [SMILES: CCOC(=O)c1cnn(-c2ccc(-c3cn(-c4ccccc4)nn3)cc2)c1C(F)(F)F] |
| ethyl 1-(4-(1-(4-methoxyphenyl)-1H-1,2,3-triazol-4-yl)phenyl)-5-(trifluoromethyl)-1H-pyrazole-4-carboxylate | 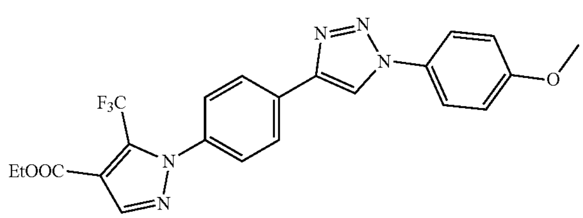 [SMILES: CCOC(=O)c1cnn(-c2ccc(-c3cn(-c4ccc(OC)cc4)nn3)cc2)c1C(F)(F)F] |
| ethyl 1-(4-(1-(3,5-dimethoxyphenyl)-1H-1,2,3-triazol-4-yl)phenyl)-5-(trifluoromethyl)-1H-pyrazole-4-carboxylate | 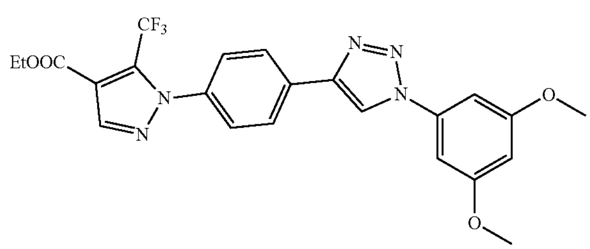 [SMILES: CCOC(=O)c1cnn(-c2ccc(-c3cn(-c4cc(OC)cc(OC)c4)nn3)cc2)c1C(F)(F)F] |
| 4-(4-(4-(ethoxycarbonyl)-5-(tiifluoromethyl)-1H-pyrazol-1-yl)phenyl)-1H-1,2,3-triazol-1-yl)butanoic acid | |
| ethyl 1-(4-(1-(4-aminophenyl)-1H-1,2,3-triazol-4-yl)phenyl)-5-(trifluoromethyl)-1H-pyrazole-4-carboxylate | 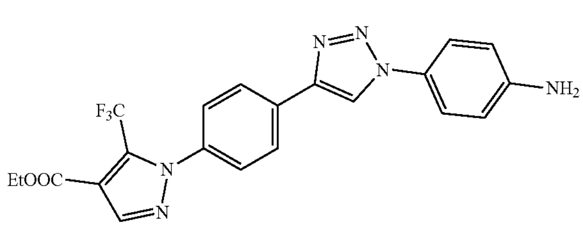 [SMILES: CCOC(=O)c1cnn(-c2ccc(-c3cn(-c4ccc(N)cc4)nn3)cc2)c1C(F)(F)F] |

TABLE 1-continued

| Name | Structure |
|---|---|
| ethyl 1-(4-(1-(3-hydroxyphenyl)-1H-1,2,3-triazol-4-yl)phenyl)-5-(trifluoromethyl)-1H-pyrazole-4-carboxylate | 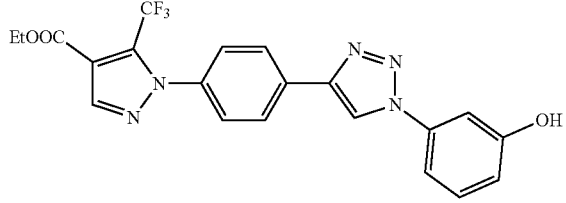 [SMILES: CCOC(=O)c1cnn(-c2ccc(-c3cn(-c4cccc(O)c4)nn3)cc2)c1C(F)(F)F] |
| ethyl 1-(4-(1-(4-chlorophenyl)-1H-1,2,3-triazol-4-yl)phenyl)-5-(trifluoromethyl)-1H-pyrazole-4-carboxylate | 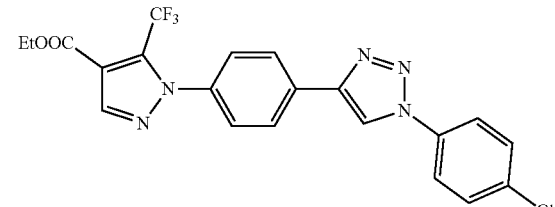 |
| ethyl 1-(4-(1-(3-aminophenyl)-1H-1,2,3-triazol-4-yl)phenyl)-5-(trifluoromethyl)-1H-pyrazole-4-carboxylate | 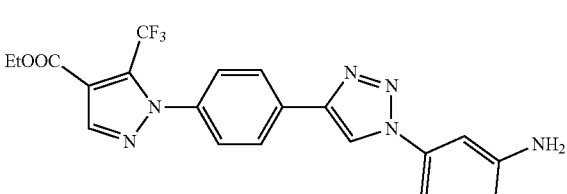 |
| ethyl 1-(4-(1-(pyridin-3-yl)-1H-1,2,3-triazol-4-yl)phenyl)-5-(ttifluoromethyl)-1H-pyrazole-4-carboxylate | 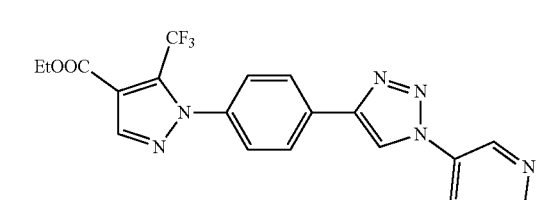 |
| ethyl 1-(4-(1-(3-fluoropyridin-4-yl)-1H-1,2,3-triazol-4-yl)phenyl)-5-(trifluoromethyl)-1H-pyrazole-4-carboxylate | 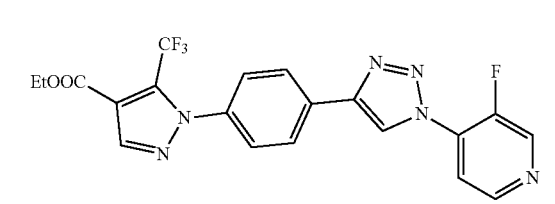 [SMILES: CCOC(=O)c1cnn(-c2ccc(-c3cn(-c4ccncc4F)nn3)cc2)c1C(F)(F)F] |
| ethyl 1-(4-(1-(pyridin-2-yl)-1H-1,2,3-triazol-4-yl)phenyl)-5-(ttifluoromethyl)-1H-pyrazole-4-carboxylate | 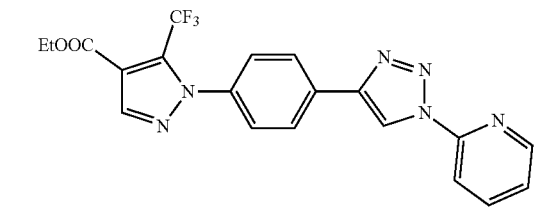 [SMILES: CCOC(=O)c1cnn(-c2ccc(-c3cn(-c4ccccn4)nn3)cc2)c1C(F)(F)F] |
| ethyl 1-(4-(1-(pyridin-4-yl)-1H-1,2,3-triazol-4-yl)phenyl)-5-(trifluoromethyl)-1H-pyrazole-4-carboxylate | 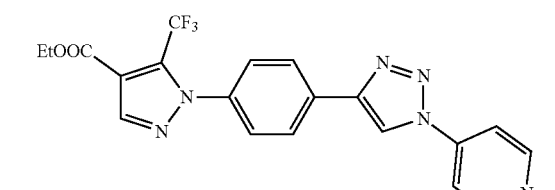 |

TABLE 1-continued

| Name | Structure |
|---|---|
| ethyl 1-(4-(1-(3,4-dimethoxyphenyl)-1H-1,2,3-triazol-4-yl)phenyl)-5-(trifluoromethyl)-1H-pyrazole-4-carboxylate | 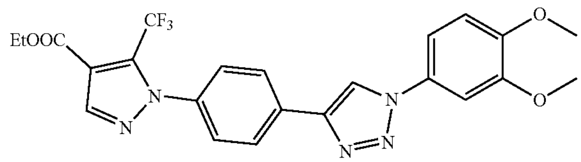 [SMILES: CCOC(=O)c1cnn(-c2ccc(-c3cn(-c4ccc(OC)c(OC)c4)nn3)cc2)c1C(F)(F)F] |
| ethyl 1-(4-(1-(4-hydroxy-3-methoxyphenyl)-1H-1,2,3-triazol-4-yl)phenyl)-5-(trifluoromethyl)-1H-pyrazole-4-carboxylate | 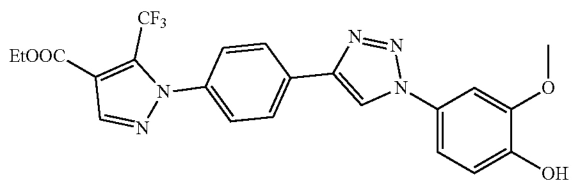 [SMILES: CCOC(=O)c1cnn(-c2ccc(-c3cn(-c4ccc(O)c(OC)c4)nn3)cc2)c1C(F)(F)F] |
| ethyl 1-(4-(1-(3-methoxyphenyl)-1H-1,2,3-triazol-4-yl)phenyl)-5-(trifluoromethyl)-1H-pyrazole-4-carboxylate | 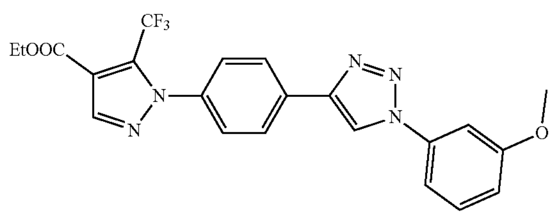 [SMILES: CCOC(=O)c1cnn(-c2ccc(-c3cn(-c4cccc(OC)c4)nn3)cc2)c1C(F)(F)F] |
| ethyl 1-(4-(1-(4-acetamidophenyl)-1H-1,2,3-triazol-4-yl)phenyl)-5-(trifluoromethyl)-1H-pyrazole-4-carboxylate | 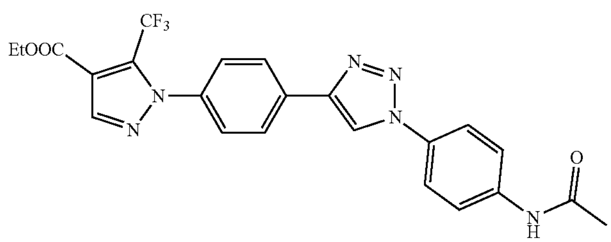 [SMILES: CCOC(=O)c1cnn(-c2ccc(-c3cn(-c4ccc(NC(C)=O)cc4)nn3)cc2)c1C(F)(F)F] |
| ethyl 1-(4-(1-(3-acetamidophenyl)-1H-1,2,3-triazol-4-yl)phenyl)-5-(trifluoromethyl)-1H-pyrazole-4-carboxylate | 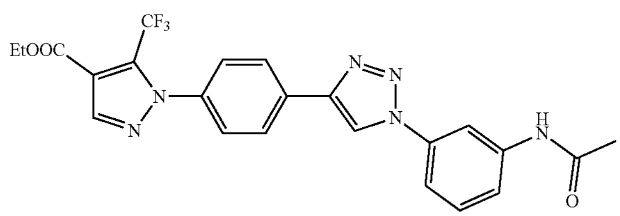 [SMILES: CCOC(=O)c1cnn(-c2ccc(-c3cn(-c4cccc(NC(C)=O)c4)nn3)cc2)c1C(F)(F)F] |
| ethyl 1-(4-(1-(2-acetamidophenyl)-1H-1,2,3-tnazol-4-yl)phenyl)-5-(tiifluoromethyl)-1H-pyrazole-4-carboxylate | 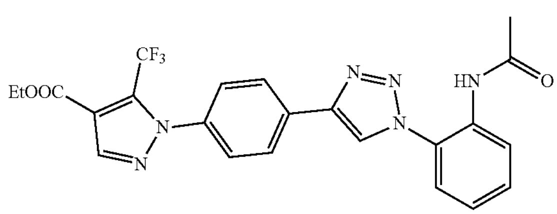 [SMILES: CCOC(=O)c1cnn(-c2ccc(-c3cn(-c4ccccc4NC(C)=O)nn3)cc2)c1C(F)(F)F] |
| 3-(4-(4-(4-(ethoxycarbonyl)-5-(trifluoromethyl)-1H-pyrazol-1-yl)phenyl)-1H-1,2,3-triazol-1-yl)benzoic acid | 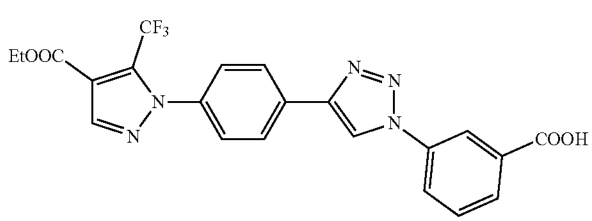 [SMILES: CCOC(=O)c1cnn(-c2ccc(-c3cn(-c4cccc(C(=O)O)c4)nn3)cc2)c1C(F)(F)F] |

TABLE 1-continued

| Name | Structure |
|---|---|
| 4-(4-(4-(4-(ethoxycarbonyl)-5-(trifluoromethyl)-1H-pyrazol-1-yl)phenyl)-1H-1,2,3-triazol-1-yl)benzoic acid | 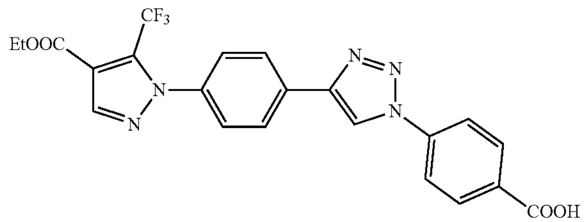 [SMILES: CCOC(=O)c1cnn(-c2ccc(-c3cn(-c4ccc(C(=O)O)cc4)nn3)cc2)c1C(F)(F)F] |
| ethyl 1-(4-(1-(4-phenoxyphenyl)-1H-1,2,3-triazol-4-yl)phenyl)-5-(trifluoromethyl)-1H-pyrazole-4-carboxylate | 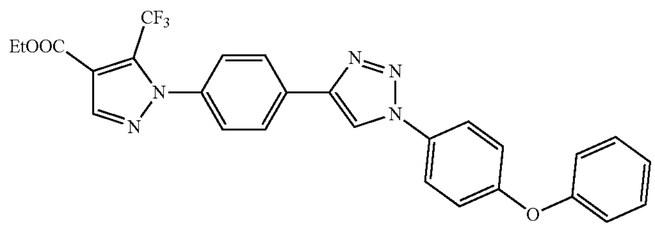 [SMILES: CCOC(=O)c1cnn(-c2ccc(-c3cn(-c4ccc(Oc5ccccc5)cc4)nn3)cc2)c1C(F)(F)F] |
| 4-(4-(3,5-bis(trifluoromethyl)-1H-pyrazol-1-yl)phenyl)-1-phenyl-1H-1,2,3-triazole | 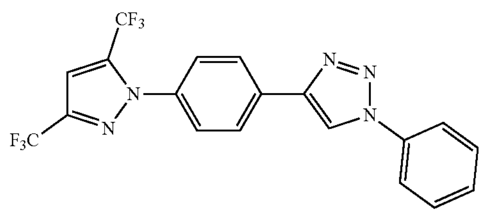 [SMILES: FC(F)(F)c1cc(C(F)(F)F)n(-c2ccc(-c3cn(-c4ccccc4)nn3)cc2)n1] |
| 4-(4-(3,5-bis(trifluoromethyl)-1H-pyrazol-1-yl)phenyl)-1-(4-methoxyphenyl)-1H-1,2,3-triazole | 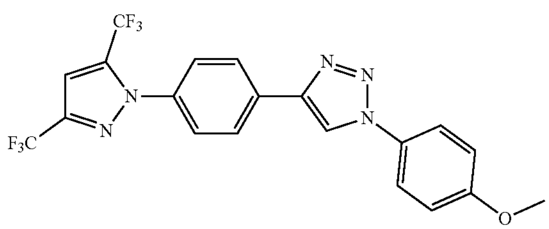 [SMILES: COc1ccc(-n2cc(-c3ccc(-n4nc(C(F)(F)F)cc4C(F)(F)F)cc3)nn2)cc1] |
| 4-(4-(3,5-bis(trifluoromethyl)-1H-pyrazol-1-yl)phenyl)-1-(3,5-dimethoxyphenyl)-1H-1,2,3-triazole | 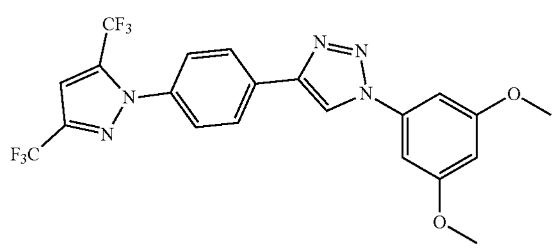 [SMILES: COc1cc(OC)cc(-n2cc(-c3ccc(-n4nc(C(F)(F)F)cc4C(F)(F)F)cc3)nn2)c1] |
| 4-(4-(4-(3,5-bis(tiifluoromethyl)-1H-pyrazol-1-yl)phenyl)-1H-1,2,3-triazol-1-yl)butanoic acid | 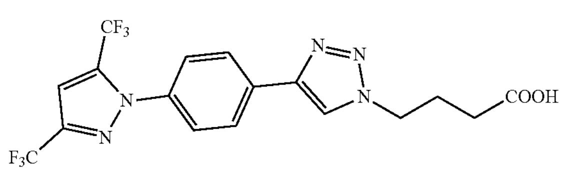 [SMILES: O=C(O)CCCn1cc(-c2ccc(-n3nc(C(F)(F)F)cc3C(F)(F)F)cc2)nn1] |
| 4-(4-(4-(3,5-bis(tiifluoromethyl)-1H-pyrazol-1-yl)phenyl)-1H-1,2,3-triazol-1-yl)aniline | 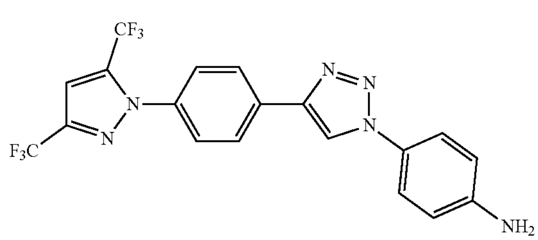 [SMILES: Nc1ccc(-n2cc(-c3ccc(-n4nc(C(F)(F)F)cc4C(F)(F)F)cc3)nn2)cc1] |

TABLE 1-continued

| Name | Structure |
|---|---|
| 3-(5-(4-(3,5-bis(trifluoromethyl)-1H-pyrazol-1-yl)phenyl)-3H-pyrazol-3-yl)phenol | 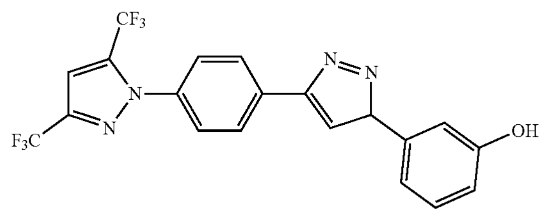 [SMILES: Oc1cccc(C2C=C(c3ccc(-n4nc(C(F)(F)F)cc4C(F)(F)F)cc3)N=N2)c1] |
| 4-(4-(3,5-bis(trifluoromethyl)-1H-pyrazol-1-yl)phenyl)-1-(4-chlorophenyl)-1H-1,2,3-triazole | 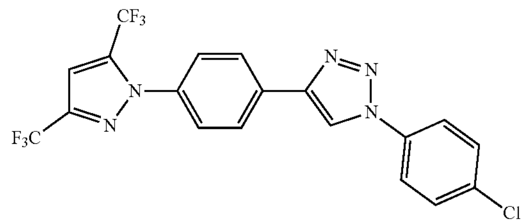 [SMILES: FC(F)(F)c1cc(C(F)(F)F)n(-c2ccc(-c3cn(-c4ccc(Cl)cc4)nn3)cc2)n1] |
| 3-(4-(4-(3,5-bis(difluoromethyl)-1H-pyrazol-1-yl)phenyl)-1H-1,2,3-triazol-1-yl)aniline | 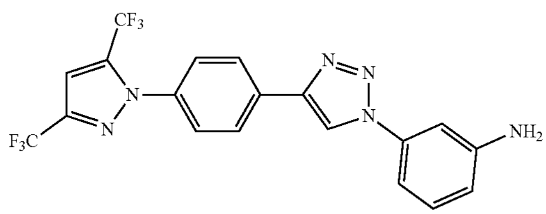 [SMILES: Nc1cccc(-n2cc(-c3ccc(-n4nc(C(F)(F)F)cc4C(F)(F)F)cc3)nn2)c1] |
| 3-(4-(4-(3,5-bis(trifluoromethyl)-1H-pyrazol-1-yl)phenyl)-1H-1,2,3-triazol-1-yl)pyridine | 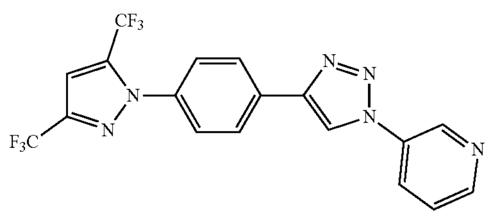 [SMILES: FC(F)(F)c1cc(C(F)(F)F)n(-c2ccc(-c3cn(-c4cccnc4)nn3)cc2)n1] |
| 4-(4-(4-(3,5-bis(trifluoromethyl)-1H-pyrazol-1-yl)phenyl)-1H-1,2,3-triazol-1-yl)-3-fluoropyridine | 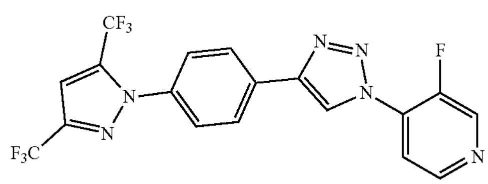 [SMILES: Fc1cnccc1-n1cc(-c2ccc(-n3nc(C(F)(F)F)cc3C(F)(F)F)cc2)nn1] |
| 2-(4-(4-(3,5-bis(trifluoromethyl)-1H-pyrazol-1-yl)phenyl)-1H-1,2,3-triazol-1-yl)pyridine | 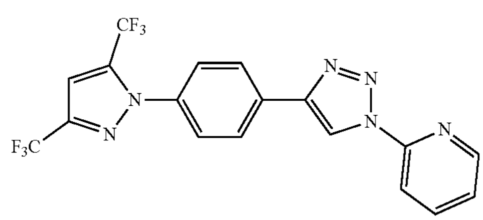 [SMILES: FC(F)(F)c1cc(C(F)(F)F)n(-c2ccc(-c3cn(-c4ccccn4)nn3)cc2)n1] |
| 4-(4-(4-(3,5-bis(trifluoromethyl)-1H-pyrazol-1-yl)phenyl)-1H-1,2,3-triazol-1-yl)pyridine | 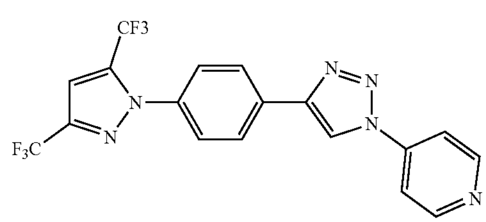 [SMILES: FC(F)(F)c1cc(C(F)(F)F)n(-c2ccc(-c3cn(-c4ccncc4)nn3)cc2)n1] |

TABLE 1-continued

| Name | Structure |
| --- | --- |
| 4-(4-(3,5-bis(trifluoromethyl)-1H-pyrazol-1-yl)phenyl)-1-(3,4-dimethoxyphenyl)-1H-1,2,3-triazole | 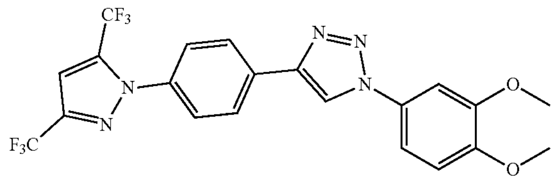 [SMILES: COc1ccc(-n2cc(-c3ccc(-n4nc(C(F)(F)F)cc4C(F)(F)F)cc3)nn2)cc1OC] |
| 4-(4-(4-(3,5-bis(trifluoromethyl)-1H-pyrazol-1-yl)phenyl)-1H-1,2,3-triazol-1-yl)-2-methoxyphenol | 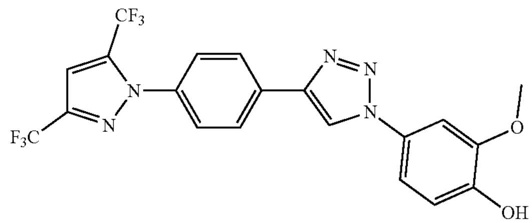 [SMILES: COc1cc(-n2cc(-c3ccc(-n4nc(C(F)(F)F)cc4C(F)(F)F)cc3)nn2)ccc1O] |
| 4-(4-(3,5-bis(trifluoromethyl)-1H-pyrazol-1-yl)phenyl)-1-(3-methoxyphenyl)-1H-1,2,3-triazole | 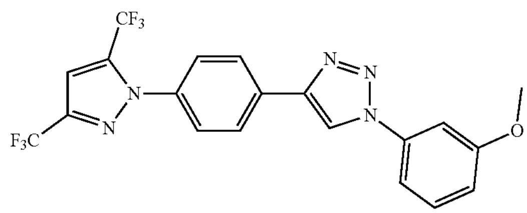 [SMILES: COc1cccc(-n2cc(-c3ccc(-n4nc(C(F)(F)F)cc4C(F)(F)F)cc3)nn2)c1] |
| N-(4-(4-(4-(3,5-bis(trifluoromethyl)-1H-pyrazol-1-yl)phenyl)-1H-1,2,3-triazol-1-yl)phenyl)acetamide | 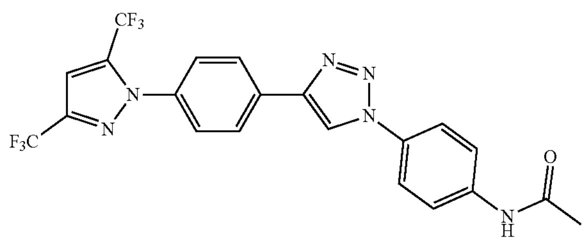 [SMILES: CC(=O)Nc1ccc(-n2cc(-c3ccc(-n4nc(C(F)(F)F)cc4C(F)(F)F)cc3)nn2)cc1] |
| N-(3-(4-(4-(3,5-bis(trifluoromethyl)-1H-pyrazol-1-yl)phenyl)-1H-1,2,3-triazol-1-yl)phenyl)acetamide | 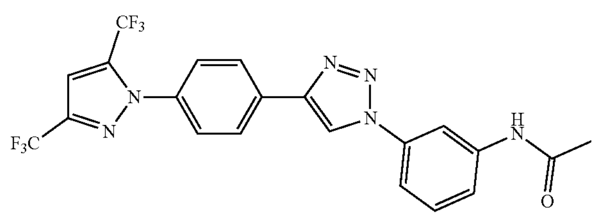 [SMILES: CC(=O)Nc1cccc(-n2cc(-c3ccc(-n4nc(C(F)(F)F)cc4C(F)(F)F)cc3)nn2)c1] |
| 3-(4-(4-(3,5-bis(trifluoromethyl)-1H-pyrazol-1-yl)phenyl)-1H-1,2,3-triazol-1-yl)benzoic acid | 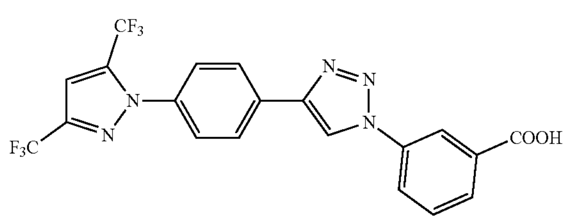 [SMILES: O=C(O)c1cccc(-n2cc(-c3ccc(-n4nc(C(F)(F)F)cc4C(F)(F)F)cc3)nn2)c1] |
| 4-(4-(4-(3,5-bis(trifluoromethyl)-1H-pyrazol-1-yl)phenyl)-1H-1,2,3-triazol-1-yl)benzoic acid | 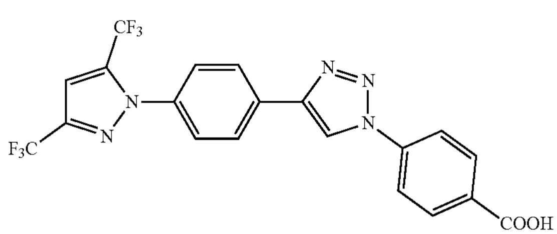 [SMILES: O=C(O)c1ccc(-n2cc(-c3ccc(-n4nc(C(F)(F)F)cc4C(F)(F)F)cc3)nn2)cc1] |

TABLE 1-continued

| Name | Structure |
|---|---|
| 4-(4-(3,5-bis(trifluoromethyl)-1H-pyrazol-1-yl)phenyl)-1-(4-phenoxyphenyl)-1H-1,2,3-triazole | 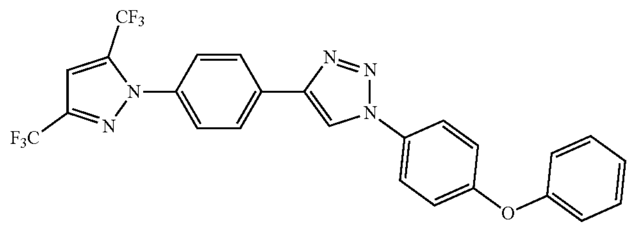 [SMILES: FC(F)(F)c1cc(C(F)(F)F)n(-c2ccc(-c3cn(-c4ccc(Oc5ccccc5)cc4)nn3)cc2)n1] |
| ethyl 1-(4-(4-(3-carbamoylphenyl)-1H-1,2,3-triazol-1-yl)phenyl)-5-(trifluoromethyl)-1H-pyrazole-4-carboxylate | 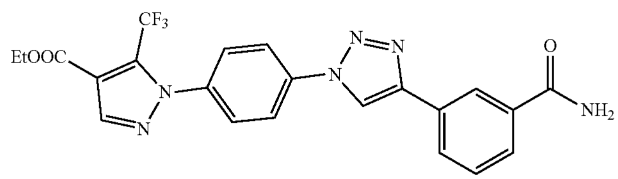 [SMILES: CCOC(=O)c1cnn(-c2ccc(-n3cc(-c4cccc(C(N)=O)c4)nn3)cc2)c1C(F)(F)F] |
| ethyl 1-(4-(4-(3-(methoxycarbonyl)phenyl)-1H-1,2,3-triazol-1-yl)phenyl)-5-(trifluoromethyl)-1H-pyrazole-4-carboxylate | 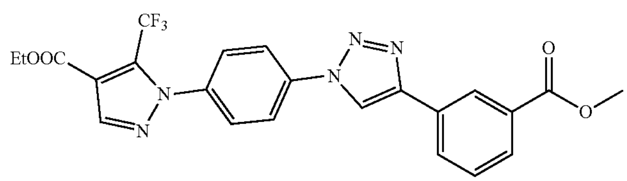 [SMILES: CCOC(=O)c1cnn(-c2ccc(-n3cc(-c4cccc(C(=O)OC)c4)nn3)cc2)c1C(F)(F)F] |
| ethyl 1-(4-(4-(3-sulfamoylphenyl)-1H-1,2,3-triazol-1-yl)phenyl)-5-(trifluoromethyl)-1H-pyrazole-4-carboxylate | 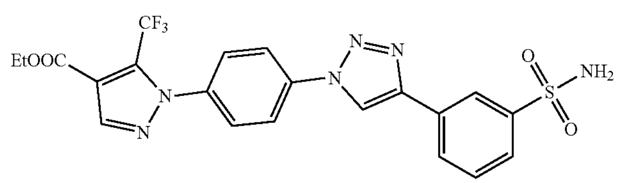 [SMILES: CCOC(=O)c1cnn(-c2ccc(-n3cc(-c4cccc(S(N)(=O)=O)c4)nn3)cc2)c1C(F)(F)F] |
| methyl 1-(4-(1-(4-chlorophenyl)-1H-1,2,3-triazol-4-yl)phenyl)-5-(trifluoromethyl)-1H-pyrazole-4-carboxylate | 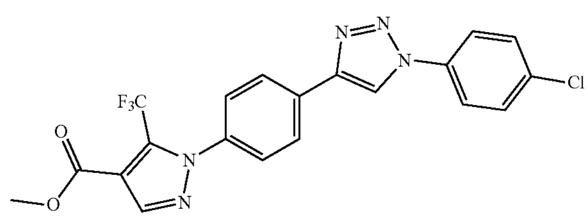 [SMILES: COC(=O)c1cnn(-c2ccc(-c3cn(-c4ccc(Cl)cc4)nn3)cc2)c1C(F)(F)F] |
| tert-butyl 1-(4-(1-(4-chlorophenyl)-1H-1,2,3-triazol-4-yl)phenyl)-5-(trifluoromethyl)-1H-pyrazole-4-carboxylate | 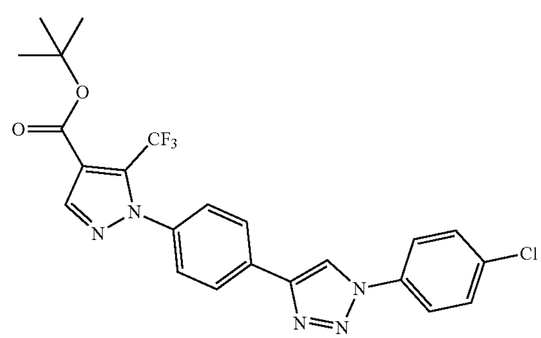 [SMILES: CC(C)(C)OC(=O)c1cnn(-c2ccc(-c3cn(-c4ccc(Cl)cc4)nn3)cc2)c1C(F)(F)F] |

TABLE 1-continued

| Name | Structure |
|---|---|
| isopropyl 1-(4-(1-(4-chlorophenyl)-1H-1,2,3-triazol-4-yl)phenyl)-5-(tiifluoromethyl)-1H-pyrazole-4-carboxylate | 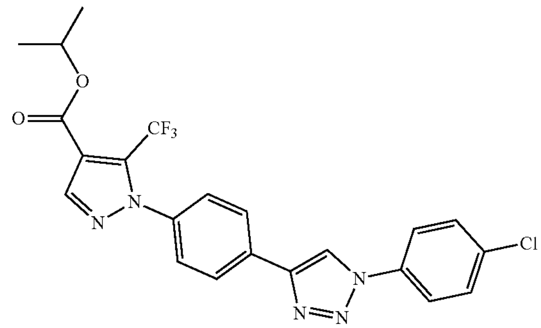 [SMILES: CC(C)OC(=O)c1cnn(-c2ccc(-c3cn(-c4ccc(Cl)cc4)nn3)cc2)c1C(F)(F)F] |
| 1-(4-(1-(4-chlorophenyl)-1H-1,2,3-triazol-4-yl)phenyl)-5-(trifluoromethyl)-1H-pyrazole-4-carboxylic acid | 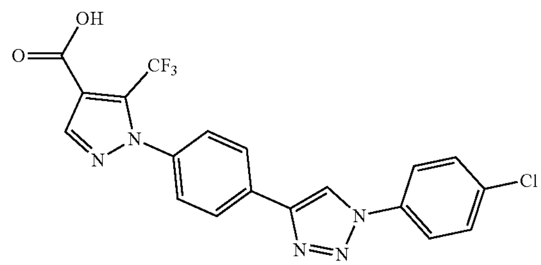 [SMILES: O=C(O)c1cnn(-c2ccc(-c3cn(-c4ccc(Cl)cc4)nn3)cc2)c1C(F)(F)F] |
| 3-(1-(4-(4-(methoxycarbonyl)-5-(trifluoromethyl)-1H-pyrazol-1-yl)phenyl)-1H-1,2,3-triazol-4-yl)benzoic acid | 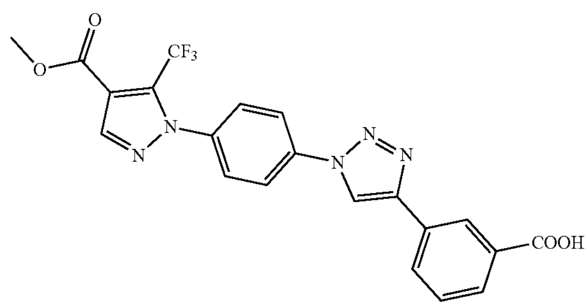 [SMILES: COC(=O)c1cnn(-c2ccc(-n3cc(-c4cccc(C(=O)O)c4)nn3)cc2)c1C(F)(F)F] |
| 3-(1-(4-(4-(isopropoxycarbonyl)-5-(trifluoromethyl)-1H-pyrazol-1-yl)phenyl)-1H-1,2,3-triazol-4-yl)benzoic acid | 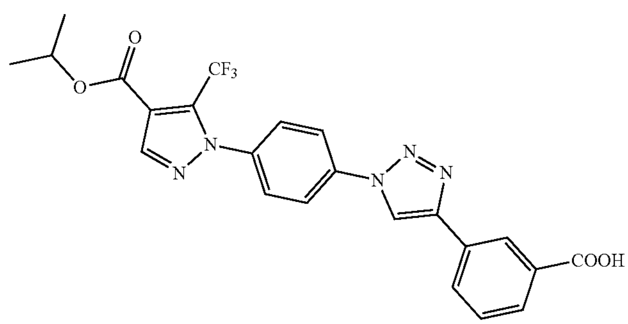 [SMILES: CC(C)OC(=O)c1cnn(-c2ccc(-n3cc(-c4cccc(C(=O)O)c4)nn3)cc2)c1C(F)(F)F] |
| 3-(1-(4-(4-((pentan-2-yloxy)carbonyl)-5-(trifluoromethyl)-1H-pyrazol-1-yl)phenyl)-1H-1,2,3-triazol-4-yl)benzoic acid | 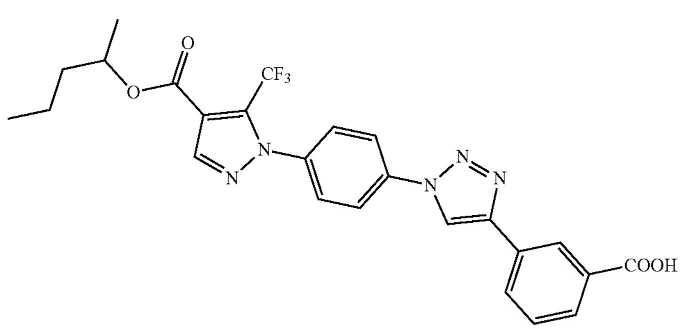 [SMILES: CCCC(C)OC(=O)c1cnn(-c2ccc(-n3cc(-c4cccc(C(=O)O)c4)nn3)cc2)c1C(F)(F)F] |

TABLE 1-continued

| Name | Structure |
|---|---|
| 3-(1-(4-(4-((pyridin-4-ylmethoxy)carbonyl)-5-(trifluoromethyl)-1H-pyrazol-1-yl)phenyl)-1H-1,2,3-triazol-4-yl)benzoic acid | 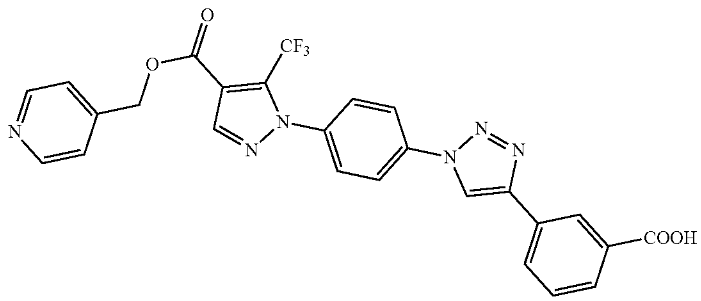 [SMILES: O=C(O)c1cccc(-c2cn(-c3ccc(-n4ncc(C(=O)OCc5ccncc5)c4C(F)(F)F)cc3)nn2)c1] |
| 3-(1-(4-(4-((benzyloxy)carbonyl)-5-(trifluoromethyl)-1H-pyrazol-1-yl)phenyl)-1H-1,2,3-triazol-4-yl)benzoic acid | 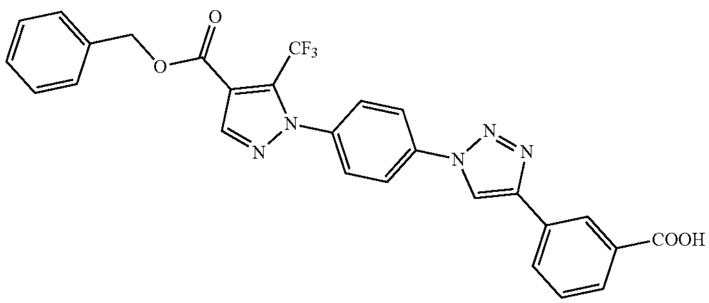 [SMILES: O=C(O)c1cccc(-c2cn(-c3ccc(-n4ncc(C(=O)OCc5ccccc5)c4C(F)(F)F)cc3)nn2)c1] |
| 3-(1-(4-(4-((2-morpholinoethoxy)carbonyl)-5-(trifluoromethyl)-1H-pyrazol-1-yl)phenyl)-1H-1,2,3-triazol-4-yl)benzoic acid | 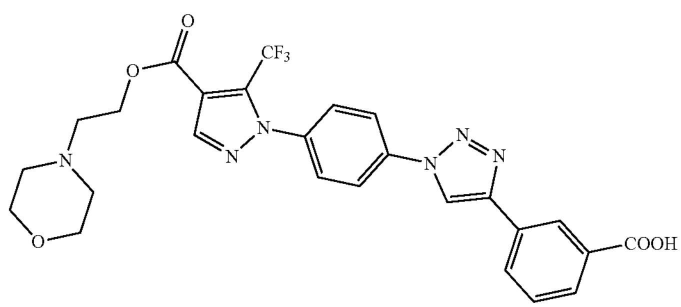 [SMILES: O=C(O)c1cccc(-c2cn(-c3ccc(-n4ncc(C(=O)OCCN5CCOCC5)c4C(F)(F)F)cc3)nn2)c1] |
| 3-(1-(4-(4-(((1,1,1,3,3,3-hexafluoro-2-methylpropan-2-yl)oxy)carbonyl)-5-(trifluoromethyl)-1H-pyrazol-1-yl)phenyl)-1H-1,2,3-triazol-4-yl)benzoic acid | 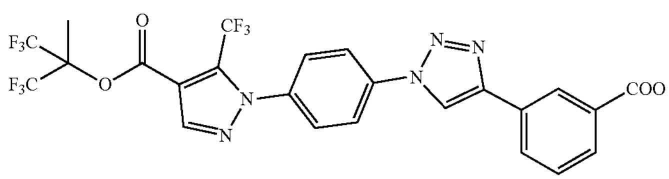 |
| 4-(1-(4-(4-(isopropoxycarbonyl)-5-(trifluoromethyl)-1H-pyrazol-1-yl)phenyl)-1H-1,2,3-triazol-4-yl)picolinic acid | 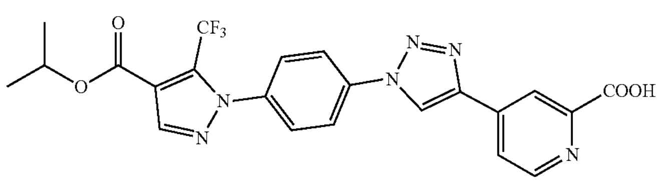 [SMILES: CC(C)OC(=O)c1cnn(-c2ccc(-n3cc(-c4ccnc(C(=O)O)c4)nn3)cc2)c1C(F)(F)F] |
| 2-(1-(4-(4-(isopropoxycarbonyl)-5-(trifluoromethyl)-1H-pyrazol-1-yl)phenyl)-1H-1,2,3-triazol-4-yl)isonicotinic acid | 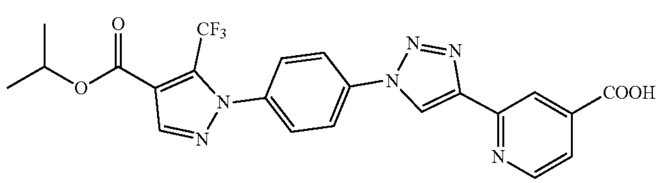 [SMILES: CC(C)OC(=O)c1cnn(-c2ccc(-n3cc(-c4cc(C(=O)O)ccn4)nn3)cc2)c1C(F)(F)F] |

TABLE 1-continued

| Name | Structure |
|---|---|
| 4-(1-(4-(4-(isopropoxycarbonyl)-5-(trifluoromethyl)-1H-pyrazol-1-yl)phenyl)-1H-1,2,3-triazol-4-yl)phthalic acid | 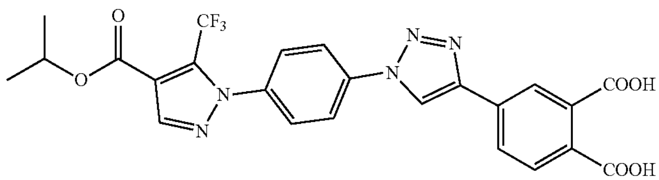 [SMILES: CC(C)OC(=O)c1cnn(-c2ccc(-n3cc(-c4ccc(C(=O)O)c(C(=O)O)c4)nn3)cc2)c1C(F)(F)F] |
| 2-amino-5-(1-(4-(4-(isopropoxycarbonyl)-5-(trifluoromethyl)-1H-pyrazol-1-yl)phenyl)-1H-1,2,3-triazol-4-yl)benzoic acid | 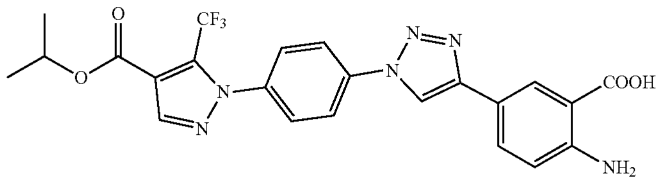 [SMILES: CC(C)OC(=O)c1cnn(-c2ccc(-n3cc(-c4ccc(N)c(C(=O)O)c4)nn3)cc2)c1C(F)(F)F] |
| 2-hydroxy-5-(1-(4-(4-(isopropoxycarbonyl)-5-(trifluoromethyl)-1H-pyrazol-1-yl)phenyl)-1H-1,2,3-triazol-4-yl)benzoic acid | 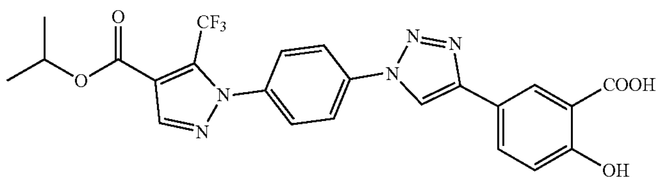 [SMILES: CC(C)OC(=O)c1cnn(-c2ccc(-n3cc(-c4ccc(O)c(C(=O)O)c4)nn3)cc2)c1C(F)(F)F] |

General Synthesis of Compounds of Formula (I)

The following schemes show a method for preparing the compounds of the present description. For a more detailed description of the individual reaction steps, see the Examples herein below. Those skilled in the art will appreciate that other synthetic routes may be used to synthesize the compounds of the invention. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Compounds of formula (I) display a 1,4-disubstituted triazole ring, which is synthesized via the azide-alkyne1,3-dipolar cycloaddition catalized by copper (I) generated in situ by sodium ascorbate (Angew. Chem. Int. Ed. 2002, 41, 2596).

In detail, compounds of formula (II)

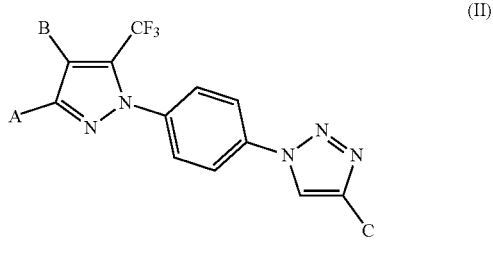

(II)

can be prepared as outlined in Scheme a below:

Scheme a

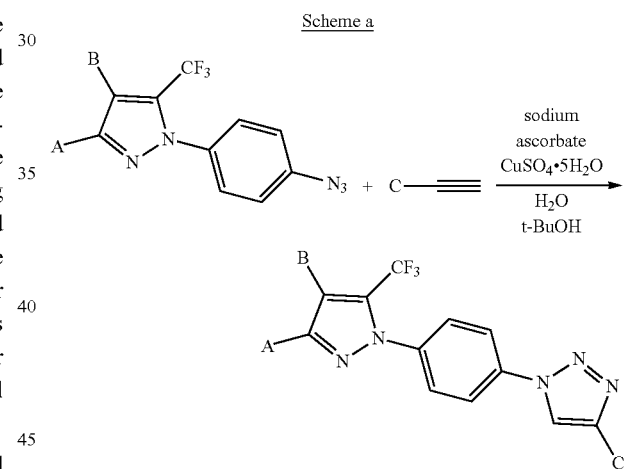

While the alkynes are prepared applying synthetic methodologies known in the art, the azides are prepared following the Scheme b, Scheme c or Scheme d below.

Condensation reaction between ethyl 2-ethoxymethylene-4,4,4-trifluoro-3-oxobutyrate and 4-nitrophenylhydrazine hydrochloride in DMF at 100° C. gives the pyrazole 1. Subsequent hydrogenation of the nitro group furnishes the intermediate 2. Last, a diazotation-azidation protocol gives the final azide 3.

Scheme b

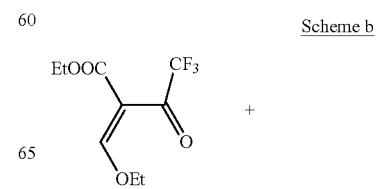

-continued

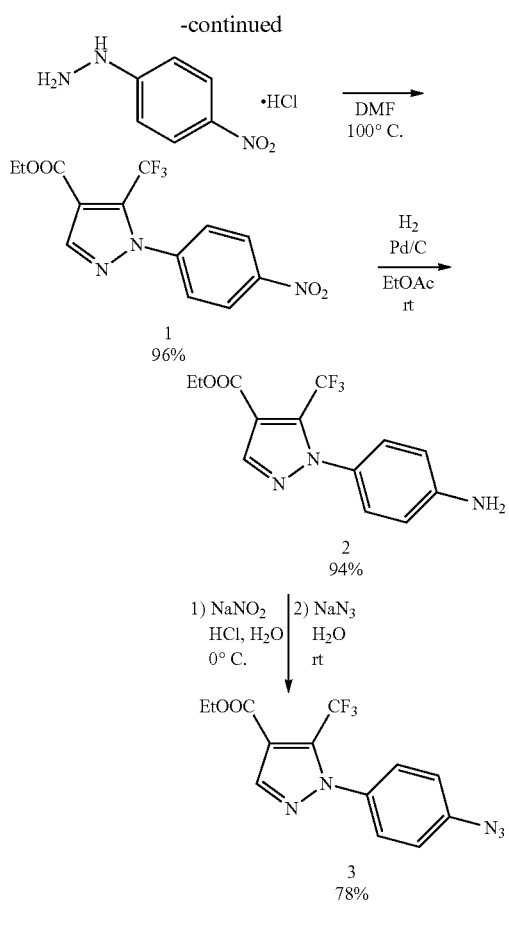

Ester groups in 4-position different from ethyl ester are prepared according to Scheme c. The ethyl ester of compound 3 is hydrolized to 4 and the resulting carboxylic acid is then coupled with different alcohols.

Scheme c

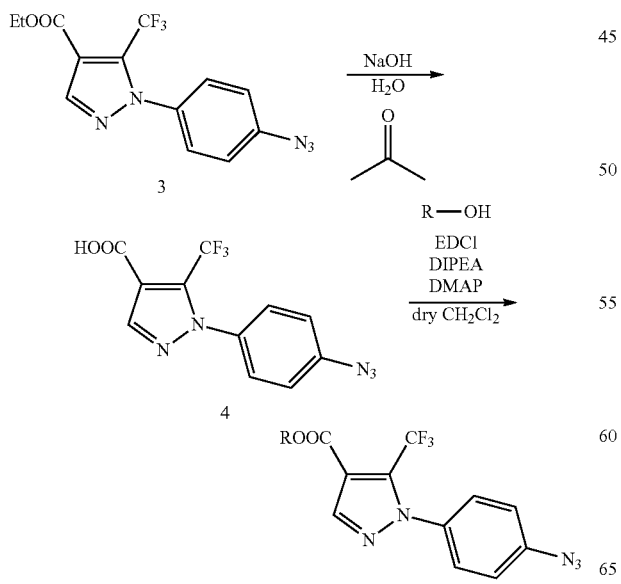

Condensation reaction between 1,1,1,5,5,5-hexafluoro-2,4-pentanedione and 4-nitrophenylhydrazine hydrochloride in DMF at 100° C. gives the intermediate 5. Treatment with hydrochloric acid 37% in boiling ethanol favors the dehydration/aromatization, leading to the pyrazole 6. Subsequent hydrogenation of the nitro group furnishes the intermediate 7. Last, a diazotation-azidation protocol gives the final azide 8.

Scheme d

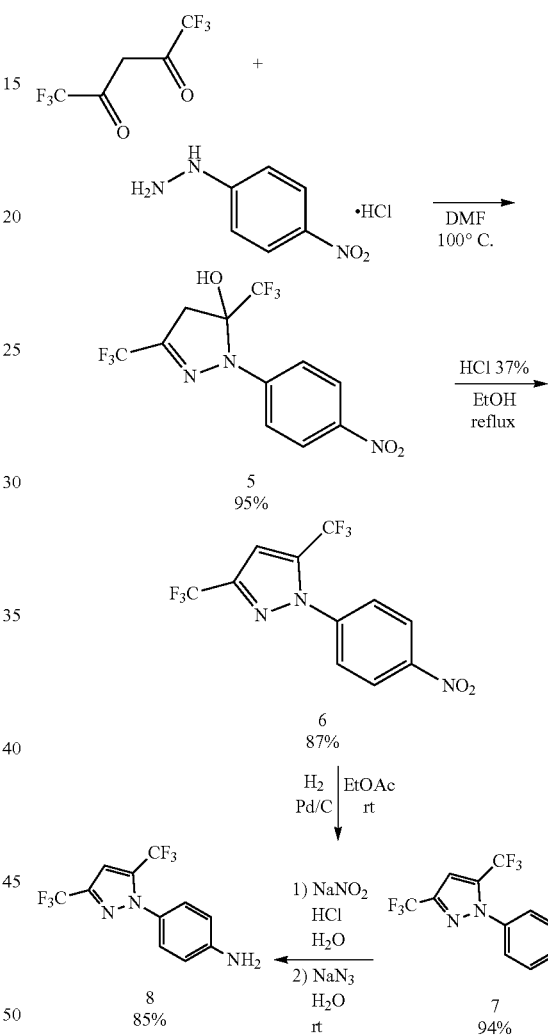

Compounds of Formula (III)

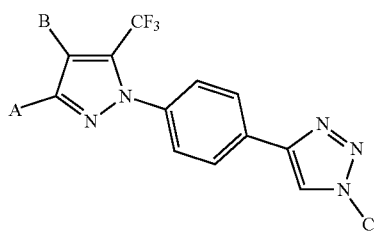

can be prepared as outlined in Scheme e below:

Scheme e

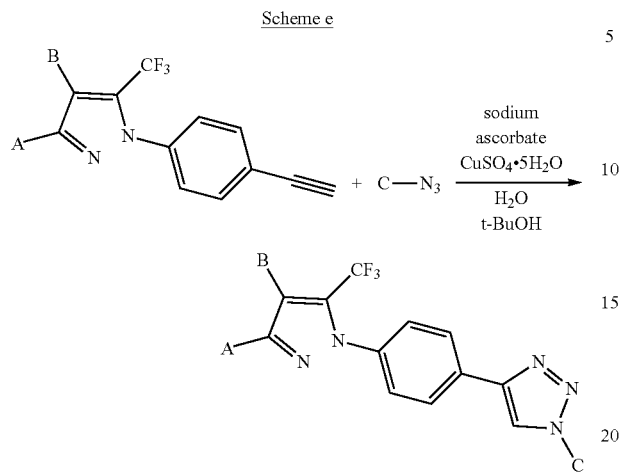

While azides are prepared applying synthetic methodologies known in the art, the alkynes are prepared following the Scheme f and Scheme g below.

Condensation reaction between ethyl 2-ethoxymethylene-4,4,4-trifluoro-3-oxobutyrate and 4-bromophenylhydrazine hydrochloride in DMF at 100° C. gives the pyrazole 9. Subsequent Sonogashira coupling of the bromide derivative with trimethyl silylacetylene leads to intermediate 10, which is deprotected with TBAF in THF to give the final alkyne 11.

Scheme f

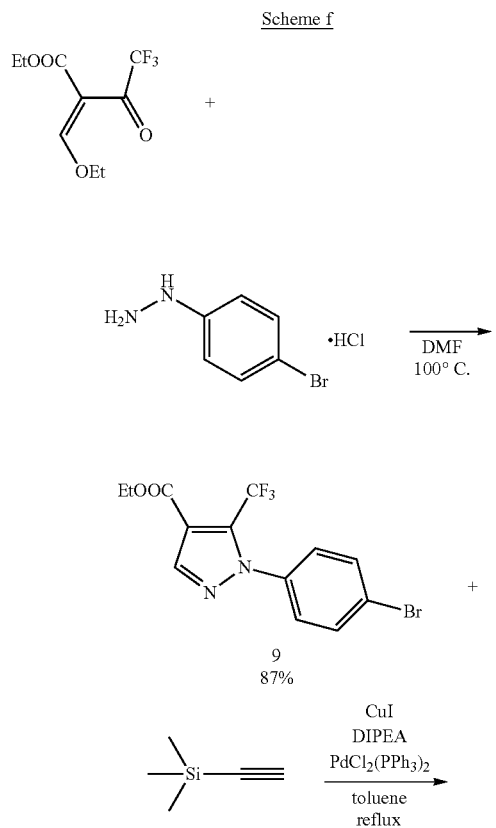

Condensation reaction between 1,1,1,5,5,5-hexafluoro-2,4-pentanedione and 4-bromophenylhydrazine hydrochloride in DMF at 100° C. gives the intermediate 12. Subsequent Sonogashira coupling of the bromide derivative with trimethyl silylacetylene leads to intermediate 13, which is deprotected with TBAF in THF to give the final alkyne 14.

Scheme g

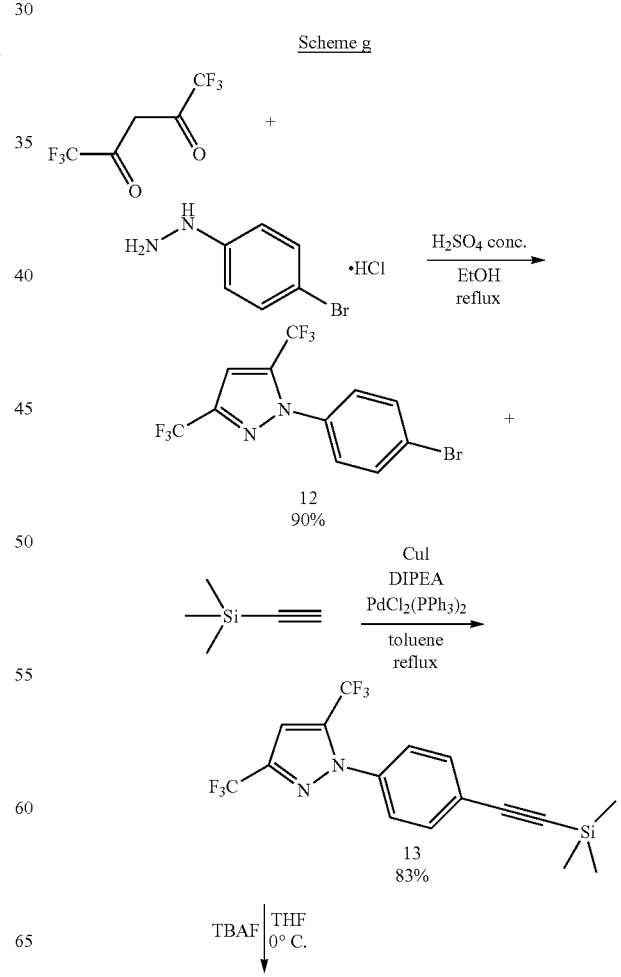

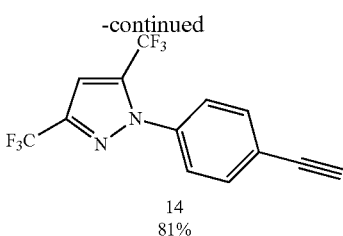

14
81%

The chemical reactions described in the Examples below may be readily adapted to prepare a number of other SOCE modulators of the invention, and alternative methods for preparing the compounds of this invention are deemed to be within the scope of this invention.

For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Example 1

Synthesis of ethyl 1-(4-nitrophenyl)-5-(trifluoromethyl)-1H-pyrazole-4-carboxylate (Intermediate 1)

To a solution of (4-nitrophenyl)hydrazine hydrochloride (2.00 g, 10.5 mmol) in DMF (20 mL) (E)-ethyl 2-(ethoxymethylene)-4,4,4-trifluoro-3-oxobutanoate is added. The resulting mixture is stirred at reflux for 2 hours. Then, diethyl ether is added and the organic layer is washed with water (×2), dried over sodium sulfate and evaporated to give compound 1 as a deep yellow solid (3.34 g, 10.2 mmol, 96%).

Analytical Data:
$^1$H-NMR (300 MHz, CDCl$_3$): δ 8.39 (d, J 8.8 Hz, 2H), 8.16 (s, 1H), 7.66 (d, J 8.8 Hz, 2H), 4.38 (q, J 7.1 Hz, 2H), 1.38 (t, J 7.1 Hz, 3H). MS: M+1 330

Example 2

Synthesis of ethyl 1-(4-aminophenyl)-5-(trifluoromethyl)-1H-pyrazole-4-carboxylate (Intermediate 2)

EtOAc (30 mL), Pd/C (0.90 g) and ethyl 1-(4-nitrophenyl)-5-(trifluoromethyl)-1H-pyrazole-4-carboxylate (3.00 g, 9.12 mmol) are added under hydrogen atmosphere. After stirring at room temperature for 2 hours, the resulting mixture is filtered under vacuo over a pad of celite, rinsed with EtOAc and evaporated to give compound 2 as a yellow solid (2.56 g, 8.56 mmol, 94%).

Analytical Data:
$^1$H-NMR (300 MHz, CDCl$_3$): δ 8.06 (s, 1H), 7.17 (d, J 8.5 Hz, 2H), 6.72 (d, J 8.5 Hz, 2H), 4.37 (q, J 7.1 Hz, 2H), 3.19 (br s, 2H), 1.397 (t, J 7.1 Hz, 3H). MS: M+1 300

Example 3

Synthesis of ethyl 1-(4-azidophenyl)-5-(trifluoromethyl)-1H-pyrazole-4-carboxylate (Intermediate 3)

To a suspension of ethyl 1-(4-aminophenyl)-5-(trifluoromethyl)-1H-pyrazole-4-carboxylate (2.6 g, 8.70 mmol) in water (40.7 mL) HCl 37% (3.3 mL) is added. The resulting mixture is cooled down at 0° C. and a solution of NaNO$_2$ (0.57 g, 8.26 mmol) in water (3.9 mL) is added. After 10 minutes a solution of NaN$_3$ (0.64 g, 9.85 mmol) in water (3.9 mL) is added and the reaction is left to reach at room temperature and stirred for 1 hour. The mixture is worked up by dilution with EtOAc and washing with water (×1). The organic layer is dried over sodium sulfate and evaporated yielding compound 3 as a pale red oil (2.20 g, 6.77 mmol, 78%).

Analytical Data:
$^1$H-NMR (300 MHz, CDCl$_3$): δ 8.08 (s, 1H), 7.39 (d, J 8.5 Hz, 2H), 7.11 (d, J 8.5 Hz, 2H), 4.35 (q, J 7.1 Hz, 2H), 1.37 (t, J 7.1 Hz, 3H). MS: M+1 326

Example 4

Synthesis of 1-(4-azidophenyl)-5-(trifluoromethyl)-H-pyrazole-4-carboxylic acid (Intermediate 4)

To a solution ethyl 1-(4-azidophenyl)-5-(trifluoromethyl)-1H-pyrazole-4-carboxylate (0.19 mmol, 1 eq) in acetone (1 mL) and water (1 mL), NaOH (0.38 mmol, 2 eq) is added. The resulting mixture is left to react overnight at room temperature and after is heated at reflux for 2 hours. Then, the volatile is removed under vacuo and the solution is acidified with HCl 3N until pH 4, diluted with water and extracted with EtOAc (×1). The crude material is purified by column chromatography using petroleum ether/ethyl acetate 8:2, petroleum ether/ethyl acetate 7:3, petroleum ether/ethyl acetate 6:4 and petroleum ether/ethyl acetate 5:5 (+HCOOH 1%), yielding compound 4 as a white solid (84%).

Analytical Data:
$^1$H-NMR (300 MHz, CDCl$_3$): δ 8.20 (s, 1H), 7.43 (d, J 8.8 Hz, 2H), 7.15 (d, J 8.8 Hz, 2H).

Example 5

Synthesis of methyl 1-(4-azidophenyl)-5-(trifluoromethyl)-1H-pyrazole-4-carboxylate To a solution of (1 eq, 0.48 mmol) 1-(4-azidophenyl)-5-(trifluoromethyl)-1H-pyrazole-4-carboxylate in dry dichloromethane alcohol (1 eq), EDCl (2 eq), DIPEA (3 eq) and DMAP (0.5 eq) are added. The resulting mixture is stirred at room temperature overnight. The reaction is worked up by diluition with CH$_2$Cl$_2$ and washing with water (×2). After drying over sodium sulfate and evaporation of the solvent the crude product is purified by column chromatography using petroleum ether/ethyl acetate 8:2 and petroleum ether/ethyl acetate 7:3 as eluent, yielding compound 5 as a brown oil (87%).

Analytical Data:
$^1$H-NMR (300 MHz, CDCl$_3$): δ 8.05 (s, 1H), 7.36 (d, J 8.3 Hz, 2H), 7.08 (d, J 8.3 Hz, 2H), 3.85 (s, 3H).

Example 6

Synthesis of isopropyl 1-(4-azidophenyl)-5-(trifluoromethyl)-H-pyrazole-4-carboxylate The title compound was synthesized following the procedure described for Example 5. The crude product is subjected to chromatography column with petroleum ether/ethyl acetate 8:2 and petroleum ether/ethyl acetate 7:3 as eluent, yielding compound 6 as a yellow oil (66%).

Analytical Data:
¹H-NMR (300 MHz, CDCl₃): δ 8.07 (s, 1H), 7.38 (d, J 8.5 Hz, 2H), 7.11 (d, J 8.5 Hz, 2H), 5.22 (ept, J 6.0 Hz, 1H), 1.34 (d, J 6.0 Hz, 6H).

Example 7

Synthesis of pentan-2-yl 1-(4-azidophenyl)-5-(trifluoromethyl)-1H-pyrazole-4-carboxylate The title compound was synthesized following the procedure described for Example 5. The crude product is subjected to chromatography column with petroleum ether/ethyl acetate 98:2 as eluent, yielding compound 7 as a white solid (27%).
Analytical Data:
¹H-NMR (300 MHz, CDCl₃): δ 8.07 (s, 1H), 7.38 (d, J=8.5 Hz, 2H), 7.11 (d, J=8.5 Hz, 2H), 5.14 (s, J=6.3 Hz, 1H), 1.78-1.63 (m, 1H), 1.52-1.60 (m, 1H), 1.36-1.18 (m, 5H), 0.92 (t, J=7.2 Hz, 3H).

Example 8

Synthesis of pyridin-4-ylmethyl 1-(4-azidophenyl)-5-(trifluoromethyl)-1H-pyrazole-4-carboxylate The title compound was synthesized following the procedure described for Example 5. The crude product is subjected to chromatography column with petroleum ether/ethyl acetate 9:1, petroleum ether/ethyl acetate 8:2 and petroleum ether/ethyl acetate 7:3 as eluent, yielding compound 8 as a white solid (28%).
Analytical Data:
¹H-NMR (300 MHz, CDCl₃): δ 8.60 (d, J=5.8 Hz, 2H), 8.14 (s, 1H), 7.37 (d, J=8.8 Hz 2H), 7.29 (d, J=5.8 Hz, 2H), 7.11 (d, J=8.8, 2H), 5.33 (s, 2H).

Example 9

Synthesis of benzyl 1-(4-azidophenyl)-5-(trifluoromethyl)-1H-pyrazole-4-carboxylate The title compound was synthesized following the procedure described for Example 5. The crude product is subjected to chromatography column with petroleum ether/ethyl acetate 98:2 and petroleum ether/ethyl acetate 95:5 as eluent, yielding compound 9 as a white solid (60%).
Analytical Data:
¹H-NMR (300 MHz, CDCl₃ δ 8.13 (s, 1H), 7.60-7.23 (m, 7H), 7.13 (d, J=8.5 Hz, 2H), 5.36 (s, 2H).

Example 10

Synthesis of 2-morpholinoethyl 1-(4-azidophenyl)-5-(trifluoromethyl)-1H-pyrazole-4-carboxylate The title compound was synthesized following the procedure described for Example 5. The crude product is subjected to chromatography column with petroleum ether/ethyl acetate 8:2 and petroleum ether/ethyl acetate 7:3 as eluent, yielding compound 10 as a yellow oil (22%).
Analytical Data:
¹H-NMR (300 MHz, CDCl₃): δ 8.09 (s, 1H), 7.40 (d, J=8.5 Hz, 2H), 7.13 (d, J=8.5 Hz, 2H), 4.43 (t, J=5.8 Hz, 2H), 3.90-3.70 (t, J=4.11 Hz, 4H), 2.73 (t, J=5.8 Hz, 2H), 2.55 (t, J=4.11 Hz, 4H)

Example 11

Synthesis of 1-(4-nitrophenyl)-3,5-bis(trifluoromethyl)-4,5-dihydro-1H-pyrazol-5-ol (Intermediate 5)

1,1,1,5,5,5-Hexafluoropentane-2,4-dione (3.4 mL, 24.28 mmol), DMF (43.8 mL) and (4-nitrophenyl)hydrazine hydrochloride (4.38 g, 23.17 mmol) are added in order. The resulting mixture is stirred at reflux for 2 hours. The reaction is worked up by diluition with diethyl ether and washing with water (×3). The organic layer is dried over sodium sulfate and evaporated to give compound 11 as a yellow powder (7.55 g, 22.01 mmol, 95%).
Analytical Data:
¹H-NMR (300 MHz, CDCl₃): δ 8.12 (d, J 8.7 Hz, 2H), 7.58 (d, J 8.7 Hz, 2H), 3.76 (d, J 19.5 Hz, 1H), 3.42 (d, J 19.5 Hz, 1H). MS: M+1 344

Example 12

Synthesis of 1-(4-nitrophenyl)-3,5-bis(trifluoromethyl)-1H-pyrazole (Intermediate 6)

To a solution of 1-(4-nitrophenyl)-3,5-bis(trifluoromethyl)-4,5-dihydro-1H-pyrazol-5-ol (2 g, 5.83 mmol) in EtOH (100 mL) HCl 37% (10.6 mL) is added. The reaction is stirred at reflux for three days. After completion of the reaction, EtOH is removed under vacuo. Then, CH₂Cl₂ is added and the organic layer is washed with saturated aqueous NaHCO₃ solution (×2), dried over sodium sulfate and evaporated yielding compound 12 as a brown oil (1.65 g, 5.07 mmol, 87%).
Analytical Data:
¹H-NMR (300 MHz, CDCl₃): δ 8.40 (d, J 8.8 Hz, 2H), 7.75 (d, J 8.8 Hz, 2H), 7.15 (s, 1H). MS: M+1 326

Example 13

Synthesis of 4-(3,5-bis(trifluoromethyl)-1H-pyrazol-1-yl)aniline (Intermediate 7)

EtOAc (44 mL), Pd/C (1.3 g) and 1-(4-nitrophenyl)-3,5-bis(trifluoromethyl)-1H-pyrazole (4.4 g, 13.5 mmol) are added under hydrogen atmosphere. After stirring at room temperature for 2 hours the resulting mixture is filtered under vacuo over a pad of celite, rinsed with EtOAc and evaporated to give compound 13 as a pale yellow solid (3.75 g, 12.7 mmol, 94%).
Analytical Data:
¹H-NMR (300 MHz; CDCl₃): δ 7.22 (d, J 8.5 Hz, 2H), 7.00 (s, 1H), 6.72 (d, J 8.5 Hz, 2H). MS: M+1 296

Example 14

Synthesis of 1-(4-azidophenyl)-3,5-bis(trifluoromethyl)-1H-pyrazole (Intermediate 8)

To a solution of 4-(3,5-bis(trifluoromethyl)-1H-pyrazol-1-yl)aniline (4.16 g, 14.10 mmol) in water (62.7 mL) HCl 37% (5 mL) is added and the resulting mixture is cooled down at 0° C. Then, a solution of NaNO₂ (0.97 g, 14.10 mmol) in water (6 mL) is added and after 10 minutes a solution of NaN₃ (1.09 g, 16.9 mmol) in water (6 mL) is slowly added. The reaction is stirred at room temperature for additional 1 hour, diluted with EtOAc and washed with water (×2). The organic layer is dried over sodium sulfate and the volatile is removed under vacuum. The crude material is purified by column chromatography using petroleum ether/ethyl acetate 95:5 as eluent, yielding compound 14 as a pale red oil (3.84 g, 11.96 mmol, 85%).

Analytical Data:
$^1$H-NMR (300 MHz, CDCl$_3$): δ 7.47 (d, J 8.5 Hz, 2H), 7.14 (d, J 8.5 Hz, 2H), 7.0 (s, 1H). MS: M+1 322

Example 15

Synthesis of ethyl 1-(4-bromophenyl)-5-(trifluoromethyl)-1H-pyrazole-4-carboxylate (Intermediate 9)

(4-Bromophenyl)hydrazine hydrochloride (2 g, 8.97 mmol) DMF (20 mL) and (E)-ethyl 2-(ethoxymethylene)-4,4,4-trifluoro-3-oxobutanoate (1.83 mL, 9.42 mmol) are added. The reaction is stirred at reflux for 2 hours. Then, the mixture is diluted with diethyl ether and washed with water (×3). The organic layer is dried over sodium sulfate and evaporated to give compound 15 as yellow solid (2.83 g, 7.80 mmol, 87%).

Analytical Data:
$^1$H-NMR (300 MHz, CDCl$_3$): δ 8.11 (s, 1H), 7.64 (d, J 8.6 Hz, 2H), 7.30 (d, J 8.6 Hz, 2H), 4.37 (q, J 7.1, 2H), 1.38 (t, J 7.1 Hz, 3H). MS: M+1 364

Example 16

Synthesis of ethyl 5-(trifluoromethyl)-1-(4-((trimethylsilyl)ethynyl)phenyl)-1H-pyrazole-4-carboxylate (Intermediate 10)

To a solution of ethyl 1-(4-bromophenyl)-5-(trifluoromethyl)-1H-pyrazole-4-carboxylate (1.9 g, 5.23 mmol) in toluene (30 mL) DIPEA (3.6 mL, 20.9 mmol), CuI (0.18 g, 0.95 mmol), PdCl$_2$(PPh$_3$)$_2$ (0.23 g, 0.31 mmol) and ethynyltrimethylsilane (3 mL, 20.9 mmol) are added in a Schlenk apparatus. The reaction is stirred at reflux for 2 hours under nitrogen atmosphere. Ethyl acetate is added and the organic phase is washed with water (×1), dried over sodium sulfate and evaporated. The crude product is purified by column chromatography using as eluent petroleum ether/ethyl acetate 95:5 to give compound 16 as a brown solid (1.57 g, 4.13 mmol, 79%).

Analytical Data:
$^1$H-NMR (300 MHz, CDCl$_3$): δ 8.10 (s, 1H), 7.57 (d, J 8.2 Hz, 2H), 7.36 (d, J 8.2 Hz, 2H), 4.36 (q, J 7.1 Hz, 2H), 1.37 (t, J 7.1 Hz, 3H), 0.26 (s, 9H). MS: M+1 430

Example 17

Synthesis of ethyl 1-(4-ethynylphenyl)-5-(trifluoromethyl)-1H-pyrazole-4-carboxylate (Intermediate 11)

Ethyl 5-(trifluoromethyl)-1-(4-((trimethylsilyl)ethynyl)phenyl)-1H-pyrazole-4-carboxylate (1.3 g, 3.42 mmol) is dissolved in THF (13 mL). The mixture is cooled down at 0° C. and a solution of TBAF in THF 1M (4.1 mL) is added. The reaction is stirred for additional 30 minutes. The volatile is removed under vacuo, ethyl acetate is added and the organic layer is washed with water (×1). After drying over sodium sulfate and evaporation of the solvent, the crude product is purified by column chromatography using as eluent petroleum ether/ethyl acetate 95:5 to give compound 17 as a yellow solid (79%).

Analytical Data:
$^1$H-NMR (300 MHz, CDCl$_3$): δ 8.11 (s, 1H), 7.60 (d, J 8.2 Hz, 2H), 7.38 (d, J 8.2 Hz, 2H), 4.36 (q, J 7.1 Hz, 2H), 3.19 (s, 1H), 1.37 (t, J 7.1 Hz, 3H). MS: M+1 309

Example 18

Synthesis of 1-(4-bromophenyl)-3,5-bis(trifluoromethyl)-1H-pyrazole (Intermediate 12)

To a solution of (4-bromophenyl)hydrazine hydrochloride (1.29 g, 5.76 mmol) in EtOH (50 mL) 1,1,1,5,5,5-hexafluoropentane-2,4-dione (673 µL, 4.81 mmol) and concentrated H$_2$SO$_4$ (141 µL) are added and the resulting mixture is stirred at reflux for two days. The volatile is removed under vacuo. Then, CH$_2$Cl$_2$ is added and the organic phase is washed with aqueous saturated NaHCO$_3$ solution (×1), dried over sodium sulfate and evaporated, yielding a pale brown oil (1.87 g, 5.21 mmol, 90%).

Analytical Data:
$^1$H-NMR (300 MHz, CDCl$_3$): δ 7.66 (d, J 7.4 Hz, 2H), 7.38 (d, J 7.4 Hz, 2H), 7.07 (s, 1H). MS: M+1 360

Example 19

Synthesis of 3,5-bis(trifluoromethyl)-1-(4-((trimethylsilyl)ethynyl)phenyl)-1H-pyrazole (Intermediate 13)

To a solution of 1-(4-bromophenyl)-3,5-bis(trifluoromethyl)-1H-pyrazole (1.7 g, 4.73 mmol) in toluene (26.8 mL) DIPEA (3.3 mL, 18.9 mmol), CuI (0.16 g, 0.851 mmol), PdCl$_2$(PPh$_3$)$_2$ (0.21 g, 0.28 mmol) and ethynyltrimethylsilane (2.7 mL, 18.9 mmol) are added in a Schlenk apparatus. The reaction is stirred at reflux for 2 hours under nitrogen atmosphere. Ethyl acetate is added and the organic phase is washed with water (×1), dried over sodium sulfate and evaporated. The crude material is subjected to chromatography column with petroleum ether and petroleum ether/ethyl acetate 95:5 yielding compound 19 as a yellow oil (98%).

Analytical Data:
$^1$H-NMR (300 MHz, CDCl$_3$): δ 7.65 (d, J 8.3 Hz, 2H), 7.38 (d, J 8.3 Hz, 2H), 7.06 (s, 1H), 0.27 (s, 9H). MS: M+1 377

Example 20

Synthesis of 1-(4-ethynylphenyl)-3,5-bis(trifluoromethyl)-1H-pyrazole (Intermediate 14)

3,5-Bis(trifluoromethyl)-1-(4-((trimethylsilyl)ethynyl) phenyl)-1H-pyrazole (4.45 mg, 11.84 mmol) is dissolved in THF (44.5 mL). Then, the mixture is cooled at 0° C. and a solution of TBAF in THF 1 M (14.2 mL) is added. The reaction is stirred for additional 30 minutes. The volatile is removed under vacuo, ethyl acetate is added and the organic layer is washed with water (×1). After drying over sodium sulfate and evaporation of the solvent, the crude product is purified by column chromatography using as eluent petroleum ether and petroleum ether/ethyl acetate 95:5 to give compound 20 as a yellow solid (56%).

Analytical Data:
$^1$H-NMR (300 MHz, CDCl$_3$): δ 7.56 (d, J 6.9 Hz, 2H), 7.44 (d, J 6.9 Hz, 2H), 7.08 (s, 1H), 3.17 (s, 1H), 3.17 (s, 1H). MS: M+1 305

Example 21

Synthesis of ethyl 1-(4-(4-(3-aminophenyl)-1H-1,2,3-triazol-1-yl)phenyl)-5-(trifluoromethyl)-1H-pyrazole-4-carboxylate To a suspension of ethyl 1-(4-azidophenyl)-5-(trifluoromethyl)-1H-pyrazole-4-carboxylate (Intermediate 3 in Scheme b) (0.1 g, 0.31 mmol) in water (570 μL) and t-BuOH (570 μl) the alkyne (35 μL) is added. Then, 29 μL of an aqueous solution of sodium ascorbate 1M and copper sulfate pentahydrate (0.72 mg, 0.29 mmol) are added under vigorous stirring. The mixture is stirred overnight. After, 33% of an aqueous ammonia solution (1 mL) and ice are added and the precipitate is filtered under vacuo and rinsed with water and heptane. The crude product is subjected to chromatography column using petroleum ether/ethyl acetate 6:4 and then petroleum ether/ethyl acetate 4:6 as eluent, yielding compound 21 as pale green solid (83%).

Analytical Data:
$^1$H-NMR (300 MHz, DMSO-$d_6$): δ 9.27 (s, 1H), 8.36 (s, 1H), 8.18 (d, J 8.1 Hz, 2H), 7.84 (d, J 8.1 Hz, 2H), 7.22 (s, 1H), 7.13 (t, J 7.8 Hz, 1H), 7.05 (d, J 7.8 Hz, 1H), 6.60 (d, J 7.8 Hz, 1H), 5.25 (br s, 2H), 4.35 (q, J 6.9 Hz, 2H), 1.32 (t, J 7.1 Hz, 3H). MS: M+1 443

Example 22

Synthesis of ethyl 1-(4-(4-phenyl-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 8:2 and then ethyl acetate as eluent, yielding compound 22 as yellow solid (96%).

Analytical Data:
$^1$H-NMR (300 MHz, CDCl$_3$): δ 8.26 (s, 1H), 8.16 (s, 1H), 8.09-7.87 (m, 5H), 7.64 (d, J 7.4 Hz, 2H), 7.47 (d, J 7.4 Hz, 2H), 4.39 (q, J 6.6 Hz, 2H), 1.40 (t, J 6.6 Hz, 3H). MS: M+1 428

Example 23

Synthesis of ethyl 1-(4-(4-(4-methoxyphenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 8:2 as eluent to give compound 23 as yellow powder (82%).

Analytical Data:
$^1$H-NMR (300 MHz, DMSO-$d_6$): δ 9.32 (s, 1H), 8.36 (s, 1H), 8.17 (d, J 8.2 Hz, 2H), 7.97-7.80 (m, 4H), 7.09 (d, J 8.2 Hz, 2H), 4.34 (q, J 6.9 Hz, 2H), 3.82 (s, 3H), 1.32 (t, J 6.3 Hz, 3H). MS: M+1 458

Example 24

Synthesis of ethyl 1-(4-(4-(4-aminophenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 8:2 as eluent to give compound 24 as an amorphous white solid (43%).

Analytical Data:
$^1$H-NMR (300 MHz, DMSO-$d_6$): δ 9.12 (s, 1H), 8.36 (s, 1H), 8.15 (d, J 8.4 Hz, 2H), 7.83 (d, J 8.4 Hz, 2H), 7.61 (d, J 7.7 Hz, 2H), 6.67 (d, J 7.7 Hz, 2H) 5.35 (br s, 2H), 4.34 (q, J 7.4 Hz, 2H), 1.32 (t, J 6.8 Hz, 3H). MS: M+1 443

Example 25

Synthesis of ethyl 1-(4-(4-(3-hydroxyphenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 9:1 and then petroleum ether/ethyl acetate 6:4 as eluent to give compound 25 as yellow powder (95%).

Analytical Data:
$^1$H-NMR (300 MHz, DMSO-$d_6$): δ 9.65 (s, 1H), 9.36 (s, 1H), 8.37 (s, 1H), 8.19 (d, J 7.8 Hz, 2H), 7.86 (d, J 7.8 Hz, 2H), 7.38 (d, J 7.7 Hz, 1H), 7.30 (t, J 7.7 Hz, 1H), 6.80 (d, J 7.7 Hz, 1H), 4.34 (q, J 6.9 Hz, 2H), 1.32 (t, J 7.1 Hz, 3H). MS: M+1 444

Example 26

Synthesis of ethyl 1-(4-(4-(4-hydroxy-3-methoxyphenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 8:2 and petroleum ether/ethyl acetate 5:5 as eluent, yielding compound 26 as a brown solid (20%).

Analytical Data:
$^1$H-NMR (300 MHz, DMSO-$d_6$): δ 9.28 (s, 1H), 8.35 (s, 1H), 8.17 (d, J 8.1 Hz, 2H), 7.82 (d, J 8.1 Hz, 2H), 7.50 (s, 1H), 7.38 (d, J 8.0 Hz, 1H), 6.90 (d, J 8.0 Hz, 1H), 4.32 (q, J 7.1 Hz, 2H), 3.87 (s, 3H), 1.30 (t, J 7.1 Hz, 3H). MS: M+1 474

Example 27

Synthesis of ethyl 1-(4-(4-(3-methoxyphenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 8:2 as eluent to give compound 27 as a yellow solid (97%).

Analytical Data:
$^1$H-NMR (300 MHz, DMSO-$d_6$): δ 9.38 (s, 1H), 8.33 (s, 1H), 8.18 (d, J 8.0 Hz, 2H), 7.84 (d, J 8.0 Hz, 2H), 7.55 (m, 2H), 7.43 (t, J 7.8 Hz, 1H), 6.98 (d, J 7.8 Hz, 1H), 4.35 (q, J 6.8 Hz, 2H), 3.86 (s, 3H), 1.33 (t, J 6.9 Hz, 3H). MS: M+1 458

Example 28

Synthesis of 3-(1-(4-(4-(ethoxycarbonyl)-5-(trifluoromethyl)-1H-pyrazol-1-yl)phenyl)-1H-1,2,3-triazol-4-yl)benzoic acid The title compound was synthesized following the procedure described for Example 21. The crude product is subjected to chromatography column using petroleum ether/ethyl acetate 8:2 and then petroleum ether/ethyl acetate 2:8 (+HCOOH 0.1%) as eluent, yielding compound 28 as a yellowish powder (45%).
Analytical Data:
$^1$H-NMR (300 MHz, DMSO-$d_6$): δ 9.59 (s, 1H), 8.55 (s, 1H), 8.37 (s, 1H), 8.04-7.81 (m, 3H), 7.97 (d, J 6.5 Hz, 1H), 7.87 (d, J 8.3 Hz, 2H), 7.67 (t, J 6.5 Hz, 1H), 4.34 (q, J 7.2 Hz, 2H), 1.32 (t, J 7.1 Hz, 3H). MS: M+1 472

Example 29

Synthesis of 4-(1-(4-(4-(ethoxycarbonyl)-5-(trifluoromethyl)-1H-pyrazol-1-yl)phenyl)-1H-1,2,3-triazol-4-yl)benzoic acid The title compound was synthesized following the procedure described for Example 21 (91%). The crude product is subjected to chromatography column using petroleum ether/ethyl acetate 8:2 and then ethyl acetate (+HCOOH 0.1%) as eluent, yielding compound 29 as yellowish powder (72%).
Analytical Data:
$^1$H-NMR (300 MHz, DMSO-$d_6$): δ 9.56 (s, 1H), 8.36 (s, 1H), 8.19 (d, J 7.4 Hz, 2H), 8.14-8.03 (m, 4H), 7.87 (d, J 7.4 Hz, 2H), 4.34 (q, J 6.6 Hz, 2H), 1.32 (t, J 6.3 Hz, 3H) MS: M+1 472

Example 30

Synthesis of ethyl 1-(4-(4-(3,5-dimethoxyphenyl)-H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 8:2 and then petroleum ether/ethyl acetate 6:4 as eluent to give compound 30 as yellow powder (85%).
Analytical Data:
$^1$H-NMR (300 MHz, CDCl$_3$): δ 8.24 (s, 1H), 8.16 (s, 1H), 7.97 (d, J 8.6 Hz, 2H), 7.64 (d, J 8.6 Hz, 2H), 7.09 (s, 2H), 6.51 (s, 1H), 4.39 (q, J 7.2 HZ, 2H), 3.88 (s, 6H), 1.40 (t, J 7.1 Hz, 3H). MS: M+1 488

Example 31

Synthesis of ethyl 1-(4-(4-(3,4-dimethoxyphenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 8:2 and then petroleum ether/ethyl acetate 6:4 as eluent, yielding compound 31 as a yellow solid (64%).
Analytical Data:
$^1$H-NMR (300 MHz, DMSO-$d_6$): δ 9.35 (s, 1H), 8.36 (s, 1H), 8.17 (d, J 8.6 Hz, 2H), 7.86 (d, J 8.6 Hz, 2H), 7.60-7.45 (m, 2H), 7.10 (d, J 8.0 Hz, 1H), 4.34 (q, J 7.0 Hz, 2H), 3.87 (s, 3H), 3.82 (s, 3H), 1.32 (t, J 7.0 Hz, 3H). MS: M+1 488

Example 31

Synthesis of ethyl 1-(4-(4-(2-acetamidophenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 8:2 and then petroleum ether/ethyl acetate 6:4 as eluent, yielding compound 32 as a yellow solid (86%).
Analytical Data:
$^1$H-NMR (300 MHz, DMSO-$d_6$): δ 8.62 (d, J 7.4 Hz, 1H), 8.34 (s, 1H), 8.17 (s, 1H), 7.99 (d, J 7.3 Hz, 2H), 7.68 (d, J 7.3 Hz, 2H), 7.56 (d, J 7.4 Hz, 1H), 7.40 (t, J 7.4 Hz, 1H), 7.15 (t, J 7.4 Hz, 1H), 4.38 (q, J 6.9 Hz, 2H), 2.30 (s, 3H), 1.40 (t, J 6.6 Hz, 3H). MS: M+1 485

Example 33

Synthesis of ethyl 1-(4-(4-(3-carbamoylphenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 5:5 and then petroleum ether/ethyl acetate 2:8 as eluent, yielding compound 33 as a yellow powder (65%).
Analytical Data:
$^1$H-NMR (300 MHz, DMSO-$d_6$): δ 9.51 (s, 1H), 8.49 (s, 1H), 8.35 (s, 1H), 8.20 (d, J 8.8 Hz, 2H), 8.10 (d, J 7.5 Hz, 1H), 7.98-7.80 (m, 3H), 7.59 (t, J 7.5 Hz, 1H), 7.51 (br s, 1H), 4.32 (d, J 6.7 Hz, 2H), 1.30 (t, J 6.9 Hz, 3H). MS: M+1 471

Example 34

Synthesis of ethyl 1-(4-(4-(3-(methoxycarbonyl)phenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ethyl acetate 9:1 and then petroleum ether/ethyl acetate 5:5 as eluent, yielding compound 34 as a yellow powder (59%).
Analytical Data:
$^1$H-NMR (300 MHz, DMSO-$d_6$): δ 9.61 (s, 1H), 8.55 (s, 1H), 8.37 (s, 1H), 8.31-8.10 (m, 3H), 7.99 (d, J 7.7 Hz, 1H), 7.84 (d, J 6.1 Hz, 2H), 7.69 (t, J 7.7 Hz, 1H), 4.34 (q, J 7.1 Hz, 2H), 3.92 (s, 3H), 1.32 (t, J 7.0 Hz, 3H). MS: M+1 486

Example 35

Synthesis of ethyl 1-(4-(4-(3-sulfamoylphenyl)-1H-1,2,3-triazol-1-yl)phenyl)-5-(trifluoromethyl)-1H-pyrazole-4-carboxylate The title compound was synthesized following the procedure described for Example 21. The crude product is subjected to chromatography column using petroleum ether/ ethyl acetate 8:2 and then petroleum ether/ethyl acetate 5:5 (+HCOOH 0.1%) as eluent, yielding compound 35 as a yellow powder (42%).

Analytical Data:
$^1$H-NMR (300 MHz, DMSO-d$_6$): δ 9.61 (s, 1H), 8.46 (s, 1H), 8.38 (s, 1H), 8.22 (d, J 8.8 Hz, 2H), 8.15 (d, J 7.7 Hz, 2H), 7.89-7.81 (m, 3H), 7.74 (t, J 7.7 Hz, 1H), 7.51 (br s, 2H), 4.34 (q, J 6.9 Hz, 2H), 1.32 (t, J 7.1 Hz, 3H). MS: M+1 507

Example 36

Synthesis of 3-(1-(4-(3,5-bis(trifluoromethyl)-H-pyrazol-1-yl)phenyl)-1H-1,2,3-triazol-4-yl)benzoic acid To a suspension of 1-(4-azidophenyl)-3,5-bis(trifluoromethyl)-1H-pyrazole (Intermediate 7 in scheme c) (0.1 g, 0.31 mmol) in water (612 μL) and t-BuOH (612 μl) alkyne (35 μL) is added. Then, 31 μL of an aqueous solution of sodium ascorbate 1M and iron sulfate pentahydrate (0.77 mg, 0.0031 mmol) are added under vigorous stirring. The mixture is stirred overnight. After, 33% aqueous ammonia solution (1 mL) and ice are added and the precipitate is filtered under vacuo rinsed with water and heptane. The crude product is subjected to chromatography column using petroleum ether/ethyl acetate 8:2 and then petroleum ether/ethyl acetate 2:8 (+HCOOH 0.1%) as eluent to give a yellow powder (63%).

Analytical Data:
$^1$H-NMR (300 MHz, DMSO-d$_6$): δ 9.1 (s, 1H), 8.55 (s, 1H), 8.25 (d, J 8.8 Hz, 2H), 8.20 (s, 1H), 8.10-7.86 (m, 4H), 7.66 (t, J 7.7, 1H). MS: M+1 468

Example 37

Synthesis of 4-(1-(4-(3,5-bis(trifluoromethyl)-H-pyrazol-1-yl)phenyl)-1H-1,2,3-triazol-4-yl)benzoic acid The title compound was synthesized following the procedure described for Example 36. The crude product is subjected to chromatography column using petroleum ether/ethyl acetate 3:7 and then ethyl acetate as eluent, yielding compound 37 as a yellow powder (44%).

Analytical Data:
$^1$H-NMR (300 MHz, (CH$_3$)$_2$CO): δ 9.31 (s, 1H), 8.29 (d, J 8.1 Hz, 2H), 8.21-8.12 (m, 4H), 7.95 (d, J 8.1 Hz, 2H), 7.58 (s, 1H). MS: M+1 468

Example 38

Synthesis of 1-(4-(3,5-bis(trifluoromethyl)-1H-pyrazol-1-yl)phenyl)-4-phenyl-1H-1,2,3-triazole The title compound was synthesized following the procedure described for Example 36. The crude product is subjected to chromatography column using petroleum ether/ethyl acetate 8:2 and then ethyl acetate as eluent, yielding compound 38 as a yellow solid (92%).

Analytical Data:
$^1$H-NMR (300 MHz, DMSO-d$_6$): δ 9.39 (s, 1H), 8.22 (d, J 8.0 Hz, 2H), 8.12-7.80 (m, 5H), 7.55 (s, 1H), 7.52 (d, J 8.0 Hz, 1H), 7.41 (t, J 7.4 Hz, 1H). MS: M+1 424

Example 39

Synthesis of 4-(1-(4-(3,5-bis(trifluoromethyl)-H-pyrazol-1-yl)phenyl)-1H-1,2,3-triazol-4-yl)butanoic acid The title compound was synthesized following the procedure described for Example 36. The crude product is subjected to chromatography column using petroleum ether/ethyl acetate 7:3, ethyl acetate/methanol 9:1 and ethyl acetate/methanol 8:2 as eluent, yielding compound 39 as a white solid (65%).

Analytical Data:
$^1$H-NMR (300 MHz, DMSO-d$_6$): δ 8.76 (s, 1H), 8.15 (d, J 8.5 Hz, 2H), 7.95-7.81 (m, 3H), 2.76 (t, J 7.1 Hz, 2H), 2.36 (t, J 7.1 Hz, 2H), 1.92 (quint, J 7.1 Hz, 2H). MS: M+1 434

Example 40

Synthesis of 3-(1-(4-(3,5-bis(trifluoromethyl)-H-pyrazol-1-yl)phenyl)-1H-1,2,3-triazol-4-yl)phenol The title compound was synthesized following the procedure described for Example 36. The crude product is subjected to chromatography column using petroleum ether/ethyl acetate 9:1 and then petroleum ether/ethyl acetate 7:3 as eluent, yielding compound 40 as white powder (74%).

Analytical Data:
$^1$H-NMR (300 MHz, DMSO-d$_6$): 9.64 (s, 1H), 9.39 (s, 1H), 8.22 (d, J 8.8 Hz, 2H), 7.93 (d, J 8.8 Hz, 2H), 7.91 (s, 1H), 7.40 (br s, 1H), 7.37-7.26 (m, 2H), 6.80 (d, J 6.9 Hz, 1H). MS: M+1 441

Example 41

Synthesis of 4-(4-(4-(4-(ethoxycarbonyl)-5-(trifluoromethyl)-1H-pyrazol-1-yl)phenyl)-1H-1,2,3-triazol-1-yl)butanoic acid To a suspension of azide (37.4 mg, 0.29 mmol) in water (570 μL) and t-BuOH (570 μL) ethyl 1-(4-ethynylphenyl)-5-(trifluoromethyl)-1H-pyrazole-4-carboxylate (91 mg, 0.29 mmol) is added. Then, 30 μL of an aqueous solution of sodium ascorbate 1M and copper sulfate pentahydrate (0.72 mg, 0.0029 mmol) are added under vigorous stirring and the mixture is left to react overnight. Ice is added to precipitate out the product, which is filtered under vacuo rinsed with water and heptane. The crude product is subjected to chromatography column using petroleum ether/ethyl acetate 8:2, petroleum ether/ethyl acetate 2:8 (+HCOOH 0.1%) and ethyl acetate (+HCOOH 0.1%) as eluent, yielding compound 41 as an off-white powder (68%).

Analytical Data:
$^1$H-NMR (300 MHz, DMSO-d$_6$): δ 8.74 (s, 1H), 8.32 (s, 1H), 8.05 (d, J 8.3 Hz, 2H), 7.63 (d, J 8.3 Hz, 2H), 4.47 (t, J 6.9 Hz, 2H), 4.33 (q, J 6.9 Hz, 2H), 2.30 (t, J 6.9 Hz, 2H), 2.11 (quint, J 6.9 Hz, 2H), 1.31 (t, J 7.1 Hz, 3H). MS: M+1 438

Example 42

Synthesis of ethyl 1-(4-(1-(4-chlorophenyl)-1H-1,2,3-triazol-4-yl)phenyl)-5-(trifluoromethyl)-1H-pyrazole-4-carboxylate The title compound was synthesized following the procedure described for Example 41. The crude product is subjected to chromatography column using petroleum ether/ethyl acetate 9:1, petroleum ether/ethyl acetate 8:2 and petroleum ether/ethyl acetate 7:3 as eluent, yielding compound 42 as a yellow powder (58%).

Analytical Data:
$^1$H-NMR (300 MHz, CDCl$_3$): δ 8.25 (s, 1H), 8.14 (s, 1H), 8.04 (d, J 8.7 Hz, 2H), 7.76 (d, J 8.7 Hz, 2H), 7.60-7.48 (m, 4H), 4.38 (q, J 7.1 Hz, 2H), 1.39 (t, J 7.1 Hz, 3H). MS: M+1 462

Example 43

Synthesis of ethyl 1-(4-(1-(3-aminophenyl)-1H-1,2,3-triazol-4-yl)phenyl)-5-(trifluoromethyl)-1H-pyrazole-4-carboxylate The title compound was synthesized following the procedure described for Example 41. The crude product is subjected to chromatography column using petroleum ether/ethyl acetate 7:3 and then petroleum ether/ethyl acetate 5:5 as eluent, yielding compound 43 as a dark brown solid (69%).

Analytical Data:
$^1$H-NMR (300 MHz, DMSO-d$_6$): δ 9.30 (s, 1H), 8.33 (s, 1H), 8.14 (d, J 8.3 Hz, 2H), 7.68 (d, J 8.3 Hz, 2H), 7.27 (t, J 7.7 Hz, 1H), 7.16 (s, 1H), 6.99 (d, J 7.7 Hz, 1H), 6.69 (d, J 7.7 Hz, 1H), 5.59 (br s, 2H), 4.33 (q, J 7.0 Hz, 2H), 1.32 (t, J 7.1 Hz, 3H). MS: M+1 443

Example 44

Synthesis of ethyl 1-(4-(1-(3-fluoropyridin-4-yl)-1H-1,2,3-triazol-4-yl)phenyl)-5-(trifluoromethyl)-1H-pyrazole-4-carboxylate The title compound was synthesized following the procedure described for Example 41. The crude product is subjected to chromatography column with petroleum ether/ethyl acetate 95:5, petroleum ether/ethyl acetate 8:2 and then petroleum ether/ethyl acetate 5:5 as eluent, yielding compound 44 as a pale yellow solid (30%).

Analytical Data:
$^1$H-NMR (300 MHz, DMSO-d$_6$): δ 9.39 (s, 1H), 8.99 (d, J 5.8 Hz, 1H), 8.71 (d, J 5.8 Hz, 1H), 8.34 (s, 1H), 8.21 (d, J 8.3 Hz, 2H), 8.13 (t, J 5.8 Hz, 1H), 7.71 (d, J 8.3 Hz, 2H), 4.33 (q, J 7.0 Hz, 2H), 1.32 (t, J 7.0 Hz, 3H). MS: M+1 447

Example 45

Synthesis of 3-(4-(4-(4-(ethoxycarbonyl)-5-(trifluoromethyl)-1H-pyrazol-1-yl)phenyl)-1H-1,2,3-triazol-1-yl)benzoic acid The title compound was synthesized following the procedure described for Example 41. The crude product is subjected to chromatography column using petroleum ether/ethyl acetate 8:2, ethyl acetate and then ethyl acetate/methanol (+HCOOH 0.1%) as eluent, yielding compound 45 as a yellow solid (43%).

Analytical Data:
$^1$H-NMR (300 MHz, DMSO-d$_6$): δ 9.58 (s, 1H), 8.50 (s, 1H), 8.30 (s, 1H), 8.22 (d, J 7.4 Hz, 1H), 8.16 (d, J 8.0 Hz, 2H), 8.07 (d, J 7.4 Hz, 1H), 7.80 (t, J 7.4 Hz, 1H), 7.68 (d, J 8.0 Hz, 2H), 4.31 (q, J 7.1 Hz, 2H), 1.30 (t, J 7.1 Hz, 3H). MS: M+1 472

Example 46

Synthesis of 4-(4-(4-(4-(ethoxycarbonyl)-5-(trifluoromethyl)-1H-pyrazol-1-yl)phenyl)-1H-1,2,3-triazol-1-yl)benzoic acid The title compound was synthesized following the procedure described for Example 41. The crude product is subjected to chromatography column using petroleum ether/ethyl acetate 8:2, petroleum ether/ethyl acetate 2:8 (+HCOOH 0.1%) and ethyl acetate/methanol 9:1 (+HCOOH 0.1%) as eluent, yielding compound 46 as a white powder (83%).

Analytical Data:
$^1$H-NMR (300 MHz, DMSO-d$_6$): δ 9.57 (s, 1H), 8.34 (s, 1H), 8.25-8.04 (m, 6H), 7.71 (d, J 8.3 Hz, 2H), 4.33 (q, J 7.1 Hz, 2H), 1.32 (t, J 6.9 Hz, 3H). MS: M+1 472

Example 47

Synthesis of ethyl 1-(4-(1-(3,5-dimethoxyphenyl)-1H-1,2,3-triazol-4-yl)phenyl)-5-(trifluoromethyl)-1H-pyrazole-4-carboxylate The title compound was synthesized following the procedure described for Example 41. The crude product is subjected to chromatography column with petroleum ether/ethyl acetate 8:2 and then petroleum ether/ethyl acetate 6:4 as eluent, yielding compound 47 as a yellow powder (71%).

Analytical Data:
$^1$H-NMR (300 MHz, DMSO-d$_6$): δ 9.44 (s, 1H), 8.32 (s, 1H), 8.12 (d, J 8.4 Hz, 2H), 7.69 (d, J 8.4 Hz, 2H), 7.15 (s, 2H), 6.64 (s, 1H), 4.32 (q, J 6.8 Hz, 2H), 3.86 (s, 6H), 1.31 (t, J 7.1 Hz, 3H). MS: M+1 488

Example 48

Synthesis of ethyl 1-(4-(1-(4-methoxyphenyl)-1H-1,2,3-triazol-4-yl)phenyl)-5-(trifluoromethyl)-1H-pyrazole-4-carboxylate The title compound was synthesized following the procedure described for Example 41. The crude product is subjected to chromatography column using petroleum ether/ethyl acetate 8:2 as eluent to give compound 48 as yellow powder (68%).

Analytical Data:
$^1$H-NMR (300 MHz, CDCl$_3$): δ 8.19 (s, 1H), 8.13 (s, 1H), 8.04 (d, J 7.8 Hz, 2H) 7.69 (d, J 7.7 Hz, 2H), 7.52 (d, J 7.7 Hz, 2H), 7.05 (d, J 7.8 Hz, 2H), 4.38 (q, J 6.9 Hz, 2H), 3.88 (s, 3H), 1.39 (t, J 6.6 Hz, 3H). MS: M+1 458

Example 49

Synthesis of ethyl 1-(4-(1-(pyridin-3-yl)-1H-1,2,3-triazol-4-yl)phenyl)-5-(trifluoromethyl)-1H-pyrazole-4-carboxylate The title compound was synthesized following the procedure described for Example 41. The crude product is subjected to chromatography column with petroleum ether/ ethyl acetate 5:5 and then petroleum ether/ethyl acetate 4:6 as eluent, yielding compound 49 as a white solid (72%).

Analytical Data:
$^1$H-NMR (300 MHz, DMSO-d$_6$): δ 9.53 (s, 1H), 9.21 (s, 1H), 8.75 (d, J 5.0 Hz, 1H), 8.40 (d, J 7.1 Hz, 1H), 8.34 (s, 1H), 8.14 (d, J 8.2 Hz, 2H), 7.75-7.66 (m, 3H), 4.33 (q, J 6.9 Hz, 2H), 1.29 (t, J 7.1 Hz, 3H). MS: M+1 429

Example 50

Synthesis of ethyl 1-(4-(1-(pyridin-4-yl)-1H-1,2,3-triazol-4-yl)phenyl)-5-(trifluoromethyl)-1H-pyrazole-4-carboxylate The title compound was synthesized following the procedure described for Example 41. The crude product is subjected to chromatography column with petroleum ether/ ethyl acetate 2:8 and then petroleum ether/ethyl acetate 1:9 as eluent, yielding compound 50 as a white solid (67%).

Analytical Data:
$^1$H-NMR (300 MHz, DMSO-d$_6$): δ 9.66 (s, 1H), 8.86 (br s, 2H), 8.35 (s, 1H), 8.15 (d, J 8.3 Hz, 2H), 8.04 (d, J 5.2 Hz, 2H), 7.73 (d, J 8.3 Hz, 2H), 4.33 (q, J 6.9 Hz, 2H), 1.32 (t, J 7.1 Hz, 3H). MS: M+1 429

Example 51

Synthesis of ethyl 1-(4-(1-(3,4-dimethoxyphenyl)-1H-1,2,3-triazol-4-yl)phenyl)-5-(trifluoromethyl)-1H-pyrazole-4-carboxylate The title compound was synthesized following the procedure described for Example 41. The crude product is subjected to chromatography column with petroleum ether/ ethyl acetate 7:3 and then petroleum ether/ethyl acetate 6:4 as eluent, yielding compound 51 as a white powder (72%).

Analytical Data:
$^1$H-NMR (300 MHz, DMSO-d$_6$): δ 9.37 (s, 1H), 8.34 (s, 1H), 8.13 (d, J 8.3 Hz, 2H), 7.76 (d, J 8.3 Hz, 2H), 7.53 (s, 1H), 7.48 (d, J 8.5 Hz, 1H), 7.19 (d, J 8.5 Hz, 1H), 4.33 (q, J 6.9 Hz, 2H), 3.89 (s, 3H), 3.78 (s, 3H), 1.31 (t, J 6.9 Hz, 3H). MS: M+1 488

Example 52

Synthesis of 4-(4-(3,5-bis(trifluoromethyl)-1H-pyrazol-1-yl)phenyl)-1-(4-methoxyphenyl)-1H-1,2,3-triazole To a suspension of azide (43 mg, 0.29 mmol) in water (570 µL) and t-BuOH (570 µL) 1-(4-ethynylphenyl)-3,5-bis(trifluoromethyl)-1H-pyrazole (Intermediate 13 in scheme f) (88 mg, 0.29 mmol) is added. Then, 30 µL of an aqueous solution of sodium ascorbate 1M and iron sulfate pentahydrate (0.72 mg, 0.0029 mmol) are added under vigorous stirring and the mixture is left to react overnight. Ice is added to precipitate out the product, which is filtered under vacuo rinsed with water and heptane. The crude product is subjected to chromatography column using petroleum ether/ ethyl acetate 8:2, petroleum ether/ethyl acetate 6:4 and petroleum ether/ethyl acetate 2:8 as eluent, yielding compound 52 as yellow powder (66%).

Analytical Data:
$^1$H-NMR (300 MHz, DMSO-d$_6$): δ 9.30 (s, 1H), 8.16 (d, J 8.2 Hz, 2H), 7.87 (d, J 8.9 Hz, 2H), 7.81 (s, 1H), 7.79 (d, J 8.9 Hz, 2H), 7.20 (d, J 8.2 Hz, 2H), 3.87 (s, 3H). MS: M+1 454

Example 53

Synthesis of 4-(4-(4-(3,5-bis(trifluoromethyl)-1H-pyrazol-1-yl)phenyl)-1H-1,2,3-triazol-1-yl)butanoic acid The title compound was synthesized following the procedure described for Example 52. The crude product is subjected to chromatography column with ethyl acetate and then ethyl acetate/methanol 9:1 as eluent, yielding compound 53 as a pale yellow powder (71%).

Analytical Data:
$^1$H-NMR (300 MHz, DMSO-d$_6$): δ 8.75 (s, 1H), 8.07 (d, J 7.4 Hz, 2H), 7.85 (s, 1H), 7.70 (d, J 7.4 Hz, 2H), 4.47 (t, J 7.1 Hz, 2H), 3.33 (t, J 7.1 Hz, 2H), 2.14 (quint, J 7.1 Hz, 2H). MS: M+1 434

Example 54

Synthesis of 4-(4-(3,5-bis(trifluoromethyl)-1H-pyrazol-1-yl)phenyl)-1-(3,4-dimethoxyphenyl)-1H-1,2,3-triazole The title compound was synthesized following the procedure described for Example 52. The crude product is subjected to chromatography column with petroleum ether/ ethyl acetate 6:4 as eluent, yielding compound 54 as a pale orange powder (87%).

Analytical Data:
$^1$H-NMR (300 MHz, DMSO-d$_6$): δ 9.38 (s, 1H), 8.16 (d, J 8.3 Hz, 2H), 7.87 (s, 1H), 7.77 (d, J 8.3 Hz, 2H), 7.54 (s, 1H), 7.48 (d, J 8.6 Hz, 1H), 7.19 (d, J 8.6 Hz, 1H), 3.90 (s, 3H), 3.79 (s, 3H). MS: M+1 484

Example 55

Synthesis of 3-(4-(4-(3,5-bis(trifluoromethyl)-1H-pyrazol-1-yl)phenyl)-1H-1,2,3-triazol-1-yl)benzoic acid The title compound was synthesized following the procedure described for Example 52. The crude product is subjected to chromatography column with petroleum ether/ ethyl acetate 2:8 and then ethyl acetate (+HCOOH 0.1%) as eluent, yielding compound 55 as a white powder (59%).

Analytical Data:
$^1$H-NMR (300 MHz, DMSO-d$_6$): δ 9.62 (s, 1H), 8.50 (s, 1H), 8.28-8.15 (m, 3H), 8.08 (d, J 7.1 Hz, 1H), 7.87 (s, 1H), 7.88-7.71 (m, 3H). MS: M+1 468

Example 56

Synthesis of methyl 1-(4-(1-(4-chlorophenyl)-1H-1,2,3-triazol-4-yl)phenyl)-5-(trifluoromethyl)-1H-pyrazole-4-carboxylate The title compound was synthesized following the procedure described for Example 52. The crude product is subjected to chromatography column with petroleum ether/ ethyl acetate 2:8 as eluent, yielding compound 56 as a pale brown powder (42%).

Analytical Data:
$^1$H-NMR (300 MHz, CDCl$_3$): δ 8.26 (s, 1H), 8.13 (s, 1H), 8.04 (d, J 8.6 Hz, 2H), 7.76 (d, J 8.6 Hz, 2H), 7.57-7.49 (m, 4H), 3.92 (s, 3H). MS: M+1 448

Example 57

Synthesis of isopropyl 1-(4-(1-(4-chlorophenyl)-H-1,2,3-triazol-4-yl)phenyl)-5-(trifluoromethyl)-1H-pyrazole-4-carboxylate The title compound was synthesized following the procedure described for Example 52. The crude product is subjected to chromatography column with ethyl acetate as eluent, yielding compound 57 as a white powder (59%).
Analytical Data:
$^1$H-NMR (300 MHz, CDCl$_3$): δ 8.26 (s, 1H), 8.12 (s, 1H), 8.03 (d, J 8.4 Hz, 2H), 7.75 (d, J 8.4 Hz, 2H), 7-61-7.42 (m, 4H), 5.24 (ept, J 6.3 Hz, 1H), 1.36 (d, J 6.0 Hz, 6H). MS: M+1 476

Example 58

Synthesis of 3-(1-(4-(4-(methoxycarbonyl)-5-(trifluoromethyl)-1H-pyrazol-1-yl)phenyl)-1H-1,2,3-triazol-4-yl)benzoic acid To a suspension of azide (0.1 g, 0.31 mmol) in water (570 μL) and t-BuOH (570 μl) the alkyne (35 μL) is added. Then, 29 μL of an aqueous solution of sodium ascorbate 1M and copper sulfate pentahydrate (0.72 mg, 0.29 mmol) are added under vigorous stirring. The mixture is stirred overnight. Then, the volatile is removed under reduced pressure and the crude product is subjected to chromatography column using petroleum ether/ethyl acetate 3:7, petroleum ether/ethyl acetate 1:9, ethyl acetate and then ethyl acetate/methanol 9:1 (+HCOOH 1%) as eluent, yielding compound 58 as a yellowish powder (49%).
Analytical Data:
$^1$H-NMR (300 MHz, DMSO-d$_6$): δ (s, 1H), 8.56 (s, 1H), 8.33 (s, 1H), 8.26-8.19 (m, 3H), 7.97 (d, J 6.9 Hz, 1H), 7.84 (d, J 8.4 Hz, 2H), 7.62 (t, J 6.9 Hz, 1H), 3.86 (s, 3H). MS: M+1 458

Example 59

Synthesis of 3-(1-(4-(4-(isopropoxycarbonyl)-5-(trifluoromethyl)-1H-pyrazol-1-yl)phenyl)-1H-1,2,3-triazol-4-yl)benzoic acid The title compound was synthesized following the procedure described for Example 58. The crude product is subjected to chromatography column using petroleum ether/ethyl acetate 3:7, petroleum ether/ethyl acetate 1:9, ethyl acetate and then ethyl acetate/methanol 9:1 (+HCOOH 1%). as eluent, yielding compound 59 as white powder (51%).
Analytical Data:
$^1$H-NMR (300 MHz, DMSO-d$_6$): δ 9.58 (s, 1H), 8.55 (s, 1H), 8.23 (s, 1H), 8.27-8.05 (m, 3H), 7.97 (d, J 7.6 Hz, 1H), 7.86 (d, J 8.4 Hz, 2H), 7.64 (t, J 7.6 Hz, 1H), 5.15 (ept, J 6.3 Hz, 1H), 1.32 (t, J 6.0 Hz, 6H). MS: M+1 486

Example 60

Synthesis of 3-(1-(4-(4-((pentan-2-yloxy)carbonyl)-5-(trifluoromethyl)-1H-pyrazol-1-yl)phenyl)-1H-1,2,3-triazol-4-yl)benzoic acid The title compound was synthesized following the procedure described for Example 58. The crude product is subjected to chromatography column using petroleum ether/ethyl acetate 8:2, petroleum ether/ethyl acetate 7:3, petroleum ether/ethyl acetate 5:5, petroleum ether/ethyl acetate 3:7 (+HCOOH 1%) as eluent, yielding compound 60 as white powder (59%).
Analytical Data:
$^1$H-NMR (300 MHz, CD$_3$Cl$_3$): δ 8.59 (s, 1H), 8.42 (s, 1H), 8.18-8.10 (m, 4H), 8.00 (d, J=8.5 Hz, 2H), 7.65 (d, J=8.5 Hz, 2H), 1.80-1.65 (m, 2H), 1.63-1.50 (m, 1H), 1.42-1.31 (m, 5H), 0.95 (t, J 7.4 Hz, 3H). MS: M+1 514

Example 61

Synthesis of 3-(1-(4-(4-((pyridin-4-ylmethoxy)carbonyl)-5-(trifluoromethyl)-1H-pyrazol-1-yl)phenyl)-1H-1,2,3-triazol-4-yl)benzoic acid The title compound was synthesized following the procedure described for Example 58. The crude product is subjected to chromatography column using petroleum ether/ethyl acetate 2:8 and ethyl acetate (+HCOOH 1%) as eluent, yielding compound 61 as white powder (56%).
Analytical Data:
$^1$H-NMR (300 MHz, CD$_3$OD): δ 9.60 (br s, 1H), 8.73-8.49 (m, 5H), 8.30-8.16 (m, 3H), 8.08-7.68 (m, 5H), 7.47 (s, 1H), 5.43 (s, 2H). MS: M+1 535

Example 62

3-(1-(4-(4-((2-morpholinoethoxy)carbonyl)-5-(trifluoromethyl)-1H-pyrazol-1-yl)phenyl)-1H-1,2,3-triazol-4-yl)benzoic Acid The title compound was synthesized following the procedure described for Example 58. The crude product is subjected to chromatography column using petroleum ether/ethyl acetate 2:8, ethyl acetate and ethyl acetate/methanol 9:1 (+HCOOH 1%). as eluent, yielding compound 62 as pale yellow powder (33%).
Analytical Data:
$^1$H-NMR (300 MHz, DMSO-D$_6$): δ 8.40 (d, J=7.6 Hz, 2H), 8.26 (s, 1H), 8.18 (s, 1H), 8.04 (s, 1H), 7.52 (t, J=7.6 Hz, 1H), 7.80 (d, J=8.3 Hz), 7.39 (d, J=8.3 Hz, 2H), 4.54 (t, J=5.8 Hz, 2H), 3.84 (m, 4H), 2.98 (t, J=5.8 Hz, 2H), 2.82 (m, 4H). MS: M+1 557

Biological Assays

The key experiment to exemplify store-operated Ca$^{2+}$-entry (SOCE), as it is referred to nowadays, is depicted in FIG. 1. In brief, emptying of the ER/SR store leads to opening of a plasma membrane channel through which Ca$^{2+}$ can flow back in the cell and these two phenomena can be dissected by adding Ca$^{2+}$ to the extracellular solution after the intracellular stores are depleted. This simple yet powerful experimental approach remains valid to unmask the phenomenon in screenings.

Cell Cultures

Immortalized primary mouse microglial BV-2 cells were obtained from ATCC (ATCC® CRL-2540™, Rockville, Md., USA) and were cultured in Dulbecco's Modified Eagle's Medium (DMEM; Sigma-Aldrich, Italy), supplemented with 10% heat-inactivated FBS (Gibco, Italy), 1-glutamine 50 mg/mL (Sigma-Aldrich, Italy), penicillin 10 U/mL and streptomycin 100 mg/mL (Sigma-Aldrich, Italy) at 37° C., under a 5% CO$_2$ humidified atmosphere. For experiments, the cells were plated 2×10$^4$ per ml in 24 well plates) or onto glass coverslips at concentrations of 4×10$^4$ per mL (24 mm diame-ter coverslips in 6 well plates).

Human embryonic kidney HEK cells were obtained from ATCC (ATCC® CRL-1573™, Rockville, Md., USA) and were cultured in Dulbecco's Modified Eagle's Medium (DMEM; Sigma-Aldrich, Italy), supplemented with 10% heat-inactivated FBS (Gibco, Italy), 1-glutamine 50 mg/mL (Sigma-Aldrich, Italy), penicillin 10 U/mL and streptomycin 100 mg/mL (Sigma-Aldrich, Italy) at 37° C., under a 5% CO2 humidified atmosphere. For experiments, the cells were plated onto glass coverslips at concentrations of $5 \times 10^4$ per mL (24 mm diame-ter coverslips in 6 well plates).

Immortalized line of human T lymphocyte Jurkat cells were achieved from ATCC (ATCC® TIB-152™, Rockville, Md., USA) and were cultured in Roswell Park Memorial Institute Medium (RPMI 1640; Sigma-Aldrich, Italy), supplemented with 10% heat-inactivated FBS (Gibco, Italy), 1-glutamine 50 mg/mL (Sigma-Aldrich, Italy), penicillin 10 U/mL and streptomycin 100 mg/mL (Sigma-Aldrich, Italy) at 37° C., under a 5% $CO_2$ humidified atmosphere. For experiments, the cells were plated onto glass coverslips at concentrations of $6 \times 10^4$ per mL (24 mm diameter coverslips in 6 well plates).

Fluo-4 Fluorimetric Assays to Determine the Activity of Novel Compounds Targeting SOCE BV-2 cells were loaded with 5 μM Fluo-4 AM in presence of 0.02% of Pluronic-127 (both from Life Technologies, Italy) and 10 μM sulfinpyrazone in Krebs-Ringer buffer (KRB, 135 mM NaCl, 5 mM KCl, 0.4 mM KH2PO4, 1 mM MgSO4, 5.5 mM glucose, 20 mM HEPES, pH 7.4) containing 2 mM $CaCl_2$ (30 min, room temperature). Subsequently, cells were washed and incubated with KRB for other 30 min to allow de-esterification of Fluo-4 AM. Experiments were carried out prior to and during exposure of the cells to the $Ca^{2+}$-free solution. In the absence of $Ca^{2+}$, the intracellular $Ca^{2+}$ stores were depleted by 2,5-t-butylhydroquinone (tBHQ, 50 μM; Sigma-Aldrich, Italy), a SERCA poison, and then calcium 2 mM was re-added to the extracellular solution. Fluorescence is then monitored sequentially for a second in each well for 600 seconds with excitation at 494 nm and an emission wavelength at 516 nm on the V3 Victor plate-reader (Perkin Elmer), generating time-curves for each well. Data were analysed using Microsoft Excel and GraphPad Prism.

The percentage of SOCE inhibition for each compound was determined based on value of tBHQ-induced calcium influx into BV-2 cells (Table 2). Surprisingly, the present inventors identified two first-in-class compounds that selectively potentiated calcium entry, such as 4-(1-(4-(3,5-bis (trifluoromethyl)-1H-pyrazol-1-yl)phenyl)-1H-1,2,3-triazol-4-yl)benzoic acid and 1-(4-(1-(4-chlorophenyl)-1H-1, 2,3-triazol-4-yl)phenyl)-5-(trifluoromethyl)-1H-pyrazole-4-carboxylate (Table 3).

TABLE 2

| Compound (BV-2 Cells) | % Inhibition (10 μM) |
|---|---|
| 1-(4-(4-phenyl-1H-1,2,3-triazol-1-yl)phenyl)-5-(trifluoromethyl)-1H-pyrazole-4-carboxylate | 14.30 |
| ethyl 1-(4-(4-(4-methoxyphenyl)-1H-1,2,3-triazol-1-yl)phenyl)-5-(trifluoromethyl)-1H-pyrazole-4-carboxylate | 4.77 |
| 1-(4-(4-(4-aminophenyl)-1H-1,2,3-triazol-1-yl)phenyl)-5-(trifluoromethyl)-1H-pyrazole-4-carboxylate | 8.31 |
| ethyl 1-(4-(4-(3-hydroxyphenyl)-1H-1,2,3-triazol-1-yl)phenyl)-5-(trifluoromethyl)-1H-pyrazole-4-carboxylate | 3.53 |

TABLE 2-continued

| Compound (BV-2 Cells) | % Inhibition (10 μM) |
|---|---|
| 1-(4-(4-(3-aminophenyl)-1H-1,2,3-triazol-1-yl)phenyl)-5-(trifluoromethyl)-1H-pyrazole-4-carboxylate | 24.75 |
| 1-(4-(4-(3,4-dimethoxyphenyl)-1H-1,2,3-triazol-1-yl)phenyl)-5-(trifluoromethyl)-1H-pyrazole-4-carboxylate | 17.17 |
| 1-(4-(4-(4-hydroxy-3-methoxyphenyl)-1H-1,2,3-triazol-1-yl)phenyl)-5-(trifluoromethyl)-1H-pyrazole-4-carboxylate | 34.95 |
| 1-(4-(4-(2-acetamidophenyl)-1H-1,2,3-triazol-1-yl)phenyl)-5-(trifluoromethyl)-1H-pyrazole-4-carboxylate | 27.96 |
| 3-(1-(4-(4-(ethoxycarbonyl)-5-(trifluoromethyl)-1H-pyrazol-1-yl)phenyl)-1H-1,2,3-triazol-4-yl)benzoic acid | 45.26 |
| 4-(1-(4-(4-(ethoxycarbonyl)-5-(trifluoromethyl)-1H-pyrazol-1-yl)phenyl)-1H-1,2,3-triazol-4-yl)benzoic acid | 40.08 |
| ethyl 1-(4-(4-(3-(methoxycarbonyl)phenyl)-1H-1,2,3-triazol-1-yl)phenyl)-5-(trifluoromethyl)-1H-pyrazole-4-carboxylate | 21.79 |
| ethyl 1-(4-(4-(3-carbamoylphenyl)-1H-1,2,3-triazol-1-yl)phenyl)-5-(trifluoromethyl)-1H-pyrazole-4-carboxylate | 2.27 |
| 1-(4-(3,5-bis(trifluoromethyl)-1H-pyrazol-1-yl)phenyl)-4-phenyl-1H-1,2,3-triazole | 0.84 |
| 4-(1-(4-(3,5-bis(trifluoromethyl)-1H-pyrazol-1-yl)phenyl)-1H-1,2,3-triazol-4-yl)butanoic acid | 19.91 |
| 3-(1-(4-(3,5-bis(trifluoromethyl)-1H-pyrazol-1-yl)phenyl)-1H-1,2,3-triazol-4-yl)phenol | 4.06 |
| 3-(1-(4-(3,5-bis(trifluoromethyl)-1H-pyrazol-1-yl)phenyl)-1H-1,2,3-triazol-4-yl)benzoic acid | 38.70 |
| 1-(4-(1-(4-methoxyphenyl)-1H-1,2,3-triazol-4-yl)phenyl)-5-(trifluoromethyl)-1H-pyrazole-4-carboxylate | 16.94 |
| 4-(4-(4-(ethoxycarbonyl)-5-(trifluoromethyl)-1H-pyrazol-1-yl)phenyl)-1H-1,2,3-triazol-1-yl)butanoic acid | 30.09 |
| 1-(4-(1-(3-aminophenyl)-1H-1,2,3-triazol-4-yl)phenyl)-5-(trifluoromethyl)-1H-pyrazole-4-carboxylate | 23.01 |
| ethyl 1-(4-(1-(pyridin-3-yl)-1H-1,2,3-triazol-4-yl)phenyl)-5-(trifluoromethyl)-1H-pyrazole-4-carboxylate | 37.44 |
| 1-(4-(1-(3-fluoropyridin-4-yl)-1H-1,2,3-triazol-4-yl)phenyl)-5-(trifluoromethyl)-1H-pyrazole-4-carboxylate | 37.69 |
| 1-(4-(1-(pyridin-4-yl)-1H-1,2,3-triazol-4-yl)phenyl)-5-(trifluoromethyl)-1H-pyrazole-4-carboxylate | 20.03 |
| 1-(4-(1-(3,4-dimethoxyphenyl)-1H-1,2,3-triazol-4-yl)phenyl)-5-(trifluoromethyl)-1H-pyrazole-4-carboxylate | 12.83 |
| 3-(4-(4-(ethoxycarbonyl)-5-(trifluoromethyl)-1H-pyrazol-1-yl)phenyl)-1H-1,2,3-triazol-1-yl)benzoic acid | 43.26 |
| 4-(4-(4-(ethoxycarbonyl)-5-(trifluoromethyl)-1H-pyrazol-1-yl)phenyl)-1H-1,2,3-triazol-1-yl)benzoic acid | 19.80 |
| 4-(4-(3,5-bis(trifluoromethyl)-1H-pyrazol-1-yl)phenyl)-1-(4-methoxyphenyl)-1H-1,2,3-triazole | 21.34 |
| 4-(4-(3,5-bis(trifluoromethyl)-1H-pyrazol-1-yl)phenyl)-1H-1,2,3-triazol-1-yl)butanoic acid | 18.30 |
| 4-(4-(3,5-bis(trifluoromethyl)-1H-pyrazol-1-yl)phenyl)-1-(3,4-dimethoxyphenyl)-1H-1,2,3-triazole | 5.70 |
| 3-(4-(4-(3,5-bis(trifluoromethyl)-1H-pyrazol-1-yl)phenyl)-1H-1,2,3-triazol-1-yl)benzoic acid | 30.53 |
| 3-(1-(4-(4-(methoxycarbonyl)-5-(trifluoromethyl)-1H-pyrazol-1-yl)phenyl)-1H-1,2,3-triazol-4-yl)benzoic acid | 12.36 |
| 3-(1-(4-(4-(isopropoxycarbonyl)-5-(trifluoromethyl)-1H-pyrazol-1-yl)phenyl)-1H-1,2,3-triazol-4-yl)benzoic acid | 74.63 |
| 3-(1-(4-(4-((pentan-2-yloxy)carbonyl)-5-(trifluoromethyl)-1H-pyrazol-1-yl)phenyl)-1H-1,2,3-triazol-4-yl)benzoic acid | 91.89 |
| 3-(1-(4-(4-((pyridin-4-ylmethoxy)carbonyl)-5-(trifluoromethyl)-1H-pyrazol-1-yl)phenyl)-1H-1,2,3-triazol-4-yl)benzoic acid | 54.61 |
| 3-(1-(4-(4-((benzyloxy)carbonyl)-5-(trifluoromethyl)-1H-pyrazol-1-yl)phenyl)-1H-1,2,3-triazol-4-yl)benzoic acid | 87.05 |
| 3-(1-(4-(4-((2-morpholinoethoxy)carbonyl)-5-(trifluoromethyl)-1H-pyrazol-1-yl)phenyl)-1H-1,2,3-triazol-4-yl)benzoic acid | 95.74 |

TABLE 3

| Compound | % Activation (10 μM) |
|---|---|
| 4-(1-(4-(3,5-bis(trifluoromethyl)-1H-pyrazol-1-yl)phenyl)-1H-1,2,3-triazol-4-yl)benzoic acid | 125.15 |
| 1-(4-(1-(4-chlorophenyl)-1H-1,2,3-triazol-4-yl)phenyl)-5-(trifluoromethyl)-1H-pyrazole-4-carboxylate | 47.07 |

FIG. 2A shows representative traces from a compound with no activity, and compounds that positively (4-(1-(4-(3,5-bis(trifluoromethyl)-1H-pyrazol-1-yl)phenyl)-1H-1,2,3-triazol-4-yl)benzoic acid) and negatively (3-(1-(4-(4-(ethoxycarbonyl)-5-(trifluoromethyl)-1H-pyrazol-1-yl)phenyl)-1H-1,2,3-triazol-4-yl)benzoic acid) regulated SOCE.

Biological Evaluation of Compounds Targeting SOCE by Fura-2 $Ca^{2+}$ Measurements Compounds were also tested on Jurkat cells in single-cell analysis using Fura-2 AM on cover-slips. Jurkat cells were loaded with 5 μM Fura-2 AM in presence of 0.02% of Pluronic-127 (both from Life Technologies, Italy) and 1 μM sulfinpyrazone in Krebs-Ringer buffer (KRB, 135 mM NaCl, 5 mM KCl, 0.4 mM $KH_2PO_4$, 1 mM $MgSO_4$, 5.5 mM glucose, 20 mM HEPES, pH 7.4) containing 2 mM $CaCl_2$ (30 min, room temperature). Afterwards, cells were washed and incubated with KRB for other 30 min to allow de-esterification of Fura-2AM. To measure store operated calcium entry, changes in cytosolic $Ca^{2+}$ were monitored upon depletion of the intracellular $Ca^{2+}$ stores. Experiments were carried out prior to and during exposure of the cells to the $Ca^{2+}$-free solution. In the absence of $Ca^{2+}$, the intracellular $Ca^{2+}$ stores were depleted by inhibition of the vesicular $Ca^{2+}$ pump by 2,5-t-butylhydroquinone (tBHQ, 50 μM; Sigma-Aldrich, Italy). Re-addition of 2 mM $Ca^{2+}$ allowed assessing the SOCE. During the experiments the cover-slips were mounted into acquisition chamber and placed on the stage of a Leica DMI6000 epi-fluorescent microscope equipped with S Fluor ×40/1.3 objective. Fura-2 was excited by alternate 340 and 380 nm using a Polychrome IV mono-chromator (Till Photon-ics, Germany) and the probe emission light was filtered through 520/20 band-pass filter and collected by a cooled CCD camera (Hamamatsu, Japan). The fluorescence signals were acquired and processed using MetaFluor software (Molecular Device, Sun-Nyvale, C A, USA). To quantify the differences in the amplitudes of $Ca^{2+}$ transients the ratio values were normalized using the formula ΔF/F0 (referred to as normalized Fura-2 ratio, "Norm. Fura ratio"). The percentage of SOCE modulation for each of 15 compounds was determined based on value of tBHQ-induced calcium influx into Jurkat cells. Data were analysed using Microsoft Excel and GraphPad Prism. Examples are presented in Tables 4 and 5.

TABLE 4

Jurkat Cells

| Compound | % Inhibition (10 μM) |
|---|---|
| 1-(4-(4-(4-hydroxy-3-methoxyphenyl)-1H-1,2,3-triazol-1-yl)phenyl)-5-(trifluoromethyl)-1H-pyrazole-4-carboxylate | 78.37 |
| 3-(1-(4-(4-(ethoxycarbonyl)-5-(trifluoromethyl)-1H-pyrazol-1-yl)phenyl)-1H-1,2,3-triazol-4-yl)benzoic acid | 70.39 |
| 4-(1-(4-(4-(ethoxycarbonyl)-5-(trifluoromethyl)-1H-pyrazol-1-yl)phenyl)-1H-1,2,3-triazol-4-yl)benzoic acid | 32.31 |
| 3-(1-(4-(3,5-bis(trifluoromethyl)-1H-pyrazol-1-yl)phenyl)-1H-1,2,3-triazol-4-yl)benzoic acid | 38.26 |
| 4-(4-(4-(ethoxycarbonyl)-5-(trifluoromethyl)-1H-pyrazol-1-yl)phenyl)-1H-1,2,3-triazol-1-yl)butanoic acid | 19.13 |
| 1-(4-(1-(3-fluoropyridin-4-yl)-1H-1,2,3-triazol-4-yl)phenyl)-5-(trifluoromethyl)-1H-pyrazole-4-carboxylate | 32.87 |
| 3-(4-(4-(4-(ethoxycarbonyl)-5-(trifluoromethyl)-1H-pyrazol-1-yl)phenyl)-1H-1,2,3-triazol-1-yl)benzoic acid | 63.65 |
| 3-(4-(4-(3,5-bis(trifluoromethyl)-1H-pyrazol-1-yl)phenyl)-1H-1,2,3-triazol-1-yl)benzoic acid | 39.68 |
| 3-(1-(4-(4-(methoxycarbonyl)-5-(trifluoromethyl)-1H-pyrazol-1-yl)phenyl)-1H-1,2,3-triazol-4-yl)benzoic acid | 21.75 |
| 3-(1-(4-(4-(isopropoxycarbonyl)-5-(trifluoromethyl)-1H-pyrazol-1-yl)phenyl)-1H-1,2,3-triazol-4-yl)benzoic acid | 93.87 |
| 3-(1-(4-(4-((pentan-2-yloxy)carbonyl)-5-(trifluoromethyl)-1H-pyrazol-1-yl)phenyl)-1H-1,2,3-triazol-4-yl)benzoic acid | / |
| 3-(1-(4-(4-((pyridin-4-ylmethoxy)carbonyl)-5-(trifluoromethyl)-1H-pyrazol-1-yl)phenyl)-1H-1,2,3-triazol-4-yl)benzoic acid | 56.95 |
| 3-(1-(4-(4-((benzyloxy)carbonyl)-5-(trifluoromethyl)-1H-pyrazol-1-yl)phenyl)-1H-1,2,3-triazol-4-yl)benzoic acid | 33.47 |
| 3-(1-(4-(4-((2-morpholinoethoxy)carbonyl)-5-(trifluoromethyl)-1H-pyrazol-1-yl)phenyl)-1H-1,2,3-triazol-4-yl)benzoic acid | 25.08 |

TABLE 5

Jurkat Cells

| Compound | % Activation (10 μM) |
|---|---|
| 4-(1-(4-(3,5-bis(trifluoromethyl)-1H-pyrazol-1-yl)phenyl)-1H-1,2,3-triazol-4-yl)benzoic acid | 136.42 |
| 1-(4-(1-(4-chlorophenyl)-1H-1,2,3-triazol-4-yl)phenyl)-5-(trifluoromethyl)-1H-pyrazole-4-carboxylate | 97.32 |
| 1-(4-(1-(4-chlorophenyl)-1H-1,2,3-triazol-4-yl)phenyl)-5-(trifluoromethyl)-1H-pyrazole-4-carboxylic acid | 100.13 |
| 1-(4-(1-(4-chlorophenyl)-1H-1,2,3-triazol-4-yl)phenyl)-5-(trifluoromethyl)-1H-pyrazole-4-carboxylate | 122.94 |
| 1-(4-(1-(4-chlorophenyl)-1H-1,2,3-triazol-4-yl)phenyl)-5-(trifluoromethyl)-1H-pyrazole-4-carboxylate | 126.78 |

Pharmacological Modulation of Mutated Orai1 and STIM1

Figure 3:
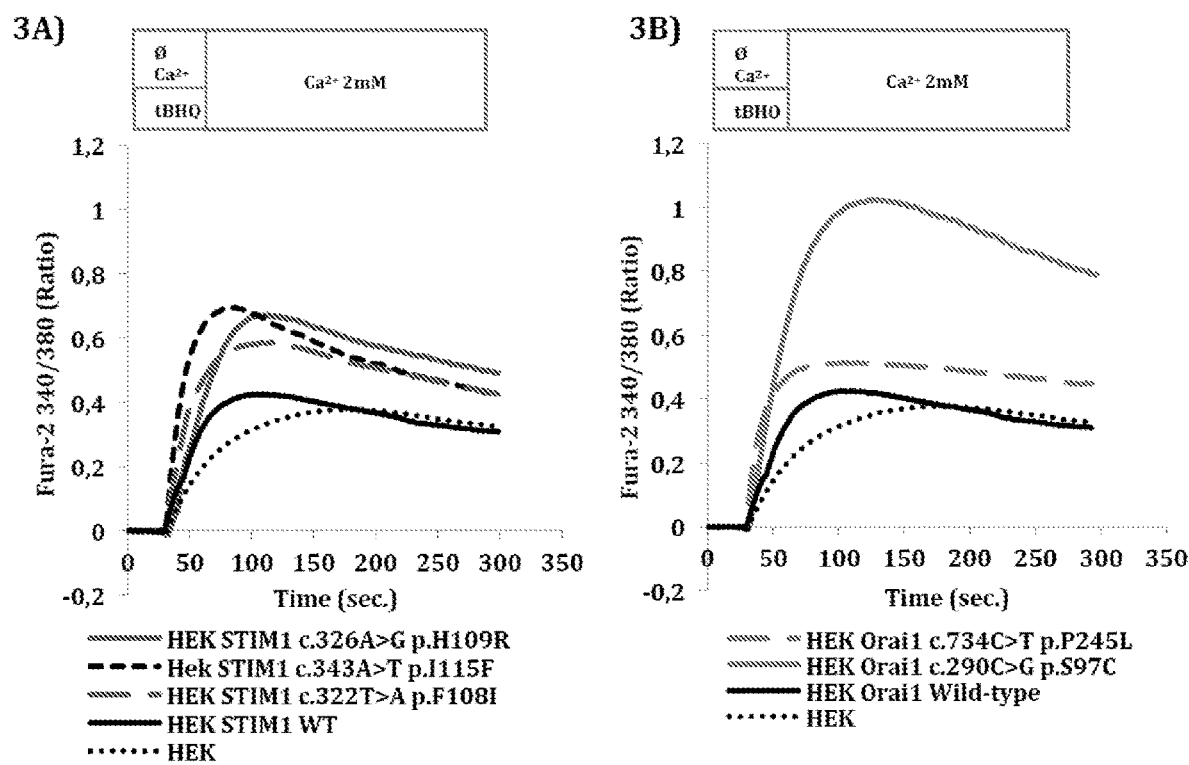
FIG. 3: SOCE is potentiated in HEK cells expressing STIM1 and Orai1 mutated forms.
SOCE induced by tBHQ in wilde-type HEK cells or HEK cells overexpressing the indicated STIM1 (A) or Orai1 (B) proteins. Average traces of approx. 600 cells from 20 coverslips performed on 4 separate days for each condition.

Wild type and mutated plasmids encoding proteins present in TAM patients were transiently transfected in HEK cells to evaluate SOCE. Given that tubular aggregate myopathy (TAM) is a dominant disorder, it was reasoned that a cellular phenotype should have been observable also in the presence of endogenous wild-type protein. As seen in FIG. 3, HEK cells over-expressing wild-type STIM1 or Orai1 display an increased SOCE compared to control cells. When cells are transfected with any of the three mutated forms of STIM1 a further significant increase in both rate and overall SOCE is observed (FIG. 3A). Similarly, both Orai1 mutants yielded similar results, with a potentiation of rate and overall SOCE (FIG. 3B). Importantly, this demonstrates that the molecular phenotype of TAM can be recapitulated in an in vitro system by compounds exemplified in this document.

Figure 4A:
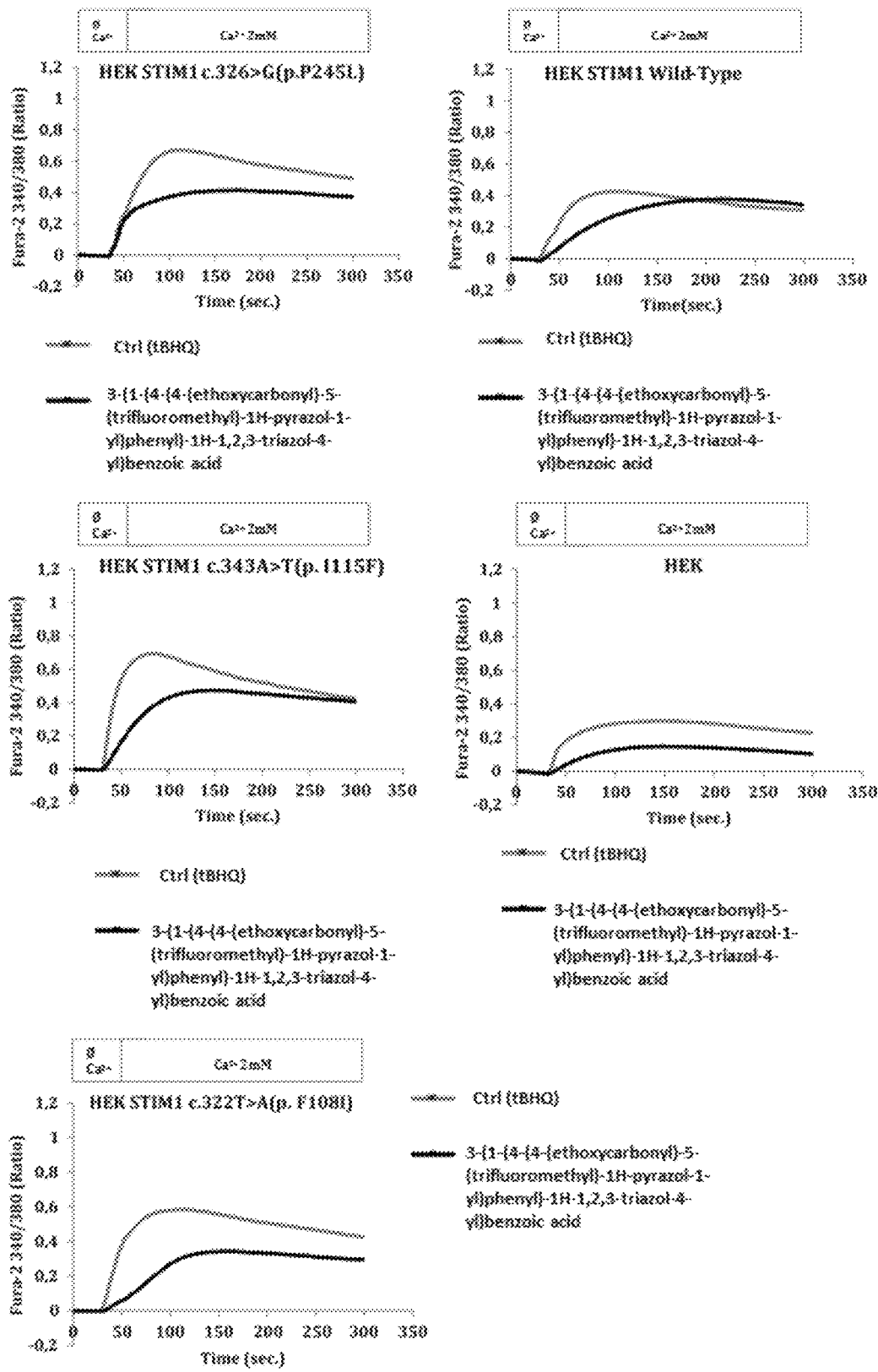
FIG. 4: Evaluation of 3-(1-(4-(4-(ethoxycarbonyl)-5-(trifluoromethyl)-1H-pyrazol-1-yl)phenyl)-1H-1,2,3-triazol-4-yl)benzoic acid effects in STIM1 and Orai1 mutated cells.
3-(1-(4-(4-(ethoxycarbonyl)-5-(trifluoromethyl)-1H-pyrazol-1-yl)phenyl)-1H-1,2,3-triazol-4-yl)benzoic acid 10 μM impairs SOCE both in Wild-type and STIM1 (A) or Orai1 (B) mutated cells. In detail, the compound is able to revert the over-activation of STIM1 and Orai1 mutated proteins.
Figure 4B:
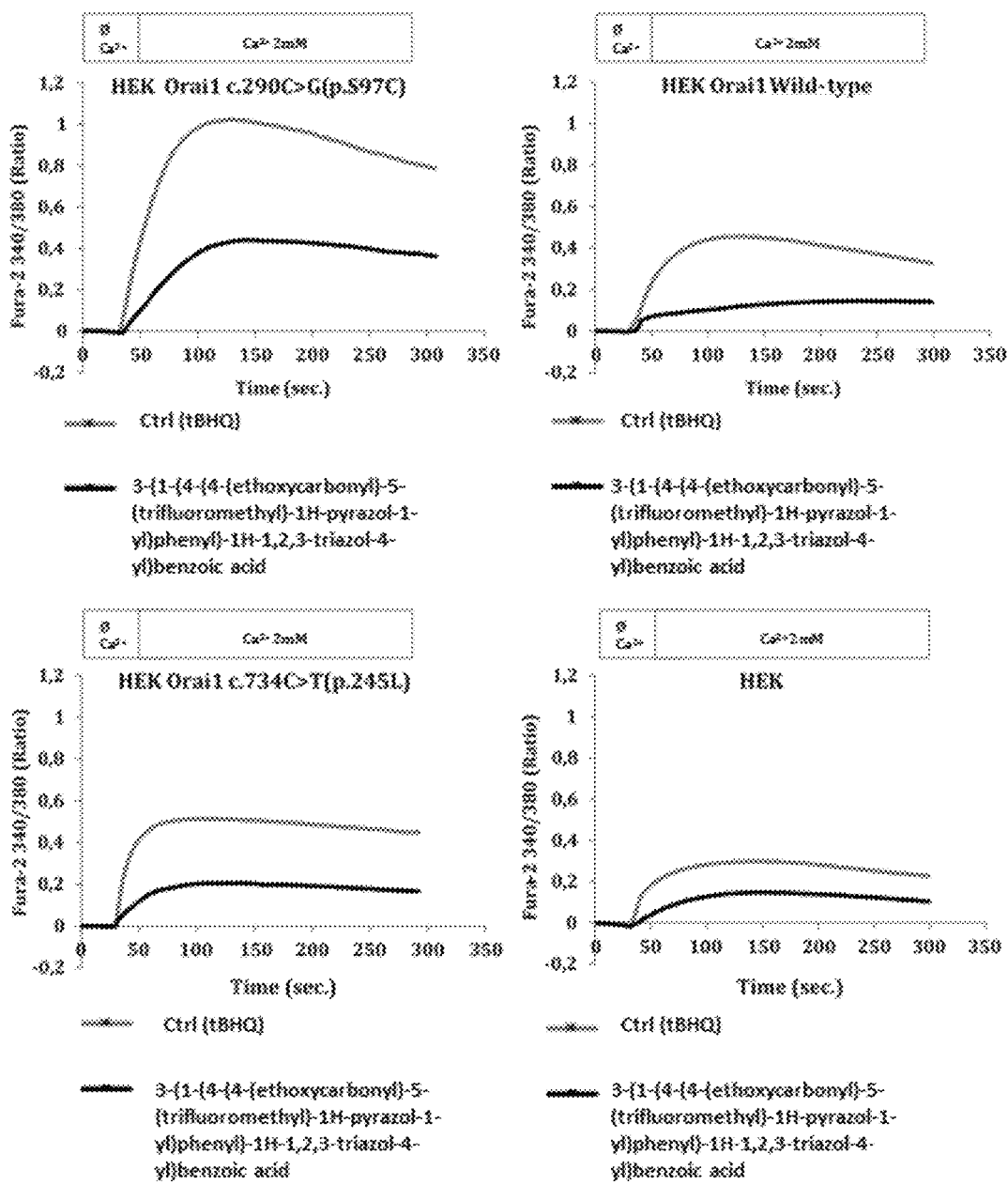

The effect of compound 3-(1-(4-(4-(ethoxycarbonyl)-5-(trifluoromethyl)-1H-pyrazol-1-yl)phenyl)-1H-1,2,3-triazol-4-yl)benzoic acid on these mutations is presented in FIG. 4. As it can be observed, the compound is able to revert the over-activation of STIM1 and Orai1 mutated proteins (FIGS. 4A and 4B). FIG. 5 shows a dose-response of the same compound as an example on two mutations.

The invention claimed is:

1. A compound of formula (I)

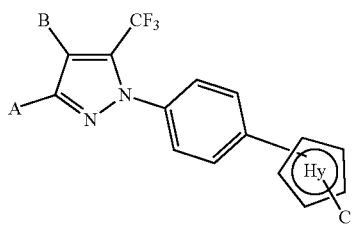
(I)

wherein:
A is selected from H or $CF_3$;
B is selected from H, COOH or $COOR_1$;
ring Hy is selected from:

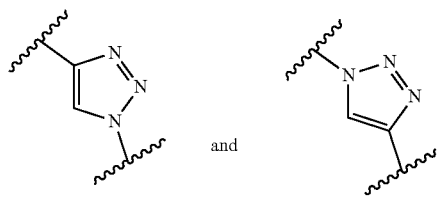 [SMILES: *c1cn(*)nn1 ; *c1cn(*)nn1]
and

C is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_m$—$C_{1-8}$ alkyl, $(CH_2)_m$—$C_{2-8}$ alkenyl, $(CH_2)_m$—$C_{2-8}$ alkynyl group, $(CH_2)_m$-cycloalkyl, $(CH_2)_m$-aryl and $(CH_2)_m$-heterocyclic group, wherein m is an integer 1 to 4;
$R_1$ is selected from unsubstituted or substituted $C_{1-8}$ alkyl group, unsubstituted or substituted $C_{2-8}$ alkenyl group, unsubstituted or substituted $C_{2-8}$ alkynyl group, unsubstituted or substituted $C_{3-6}$ cycloalkyl, unsubstituted or substituted aryl, unsubstituted or substituted heterocyclic group, $(CH_2)_n$—$C_{1-8}$ alkyl, $(CH_2)_n$—$C_{2-8}$ alkenyl, $(CH_2)_n$—$C_{2-8}$ alkynyl group, $(CH_2)_n$-cycloalkyl, $(CH_2)_n$-aryl and $(CH_2)_n$-heteroaryl, wherein n is an integer 1 to 4; or
pharmaceutically acceptable hydrates and/or solvates and/or salts and/or esters and/or pro-drugs thereof.

2. The compound according to claim 1 having formula (II):

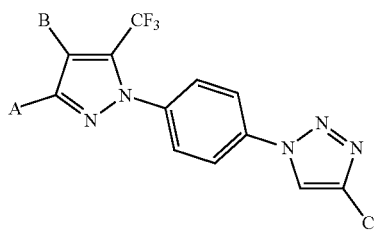
(II)

wherein A, B and C have the meaning as defined in claim 1, or
pharmaceutically acceptable hydrates and/or solvates and/or salts and/or esters and/or prodrugs thereof.

3. The compound according to claim 1 having formula (II):

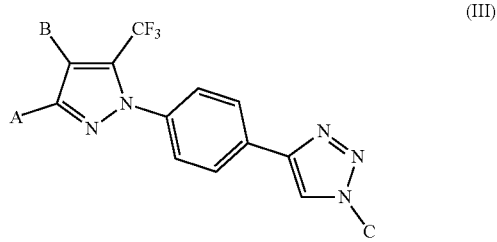
(III)

wherein A, B and C have the meaning as defined in claim 1, or
pharmaceutically acceptable hydrates and/or solvates and/or salts and/or esters and/or pro-drugs thereof.

4. The compound according to claim 1, wherein when $R_1$, if present, and C are independently selected from substituted $C_{1-8}$ alkyl group, substituted $C_{3-6}$ cycloalkyl, substituted aryl, substituted heterocyclic group, substituted $C_{2-8}$ alkenyl group, substituted $C_{2-8}$ alkynyl group, the substituents are independently selected from halogen, —$CH_3$, —$CH_2F$, —$CHF_2$, —$CF_3$, —$OR_2$, —CN, —$COOR_2$, —$CONR_2R_3$, —$NR_2R_3$, —$NHCOR_2$, —$NHSO_2R_2$, —$S(O)R_2$, —$S(O)_2R_2$, and —$SO_2NHR_2$;
wherein $R_2$ and $R_3$ are the same or different and independently selected from H, $C_1$-$C_8$ alkyl group unsubstituted or substituted with one or more halogen atoms and $C_3$-$C_6$ cycloalkyl group unsubstituted or substituted with one or more halogen atoms.

5. The compound according to claim 1, wherein B is selected from H, and COOH.

6. The compound according to claim 1, wherein $R_1$ is selected from unsubstituted methyl, ethyl, tert-butyl, isopropyl, pentan-2-yl, pyridine-4-yl methyl, benzyl, 2-morpholinoethyl, and 1,1,1,3,3,3-hexafluoro-2-methylpropan-2-yl.

7. The compound according to claim 1, wherein C is selected from:

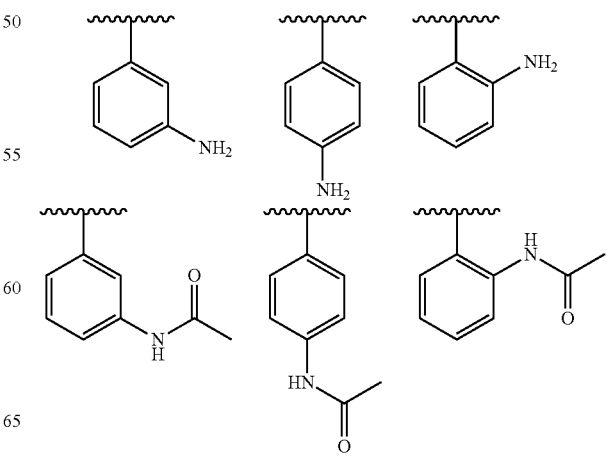

-continued

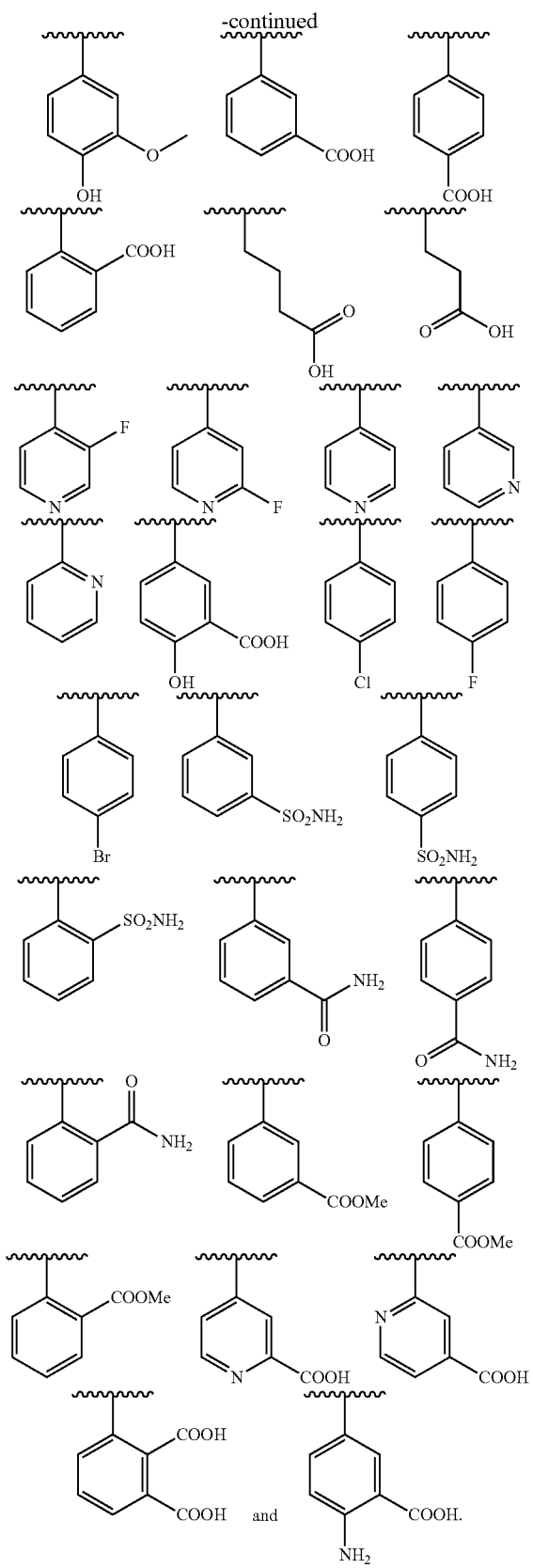

8. The compound according to claim 1, selected from:
ethyl 1-(4-(4-phenyl-1H-1,2,3-triazol-1-yl)phenyl)-5-(trifluoromethyl)-1H-pyrazole-4-carboxylate ethyl 1-(4-(4-(4-methoxyphenyl)-1H-1,2,3-triazol-1-yl)phenyl)-5-(trifluoromethyl)-1H-pyrazole-4-carboxylate
ethyl 1-(4-(4-(3,5-dimethoxyphenyl)-1H-1,2,3-triazol-1-yl)phenyl)-5-(trifluoromethyl)-1H-pyrazole-4-carboxylate
4-(1-(4-(4-(ethoxycarbonyl)-5-(trifluoromethyl)-1H-pyrazol-1-yl)phenyl)-1H-1,2,3-triazol-4-yl)butanoic acid
ethyl 1-(4-(4-(4-aminophenyl)-1H-1,2,3-triazol-1-yl)phenyl)-5-(trifluoromethyl)-1H-pyrazole-4-carboxylate
ethyl 1-(4-(4-(3-hydroxyphenyl)-1H-1,2,3-triazol-1-yl)phenyl)-5-(trifluoromethyl)-1H-pyrazole-4-carboxylate
ethyl 1-(4-(4-(4-chlorophenyl)-1H-1,2,3-triazol-1-yl)phenyl)-5-(trifluoromethyl)-1H-pyrazole-4-carboxylate
ethyl 1-(4-(4-(3-aminophenyl)-1H-1,2,3-triazol-1-yl)phenyl)-5-(trifluoromethyl)-1H-pyrazole-4-carboxylate
ethyl 1-(4-(4-(pyridin-3-yl)-1H-1,2,3-triazol-1-yl)phenyl)-5-(trifluoromethyl)-1H-pyrazole-4-carboxylate
ethyl 1-(4-(4-(3-aminophenyl)-1H-1,2,3-triazol-1-yl)phenyl)-5-(trifluormethyl)-1H-pyrazole-4-carboxylate
ethyl 1-(4-(4-(pyridin-2-yl)-1H-1,2,3-triazol-1-yl)phenyl)-5-(trifluoromethyl)-1H-pyrazole-4-carboxylate
ethyl 1-(4-(4-pyridin-4-yl)-1H-1,2,3-triazol-1-yl)phenyl)-5-(trifluoromethyl)-1H-pyrazole-4-carboxylate
ethyl 1-(4-(4-(3,4-dimethoxyphenyl)-1H-1,2,3-triazol-1-yl)phenyl)-5-(trifluoromethyl)-1H-pyrazole-4-carboxylate
ethyl 1-(4-(4-(4-hydroxy-3-methoxyphenyl)-1H-1,2,3-triazol-1-yl)phenyl)-5-(trifluoromethyl)-1H-pyrazole-4-carboxylate
ethyl 1-(4-(4-(3-methoxyphenyl)-1H-1,2,3-triazol-1-yl)phenyl)-5-(trifluoromethyl)-1H-pyrazole-4-carboxylate
ethyl 1-(4-(4-(2-acetamidophenyl)-1H-1,2,3-triazol-1-yl)phenyl)-5-(trifluoro methyl)-1H-pyrazole-4-carboxylate
ethyl 1-(4-(4-(3-acetamidophenyl)-1H-1,2,3-triazol-1-yl)phenyl)-5-(trifluoromethyl)-1H-pyrazole-4-carboxylate
ethyl 1-(4-(4-(2-acetamidophenyl)-1H-1,2,3-triazol-1-yl)phenyl)-5-(trifluoromethyl)-1H-pyrazole-4-carboxylate
3-(1-(4-(4-(ethoxycarbonyl)-5-(trifluoromethyl)-1H-pyrazol-1-yl)phenyl)-1H-1,2,3-triazol-4-yl)benzoic acid
4-(1-(4-(4-(ethoxycarbonyl)-5-(trifluoromethyl)-1H-pyrazol-1-yl)phenyl)-1H-1,2,3-triazol-4-yl)benzoic acid
ethyl 1-(4-(4-(4-phenoxyphenyl)-1H-1,2,3-triazol-1-yl)phenyl)-5-(trifluoromethyl)-1H-pyrazole-4-carboxylate
1-(4-(3,5-bis(trifluoromethyl)-1H-pyrazol-1-yl)phenyl)-4-phenyl-1H-1,2,3-triazole
1-(4-(3,5-bis(trifluoromethyl)-1H-pyrazol-1-yl)phenyl)-4-(4-methoxyphenyl)-1H-1,2,3-triazole
1-(4-(3,5-bis(trifluoromethyl)-1H-pyrazol-1-yl)phenyl)-4-(3,5-dimethoxyphenyl)-1H-1,2,3-triazole
4-(1-(4-(3,5-bis(trifluoromethyl)-1H-pyrazol-1-yl)phenyl)-1H-1,2,3-triazol-4-yl)butanoic acid
4-(1-(4-(3,5-bis(trifluoromethyl)-1H-pyrazol-1-yl)phenyl)-1H-1,2,3-triazol-4-yl)aniline
3-(1-(4-(3,5-bis(trifluoromethyl)-1H-pyrazol-1-yl)phenyl)-1H-1,2,3-triazol-4-yl)phenol
1-(4-(3,5-bis(trifluoromethyl)-1H-pyrazol-1-yl)phenyl)-4-(4-chlorophenyl)-1H-1,2,3-triazole 3-(1-(4-(3,5-bis(trifluoromethyl)-1H-pyrazol-1-yl)phenyl)-1H-1,2,3-triazol-4-yl)aniline
3-(1-(4-(3,5-bis(trifluoromethyl)-1H-pyrazol-1-yl)phenyl)-1H-1,2,3-triazol-4-yl)pyridine
4-(1-(4-(3,5-bis(trifluoromethyl)-1H-pyrazol-1-yl)phenyl)-1H-1,2,3-triazol-4-yl)-3-fluoropyridine
2-(1-(4-(3,5-bis(trifluoromethyl)-1H-pyrazol-1-yl)phenyl)-1H-1,2,3-triazol-4-yl)pyridine
4-(1-(4-(3,5-bis(trifluoromethyl)-1H-pyrazol-1-yl)phenyl)-1H-1,2,3-triazol-4-yl)pyridine
1-(4-(3,5-bis(trifluoromethyl)-1H-pyrazol-1-yl)phenyl)-4-(3,4-dimethoxyphenyl)-1H-1,2,3-triazole
4-(1-(4-(3,5-bis(trifluoromethyl)-1H-pyrazol-1-yl)phenyl)-1H-1,2,3-triazol-4-yl)-2-methoxyphenol
1-(4-(3,5-bis(trifluoromethyl)-1H-pyrazol-1-yl)phenyl)-4-(3-methoxyphenyl)-1H-1,2,3-triazole
N-(4-(1-(4-(3,5-bis(trifluoromethyl)-1H-pyrazol-1-yl)phenyl)-1H-1,2,3-triazol-4-yl)phenyl)acetamide
N-(3-(1-(4-(3,5-bis(trifluoromethyl)-1H-pyrazol-1-yl)phenyl)-1H-1,2,3-triazol-4-yl)phenyl)acetamide
N-(2-(1-(4-(3,5-bis(trifluoromethyl)-1H-pyrazol-1-yl)phenyl)-1H-1,2,3-triazol-4-yl)phenyl)acetamide
N-(2-(1-(4-(3,5-bis(trifluoromethyl)-1H-pyrazol-1-yl)phenyl)-1H-1,2,3-triazol-4-yl)phenyl)acetamide
4-(1-(4-(3,5-bis(trifluoromethyl)-1H-pyrazol-1-yl)phenyl)-1H-1,2,3-triazol-4-yl)benzoic acid
1-(4-(3,5-bis(trifluoromethyl)-1H-pyrazol-1-yl)phenyl)-4-(4-phenoxyphenyl)-1H-1,2,3-triazole
ethyl 1-(4-(1-phenyl-1H-1,2,3-triazol-4-yl)phenyl)-5-(trifluoromethyl)-1H-pyrazole-4-carboxylate
ethyl 1-4-(1-(4-methoxyphenyl)-1H-1,2,3-triazol-4-yl)phenyl)-5-(trifluoromethyl)-1H-pyrazole-4-carboxylate
ethyl 1-(4-(1-(3,5-dimethoxyphenyl)-1H-1,2,3-triazol-4-yl)phenyl)-5-(trifluoromethyl)-1H-pyrazole-4-carboxylate
4-(4-(4-(4-(ethoxycarbonyl)-5-(trifluoromethyl)-1H-pyrazol-1-yl)phenyl)-1H-1,2,3-triazol-1-yl)butanoic acid
ethyl 1-(4-(1-(4-aminophenyl)-1H-1,3-triazol-4-yl)phenyl)-5-(trifluoromethyl)-1H-pyrazole-4-carboxylate
ethyl 1-4-(1-(3-hydroxyphenyl)-1H-1,2,3-triazol-4-yl)phenyl)-5-(trifluoromethyl)-1H-pyrazole-4-carboxylate
ethyl 1-(4-(1-(4-chiorophenyl)-1H-1,2,3-triazol-4-yl)phenyl)-5-(trifluoromethyl)-1H-pyrazole-4-carboxylate
ethyl 1-(4-(1-(3-aminophenyl)-1H-1,2,3-triazol-4-yl)phenyl)-5-(trifluoromethyl)-1H-pyrazole-4-carboxylate
ethyl 1-4-(1-(pyridin-3-yl)-1H-1,2,3-triazol-4-yl)phenyl)-5-(trifluoromethyl)-1H-pyrazole-4-carboxylate
ethyl 1-(4-(1-(3-fluoropyridin-4-yl)-1H-1,2,3-triazol-4-yl)phenyl)-5-(trifluoromethyl)-1H-pyrazole-4-carboxylate
ethyl 1-(4-(1-(pyridin-2-yl)-1H-1,2,3-triazol-4-yl)phenyl)-5-(trifluoromethyl)-1H-pyrazole-4-carboxylate
ethyl 1-(4-(1-(pyridin-4-yl)-1H-1,2,3-triazol-4-yl)phenyl)-5-(trifluoro methyl)-1H-pyrazole-4-carboxylate
ethyl 1-(4-(1-(3,4-dimethoxyphenyl)-1H-1,2,3-triazol-4-yl)phenyl)-5-(trifluoromethyl)-1H-pyrazole-4-carboxylate
ethyl 1-(4-(1-(4-hydroxy-3-methoxyphenyl)-1H-1,2,3-triazol-4-yl)phenyl)-5-(trifluoromethyl)-1H-pyrazole-4-carboxylate
ethyl 1-(4-(1-(3-methoxyphenyl)-1H-1,2,3-triazol-4-yl)phenyl)-5-(trifluoromethyl)-1H-pyrazole-4-carboxylate
ethyl 1-(4-(1-(4-acetamidophenyl)-1H-1,2,3-triazol-4-yl)phenyl)-5-(trifluoromethyl)-1H-pyrazole-4-carboxylate
ethyl 1-(4-(1-(3-acetamidophenyl)-1H-1,2,3-triazol-4-yl)phenyl)-5-(trifluoromethyl)-1H-pyrazole-4-carboxylate
ethyl 1-(4-(1-(2-acetamidophenyl)-1H-1,2,3-triazol-1-yl)phenyl)-5-(trifluoromethyl)-1H-pyrazole-4-carboxylate
3-(4-(4-(4-(ethoxycarbonyl)-5-(trifluoromethyl)-1H-pyrazol-1-yl)phenyl)-1H-1,2,3-triazol-1-yl)benzoic acid
4-(4-(4-(4-(ethoxycarbonyl)-5-(trifluoromethyl)-1H-pyrazol-I-yl)phenyl)-1H-1,2,3-triazol-1-yl)benzoic acid
ethyl 1-(4-(1-(4-phenoxyphenyl)-1H-1,2,3-triazol-4-yl)phenyl)-5-(trifluoromethyl)-1H-pyrazole-4-carboxylate
4-(4-(3,5-bis(trifluoromethyl)-1H-pyrazol-1-yl)phenyl)-1-phenyl-1H-1,2,3-triazole
4-(4-(3,5-bis(trifluoromethyl)-1H-pyrazol-1-yl)phenyl)-1-(4-methoxyphenyl)-1H-1,2,3-thiazole
4-(4-(3,5-bis(trifluoromethyl)-1H-pyrazol-1-yl)phenyl-1-(3,5-dimethoxyphenyl)-1H-1,2,3-triazole
4-(4-(4-(3,5-bis(trifluoromethyl)-1H-pyrazol-1-yl)phenyl)-1H-1,2,3-triazol-1-yl)butanoic acid
4-(4-(4-(3,5-bis(trifluoromethyl)-1H-pyrazol-1-yl)phenyl)-1H-1,2,3-triazol-1-yl)aniline
3-(5-(4-(3,5-bis(trifluoromethyl)-1H-pyrazol-1-yl)phenyl)-3H-pyrazol-3-yl)phenol
4-(4-(3,5-bis(trifluoromethyl)-1H-pyrazol-1-yl)phenyl)-1-(4-chlorophenyl)-1H-1,2,3-triazole
3-(4-(4-(3,5-bis(trifluoromethyl)-1H-pyrazol-1l-yl)phenyl)-1H-1,2,3-triazol-1-yl)aniline
3-(4-(4-(3,5-bis(trifluoromethyl)-1H-pyrazol-1-yl)phenyl)-1H-1,2,3-triazol-1-yl)pyridine
4-(4-(4-(3,5-bis(trifluoromethyl)-1H-pyrazol-1-yl)phenyl)-1H-1,2,3-triazol-1-yl)-3-fluoropyridine
2-(4-(4-(3,5-bis(trifluoromethyl)-1H-pyrazol-1-yl)phenyl)-1H-1,2,3-triazol-1-yl)pyridine
4-(4-(4-(3,5-bis(trifluoromethyl)-1H-pyrazol-1-yl)phenyl)-1H-1,2,3-triazol-1-yl)pyridine
4-(4-(3,5-bis(trifluoromethyl)-1H-pyrazol-1-yl)phenyl)-1-(3,4-dimethoxyphenyl)-1H-1,2,3-triazole
4-(4-(4-(3,5-bis(trifluoromethyl)-1H-pyrazol-1-yl)phenyl)-1H-1,2,3-triazol-1-yl)-2-methoxyphenol
4-(4-(3,5-bis(trifluoromethyl)-1H-pyrazol-1-yl)phenyl)-1-(3-methoxyphenyl)-1H-1,2,3-triazole
N-(4-(4-(4-(3,5-bis(trifluoromethyl)-1H-pyrazol-1-yl)phenyl)-1H-1,2,3-triazol-1-yl)phenyl)acetamide
N-(3-(4-(4-(3,5-bis(trifluoromethyl)-1H-pyrazol-1-yl)phenyl)-1H-1,2,3-triazol-1-yl)phenyl)acetamide
3-(4-(4-(3,5-bis(trifluoromethyl)-1H-pyrazol-1-yl)phenyl)-1H-1,2,3-triazol-1-yl)benzoic acid
4-(4-(4-(3,5-bis(trifluoromethyl)-1H-pyrazol-1-yl)phenyl)-1H-1,2,3-triazol-1-yl)benzoic acid
4-(4-(3,5-bis(trifluoromethyl)-1H-pyrazol-1-yl)phenyl)-1-(4-phenoxyphenyl)-1H-1,2,3-triazole
ethyl 1-(4-(4-(3-carbamoylphenyl)-1H-1,2,3-triazol-1-yl)phenyl)-5-(trifluoromethyl)-1H-pyrazole-4-carboxylate
ethyl 1-(4-(4-(3-(methoxycarbonyl)phenyl)-1H-1,2,3-triazol-1-yl)phenyl)-5-(trifluoromethyl)-1H-pyrazole-4-carboxylate
ethyl 1-(4-(4-(3-sulfamoylphenyl)-1H-1,2,3-triazol-1-yl)phenyl)-5-(trifluoromethyl)-1H-pyrazole-4-carboxylate methyl 1-(4-(1-(4-chlorophenyl)-1H-1,2,3-triazol-4-yl)phenyl)-5-(trifluoromethyl)-1H-pyrazole-4-carboxylate tert-butyl 1-(4-(1-(4-chlorophenyl)-1H-1,2,3-triazol-4-yl)phenyl)-5-(trifluoromethyl)-1H-pyrazole-4-carboxylate isopropyl 1-(4-(1-(4-chlorophenyl)-1H-1,2,3-triazol-4-yl)phenyl)-5-(trifluoromethyl)-1H-pyrazole-4-carboxylate 1-(4-(1-(4-chlorophenyl)-1H-1,2,3-triazol-4-yl)phenyl)-5-(trifluoromethyl)-1H-pyrazole-4-carboxylic acid 3-(1-(4-(4-(methoxycarbonyl)-5-(trifluoromethyl)-1H-pyrazol-1-yl)phenyl)-1H-1,2,3-triazol-4-yl)benzoic acid 3-(1-(4-(4-(isopropoxycarbonyl)-5-(trifluoromethyl)-1H-pyrazol-1-yl)phenyl)-1H-1,2,3-triazol-4-yl)benzoic acid 3-(1-(4-(4-((pentan-2-yloxy)carbonyl)-5-(trifluoromethyl)-1H-pyrazol-1-yl)phenyl)-1H-1,2,3-triazol-4-yl)benzoic acid 3-(1-(4-(4-((pyridin-4-ylmethoxy)carbonyl)-5-(trifluoromethyl)-1H-pyrazol-1-yl)phenyl)-1H-1,2,3-triazol-4-yl)benzoic acid -(1-(4-(4-((benzyloxy)carbonyl)-5-(trifluoromethyl)-1H-pyrazol-1-yl)phenyl)-1H-1,2,3-triazol-4-yl)benzoic acid 3-(1-(4-(4-((2-morpholinoethoxy)carbonyl)-5-(trifluoromethyl)-1H-pyrazol-1-yl)phenyl)-1H-1,2,3-triazol-4-yl)benzoic acid 3-1-(4-(4-(((1,1,1,3,3,3-hexafluoro-2-methylpropan-2-yl)oxy)carbonyl)-5-(trifluoromethyl)-1H-pyrazol-1-yl)phenyl)-1H-1,2,3-triazol-4-yl)benzoic acid 4-(1-(4-(4-(isopropoxycarbonyl)-5-(trifluoromethyl)-1H-pyrazol-1-yl)phenyl)-1H-1,2,3-triazol-4-yl)picolinic acid 2-(1-(4-(4-(isopropoxycarbonyl)-5-trifluoromethyl)-1H-pyrazol-1-yl)phenyl)-1H-1,2,3-triazol-4-yl)isonicotinic acid 4-(1-(4-(4-(isopropoxycarbonyl)-5-(trifluoromethyl)-1H-pyrazol-I-yl)phenyl)-1H-1,2,3-triazol-4-yl)phthalic acid 2-amino-5-(1-(4-(4-(isopropoxycarbonyl)-5-(trifluoromethyl)-1H-pyrazol-1-yl)phenyl)-1H-1,2,3-triazol-4-yl)benzoic acid and 2-hydroxy-5-(1-(4-(4-(isopropoxycarbonyl)-5-(trifluoromethyl)-1H-pyrazol-1-yl)phenyl)-1H-1,2,3-triazol-4-yl)benzoic acid.

9. A method of treating a disease linked to loss- or gain-of-function STIM1/Orai1 mutations comprising administering at least one compound according to claim 1 to a patient in need thereof.

10. A pharmaceutical composition comprising at least one compound according to claim 1 and a pharmaceutically acceptable carrier and/or vehicle.

11. The method of claim 9, wherein the disease linked to loss- or gain-of-function STIM1/Orai1 mutations is selected from the group consisting of: tubular aggregate myopathy (TAM), Stormorken syndrome, York platelet syndrome, immunodeficiencies, T-cell immunodeficiency, lymphoproliferative disease, autoimmunity, congenital myopathy, anhydrosis, dental enamel, an impairment in thrombus formation due to a defect in platelet activation, and combinations thereof.

* * * * *